US008079968B2

(12) United States Patent
Hoffmann

(10) Patent No.: US 8,079,968 B2
(45) Date of Patent: *Dec. 20, 2011

(54) VIBRATOR WITH A PLURALITY OF CONTACT NODES FOR TREATMENT OF MYOCARDIAL ISCHEMIA

(75) Inventor: Andrew Kenneth Hoffmann, Burnaby (CA)

(73) Assignee: AHOF Biophysical Systems Inc., Burnaby (CA)

( * ) Notice: Subject to any disclaimer, the term of this patent is extended or adjusted under 35 U.S.C. 154(b) by 615 days.

This patent is subject to a terminal disclaimer.

(21) Appl. No.: 12/154,508

(22) Filed: May 23, 2008

(65) Prior Publication Data

US 2008/0275371 A1    Nov. 6, 2008

Related U.S. Application Data

(62) Division of application No. 10/902,122, filed on Jul. 30, 2004, now Pat. No. 7,517,328.

(51) Int. Cl.
*A61H 1/00* (2006.01)

(52) U.S. Cl. ............................................ 601/46; 601/48

(58) Field of Classification Search ............... 601/46, 601/48, 49, 55–56, 77, 148–152
See application file for complete search history.

(56) References Cited

U.S. PATENT DOCUMENTS

| 827,133 A | 7/1906 | Weston |
|---|---|---|
| 1,498,680 A | 6/1924 | Clement et al. |
| 2,181,282 A | 11/1939 | Oster |
| 2,821,191 A | 1/1958 | Pai |
| 3,085,568 A | 4/1963 | Whitesell |
| 3,352,303 A | 11/1967 | Delaney |
| 3,499,436 A | 3/1970 | Balamuth |
| 3,664,331 A | 5/1972 | Filipovici |
| 3,735,755 A | 5/1973 | Eggleton et al. |
| 3,779,249 A | 12/1973 | Semler |
| 3,853,121 A | 12/1974 | Mizrachy et al. |
| 4,079,733 A | 3/1978 | Denton et al. |

(Continued)

FOREIGN PATENT DOCUMENTS

BG        49287        10/1991

(Continued)

OTHER PUBLICATIONS

Birnbaum, et al., "Ultrasound Has Synergistic Effects in Vitro with Tirofiban and Heparin for Thrombus Dissolution", *Thrombosis Research*, 96, (1999), pp. 451-458.

(Continued)

*Primary Examiner* — Michael A. Brown

(57) ABSTRACT

A vibrator for use in enhancement of pre-hospital coronary thrombolysis comprising a vibration source operable to generate vibration at a frequency in the range of 1-1000 Hz with at least a pair of oscillatory contacts spaced to enable simultaneous seating to the anatomic left and right of the sternum (such as to match the geometry of the right and left coronary arteries) of a patient in need of coronary thrombolysis. The preferred vibrator is operable to emit vibration in the low frequency sonic range (at least 20 Hz) with an amplitude of about 1 mm-15 mm (and more preferably greater than 2 mm), such as to provide an effective transthoracic tool for acute coronary thrombolysis applications. In a variation, greater than a pair of contacts are utilized to provide oscillatory contact at differing intercostal space levels (in order to maximize vibratory penetration to the heart which is variably situated depending on the patient's anatomy).

33 Claims, 14 Drawing Sheets

U.S. PATENT DOCUMENTS

| | | | |
|---|---|---|---|
| 4,098,266 A | 7/1978 | Muchisky et al. | |
| 4,216,766 A * | 8/1980 | Duykers et al. | 600/586 |
| 4,232,661 A | 11/1980 | Christensen | |
| 4,269,175 A | 5/1981 | Dillon | |
| RE31,603 E | 6/1984 | Christensen | |
| 4,484,569 A | 11/1984 | Driller et al. | |
| 4,507,816 A | 4/1985 | Smith et al. | |
| 4,538,596 A | 9/1985 | Colasante | |
| 4,651,716 A | 3/1987 | Forester et al. | |
| 4,779,615 A | 10/1988 | Frazier et al. | |
| 4,785,797 A | 11/1988 | Cuervo | |
| 4,791,915 A | 12/1988 | Barsotti et al. | |
| 4,838,263 A | 6/1989 | Warwick et al. | |
| 4,932,414 A | 6/1990 | Coleman et al. | |
| 4,955,365 A | 9/1990 | Fry et al. | |
| 4,966,131 A | 10/1990 | Houghton et al. | |
| 5,005,579 A | 4/1991 | Wurster et al. | |
| 5,040,537 A | 8/1991 | Katakura | |
| 5,065,741 A | 11/1991 | Uchiyama et al. | |
| 5,101,810 A | 4/1992 | Skille et al. | |
| 5,107,837 A | 4/1992 | Ophir et al. | |
| 5,132,942 A | 7/1992 | Cassone | |
| 5,143,070 A | 9/1992 | Ophir et al. | |
| 5,143,073 A | 9/1992 | Dory | |
| 5,150,712 A | 9/1992 | Dory | |
| 5,159,838 A | 11/1992 | Lynnworth | |
| 5,172,692 A | 12/1992 | Kulow et al. | |
| 5,178,147 A | 1/1993 | Ophir et al. | |
| 5,190,766 A | 3/1993 | Ishihara | |
| 5,197,946 A | 3/1993 | Tachibana | |
| 5,207,214 A | 5/1993 | Romano | |
| 5,230,334 A | 7/1993 | Klopotek | |
| 5,243,997 A | 9/1993 | Uflacker et al. | |
| 5,247,937 A | 9/1993 | Ophir et al. | |
| 5,267,223 A | 11/1993 | Flanagan et al. | |
| 5,291,894 A | 3/1994 | Nagy | |
| 5,293,870 A | 3/1994 | Ophir et al. | |
| 5,303,433 A | 4/1994 | Jang | |
| 5,307,816 A | 5/1994 | Hashimoto et al. | |
| 5,391,140 A | 2/1995 | Schaetzle et al. | |
| 5,413,550 A | 5/1995 | Castel | |
| 5,423,862 A | 6/1995 | Clarke et al. | |
| 5,442,710 A | 8/1995 | Komatsu | |
| 5,453,081 A | 9/1995 | Hansen | |
| 5,454,373 A | 10/1995 | Koger et al. | |
| 5,474,070 A | 12/1995 | Ophir et al. | |
| 5,509,896 A | 4/1996 | Carter | |
| 5,520,612 A | 5/1996 | Winder et al. | |
| 5,520,614 A | 5/1996 | McNamara et al. | |
| 5,523,058 A | 6/1996 | Umemura et al. | |
| 5,524,620 A | 6/1996 | Rosenschein | |
| 5,549,119 A | 8/1996 | Solar | |
| 5,555,891 A | 9/1996 | Eisenfeld | |
| 5,556,372 A | 9/1996 | Talish et al. | |
| 5,558,092 A | 9/1996 | Unger et al. | |
| 5,569,170 A | 10/1996 | Hansen | |
| 5,586,346 A | 12/1996 | Stacy et al. | |
| 5,606,754 A | 3/1997 | Hand et al. | |
| 5,613,940 A | 3/1997 | Romano | |
| 5,626,554 A | 5/1997 | Ryaby et al. | |
| 5,674,262 A | 10/1997 | Tumey | |
| 5,676,637 A | 10/1997 | Lee | |
| 5,695,460 A | 12/1997 | Siegel et al. | |
| 5,698,531 A | 12/1997 | Nabel et al. | |
| 5,713,848 A | 2/1998 | Dubrul et al. | |
| 5,720,304 A | 2/1998 | Omura | |
| 5,725,482 A | 3/1998 | Bishop | |
| 5,728,123 A * | 3/1998 | Lemelson et al. | 604/22 |
| 5,762,616 A | 6/1998 | Talish | |
| 5,830,177 A | 11/1998 | Li et al. | |
| 5,861,015 A | 1/1999 | Benja-Athon | |
| 5,873,828 A | 2/1999 | Fujio et al. | |
| 5,879,314 A | 3/1999 | Peterson et al. | |
| 5,913,834 A | 6/1999 | Francais | |
| 5,919,139 A | 7/1999 | Lin | |
| 5,936,163 A | 8/1999 | Greathouse | |
| 5,951,501 A | 9/1999 | Griner | |
| 5,973,999 A | 10/1999 | Naff et al. | |
| 5,983,429 A | 11/1999 | Stacy et al. | |
| 6,027,444 A | 2/2000 | Franck | |
| 6,036,662 A | 3/2000 | Van Brunt et al. | |
| 6,068,596 A | 5/2000 | Weth et al. | |
| 6,082,365 A | 7/2000 | Yenin | |
| 6,093,164 A | 7/2000 | Davis et al. | |
| 6,095,979 A | 8/2000 | Ohtomo | |
| 6,110,098 A | 8/2000 | Renirie et al. | |
| 6,126,619 A | 10/2000 | Peterson et al. | |
| 6,146,342 A | 11/2000 | Glen et al. | |
| 6,155,976 A | 12/2000 | Sackner et al. | |
| 6,193,677 B1 | 2/2001 | Cady | |
| 6,200,259 B1 | 3/2001 | March | |
| 6,254,573 B1 | 7/2001 | Haim et al. | |
| 6,261,537 B1 | 7/2001 | Klaveness et al. | |
| 6,270,459 B1 | 8/2001 | Ophir et al. | |
| 6,273,864 B1 | 8/2001 | Duarte et al. | |
| 6,277,085 B1 | 8/2001 | Flynn | |
| 6,283,935 B1 | 9/2001 | Laufer et al. | |
| 6,287,271 B1 | 9/2001 | Dubrul et al. | |
| 6,296,617 B1 | 10/2001 | Peeler et al. | |
| 6,330,475 B1 | 12/2001 | Renirie et al. | |
| 6,332,872 B1 | 12/2001 | Young | |
| 6,398,772 B1 | 6/2002 | Bond et al. | |
| 6,408,205 B1 | 6/2002 | Renirie et al. | |
| 6,424,864 B1 | 7/2002 | Matsuura | |
| 6,428,477 B1 | 8/2002 | Mason | |
| 6,432,070 B1 | 8/2002 | Talish et al. | |
| 6,432,072 B1 | 8/2002 | Harris et al. | |
| 6,434,539 B1 | 8/2002 | Woodsum et al. | |
| 6,471,663 B1 | 10/2002 | Van Brunt et al. | |
| 6,500,134 B1 | 12/2002 | Cassone | |
| 6,511,429 B1 | 1/2003 | Fatemi et al. | |
| 6,537,236 B2 | 3/2003 | Tucek et al. | |
| 6,579,251 B1 | 6/2003 | Randoll | |
| 6,635,017 B1 | 10/2003 | Moehring et al. | |
| 6,682,496 B1 | 1/2004 | Pivaroff | |
| 6,687,625 B2 | 2/2004 | Ophire et al. | |
| 6,716,184 B2 | 4/2004 | Vaezy et al. | |
| 6,719,694 B2 | 4/2004 | Weng et al. | |
| 6,733,450 B1 * | 5/2004 | Alexandrov et al. | 600/439 |
| 6,936,025 B1 | 8/2005 | Evans et al. | |
| 7,090,300 B2 | 8/2006 | Fujita | |
| 7,229,423 B2 | 6/2007 | Horzewski | |
| 7,232,417 B2 * | 6/2007 | Plante | 601/46 |
| 2002/0016560 A1 | 2/2002 | Hansen | |
| 2002/0049395 A1 | 4/2002 | Thompson et al. | |
| 2002/0055693 A1 | 5/2002 | Thompson et al. | |
| 2002/0072690 A1 | 6/2002 | Thompson et al. | |
| 2002/0072691 A1 | 6/2002 | Thompson et al. | |
| 2002/0082529 A1 | 6/2002 | Suorsa et al. | |
| 2002/0091339 A1 | 7/2002 | Horzewski et al. | |
| 2002/0103454 A1 | 8/2002 | Sackner et al. | |
| 2002/0193833 A1 * | 12/2002 | Dimmer et al. | 607/3 |
| 2003/0009119 A1 | 1/2003 | Kamm | |
| 2003/0028111 A1 | 2/2003 | Vaezy et al. | |
| 2003/0083599 A1 | 5/2003 | Kitov | |
| 2003/0135085 A1 | 7/2003 | Bassuk et al. | |
| 2003/0163067 A1 | 8/2003 | Lidgren | |
| 2003/0181812 A1 | 9/2003 | Rabiner et al. | |
| 2003/0204141 A1 | 10/2003 | Nock et al. | |
| 2003/0236476 A1 | 12/2003 | Inman et al. | |
| 2004/0006288 A1 | 1/2004 | Spector et al. | |
| 2004/0122354 A1 | 6/2004 | Semba et al. | |
| 2004/0133066 A1 | 7/2004 | Mann et al. | |
| 2004/0153009 A1 | 8/2004 | Horzewski et al. | |
| 2004/0173220 A1 | 9/2004 | Harry et al. | |
| 2005/0004460 A1 | 1/2005 | Taylor et al. | |
| 2005/0096669 A1 * | 5/2005 | Rabiner et al. | 606/128 |
| 2005/0148807 A1 | 7/2005 | Salkinder | |
| 2005/0203398 A1 | 9/2005 | Sandrin et al. | |
| 2006/0282026 A1 | 12/2006 | Glen et al. | |
| 2007/0123809 A1 | 5/2007 | Weiss et al. | |
| 2007/0173751 A1 | 7/2007 | Ohashi | |
| 2007/0225618 A1 | 9/2007 | Ward et al. | |
| 2008/0221489 A1 | 9/2008 | Madsen et al. | |

FOREIGN PATENT DOCUMENTS

| | | |
|---|---|---|
| EP | 429 109 | 5/1991 |
| FR | 608893 | 12/1925 |
| FR | 284 3290 | 2/2004 |
| GB | 2167961 | 6/1986 |
| JP | 4156823 | 5/1992 |
| JP | 8089549 | 4/1996 |
| JP | 11192276 | 7/1999 |
| RU | 2187295 C2 | 2/2002 |
| WO | WO 85/03634 | 8/1985 |
| WO | WO 87/05497 | 9/1987 |
| WO | WO 9428873 | 12/1994 |
| WO | WO 95/01770 | 1/1995 |
| WO | WO 96/39955 | 12/1996 |
| WO | WO 97/40806 | 11/1997 |
| WO | WO 00/00155 | 1/2000 |
| WO | WO 00/67693 | 11/2000 |
| WO | WO 02/04070 A1 | 2/2001 |
| WO | WO 02/07582 | 1/2002 |
| WO | WO 02/43645 | 6/2002 |
| WO | WO 02/54018 | 7/2002 |

OTHER PUBLICATIONS

Birnbaum, et al., "Noninvasive In Vivo Clot Dissolution Without a Thrombolytic Drug—Recanalization of Thrombosed Iliofemoral Arteries by Transcutaneous Ultrasound Combined with Intravenous infusion of Microbubbles", *Circulation* 1998, 97, pp. 130-134.

Birnbaum, et al., "Noninvasive Transthoracic Low Frequency Ultrasound Augments Thrombolysis in a Canine Model of Acute Myocardial Infarction—Evaluation of the Extent of ST-Segment Resolution", *Journal of Thrombosis and Thrombolysis* 11(3), pp. 229-234, 2001.

Braaten, et al., "Ultrasound Reversibly Disaggregates Fibrin Fibers", *Thromb Haemost*, 1997, 78, pp. 1063-1068.

Christen, et al., "Effects of Intermittent Pneumatic Compression on Venous Haemodynamics and Fibrinolytic Activity", *Blood Coagulation and Fibrinolysis*, vol. 8, 1997, pp. 185-190.

Comerota, et al., "The Fibrinolytic Effects of Intermittent Pneumatic Compression", *Annals of Surgery*, vol. 226, No. 3, pp. 306-314, 1997.

Farber, et al., "Conduction of Cardiovascular Sound Along Arteries", *Circulation Research*, vol. XII, Mar. 1963, pp. 308-316.

Francis, "Ultrasound-Enhanced Thrombolysis", *Echocardiography: A Jrnl. of CV Ultrasound & Allied Tech.*, vol. 18, No. 3, 2001, pp. 239-246.

Griesinger, et al., "Vibration Induced Current Fields and Cavitational Effect", *Zahnarztliche Praxis*, 1989, vol. 40, No. 6, pp. 213-217.

Hackett, et al., "Intermittent Coronary Occlusion in Acute Myocardial Infarction—Value of Combined Thrombolytic and Vasodilator Therapy", *The New England Journal of Medicine*, vol. 317, No. 17, pp. 1055-1059, 1987.

Honda, et al, "Mathematical Model of the Effects of Mechanical Vibration on Crossbridge Kinetics in Cardiac Muscle", *Jpn Circ J.*, 1994, 58: pp. 416-425.

Hudlicka, et al., "The Effect of Vibration on Blood Flow in Skeletal Muscle in the Rabbit", *Clinical Science and Molecular Medicine*, (1978), 55, pp. 471-476.

Jackson, et al., "Antithrombotic Therapy in Peripheral Arterial Occlusive Disease", *American College of Chest Physicians*, 2001, 119: pp. 283S-299S, http://www.chestjournal.org/cgl/content/full/119/1_suppl/283S.

Kasirajan, et al., "Management of Acute Lower Extremity Ischemia: Treatment Strategies and Outcome", *Current Interventional Cardiology Reports*, 2000, 2, pp. 119-129.

Koiwa, et al., "Measurement of Instantaneous Viscoelastic Properties by Impedance-Frequency Curve of the Ventricle", *Am. J. Physiol.*, 250, (Heart Circ. Physiol. 19), pp. H672-H684, 1986.

Koiwa, et al., "The Improvement of Systolic Function of Depressed Left Ventricle by External Vibration at Diastole", *Tohoku J. Exp. Med.*, 1989, 159, pp. 169-170.

Koiwa, et al., "Diastolic Vibration from the Precordium Increases Coronary Blood Flow in Humans", *J. Cardiovasc Diagn Procedures*, 1994, 12, p. 110, Abstract (FRI-POS 05).

Koiwa, et al., "The Effect of Diastolic Vibration on the Coronary Flow Rate in the Canine Heart With Ischemia", *J. Cardiovasc Diagn Procedures*, 1994, 12, p. 110, Abstract (FRI-POS 07).

Kovak, et al., "Thrombolysis Plus Aortic Counterpulsation: Improved Survival in Patients Who Present to Community Hospitals with Cardiogenic Shock", *J. Am. Coll. Cardiol.*, vol. 29, No. 7, Jun. 1997, pp. 1454-1458.

Lindblad, et al., "Effect of Vibration on a Canine Cutaneous Artery", *Am. J. Physiol.*, 250 (Heart Circ. Physiol. 19), pp. H519-H523, 1986.

Lincoff, et al., "Illusion of Reperfusion—Does Anyone Achieve Optimal Reperfusion During Acute Myocardial Infarction?", *Circulation*, Jun. 1993, 88, pp. 1361-1374.

Ljung, et al., "Inhibition of Vascular Smooth Muscle Contraction by Vibrations", *Abstract Acta Physiol. Scand.*, 396, Suppl., p. 95, 1973.

Ljung, et al., "Vibration-Induced Inhibition of Vascular Smooth Muscle Contraction", *Blood Vessels*, 12, pp. 38-52, 1975.

Luo, et al., "Enhancement of Thrombolysis in Vivo Without Skin and Soft Tissue Damage by Transcutaneous Ultrasound", *Thrombosis Research*, 89, 1998, pp. 171-177.

Luo, et al., "Transcutaneous Ultrasound Augments Lysis of Arterial Thrombi In Vivo", *Circulation*, vol. 94, No. 4, Aug. 1996, pp. 775-778.

Luo, et al., "Effect of External Ultrasound Frequency on Thrombus Disruption in Vitro", *Journal of Thrombosis and Thrombolysis*, 1996, 3, pp. 63-66.

Margulis, et al., "Physicochemical Processes Induced by Low-frequency Acoustic Vibrations in Liquids. I. Growth and Pulsation of Gas Bubbles", *Russian Journal of Physical Chemistry*, 56, 6, 1982, pp. 876-878.

Michalis, et al., "Vibrational Angioplasty and Hydrophilic Guidewires in the Treatment of Chronic Total Coronary Occlusions", *J. Endovasc. Ther.*, 2000, 7, pp. 141-148.

Morgan, et al., "Arterial Flow Enhancement by Impulse Compression", *Vasc. Surg.*, 25, pp. 8-16, Jan./Feb. 1991.

Nyborg, "Ultrasonic Microstreaming and Related Phenomena", *Br. J. Cancer*, 1982, 45, Suppl. V, 156, pp. 156-160.

Oliva, et al., "Arteriographic Evidence of Coronary Arterial Spasm in Acute Myocardial Infarction", *Circulation*, vol. 56, No. 3, Sep. 1977, pp. 366-374.

Olsson, et al., "Enhancement of Thrombolysis by Ultrasound", *Ultrasound in Med. & Biol.*, vol. 20, No. 4, pp. 375-382, 1994.

Ramcharan, et al., "The Effects of Vibration Upon Blood-Viscosity and Red-Cell Mobility: A Study of In Vivo and In Vitro", *Biorheology*, 19, pp. 341-352, 1982.

Riggs, et al., "Ultrasound Enhancement of Rabbit Femoral Artery Thrombolysis", *Cardiovascular Surgery*, vol. 5, No. 2, pp. 201-207, 1997.

Rosenschein, et al., "Experimental Ultrasonic Angioplasty: Disruption of Atherosclerotic Plaques and Thrombi in Vitro and Arterial Recanalization in Vivo", *J Am. Coll. Cardiol.*, vol. 15, No. 3, Mar. 1, 1990, pp. 711-717.

Rosenschein, et al., "Shock Wave Thrombus Ablation, a New Method for Noninvasive Mechanical Thrombolysis", *The American Journal of Cardiology*, vol. 70, Nov. 15, 1992, pp. 1358-1361.

Sanborn, et al., "Impact of Thrombolysis, Intra-aortic Balloon Pump Counterpulsation, and Their Combination in Cardiogenic Shock Complicating Acute Myocardial Infarction: A Report from the SHOCK Trial Registry", *Journal of American College of Cardiology*, vol. 36, No. 3, Suppl. A., Sep. 2000, pp. 1123-1129.

Serikova, et al., "Effect of General Low-Frequency Vibration on the Functional State of the Blood", *Voenno-Meditsinskii Zhurnal*, 1977, pp. 59-62.

Siegel, et al., "Noninvasive, Transthoracic, Low-Frequency Ultrasound Augments Thrombolysis in a Canine Model of Acute Myocardial Infarction". *Circulation*, May 2, 2000, 101, pp. 2026-2029.

Silver, et al., "The Relationship Between Acute Occlusive Coronary Thrombi and Myocardial Infarction Studied in 100 Consecutive Patients", *Circulation*, 61, No. 2, 1980, pp. 219-227.

Smith, et al., "Mechanical Vibration Transmission Characteristics of the Left Ventricle: Implications with Regard to Auscultation and Phonocardiography", *J. Am. Coll. Cardiol.*, vol. 4, No. 3, Sep. 1984, pp. 517-521.

Stone, et al., "Normal Flow (TIMI-3) Before Mechanical Reperfusion Therapy is an Independent Determinant of Survival in Acute Myocardial Infarction—Analysis from the Primary Angioplasty in Myocardial Infarction Trials", Circulation, Aug. 7, 2001, 104, pp. 636-641.

Suchkova, et al., "Enhancement of Fibrinolysis With 40-kHz Ultrasound", Circulation, 1998, 98, pp. 1030-1035.

Takashima, et al., "Effects of Mechanical Force on Blood Fibrinolytic Activity", Thrombosis and Haemostasis, 58, 1987, Abstract.

Tarnay, et al., "Pneumatic Calf Compression, Fibrinolysis, and the Prevention of Deep Venous Thrombosis", Surgery, Oct. 1980, pp. 489-496.

Templeton, et al., "Influence of Acute Myocardial Depression on Left Ventricular Stiffness and Its Elastic and Viscous Components", The Journal of Clinical Investigation, vol. 56, Aug. 1975, pp. 278-285.

Tiffany, et al., "Bolus Thrombolytic Infusions During CPR for Patients with Refractory Arrest Rhythms: Outcome of a Case Series", Annals of Emergency Medicine, 31:1, Jan. 1998, pp. 124-126.

Wobser, et al., "Intragastral Disintegration of Blood Coagula by Mechanical Vibration", Endoscopy, 10, 1978, pp. 15-19.

[No authors listed] Working Party on Thrombolysis in the Management of Limb Ischemia, "Thrombolysis in the Management of Lower Limb Peripheral Arterial Occlusion—A Consensus Document", J. Vasc. Interv. Radiol., 2003, pp. S337-S349.

Yock, et al, "Catheter-Based Ultrasound Thrombolysis—Shake, Rattle and Reperfuse", Circulation, 1997, 95, pp. 1360-1362.

Zalter, et al., "Acoustic Transmission Characteristics of the Thorax", J. Appl. Physiol., 1963, 18, pp. 428-436.

Ng, K. et al., "Therapeutic Ultrasound: Its Application in Drug Delivery", Medicinal Research Reviews, vol. 22, No. 2, pp. 204-223, 2002.

Tachibana, K. et al., "The Use of Ultrasound for Drug Delivery", Echocardiography, vol. 18, No. 4, pp. 323-328, May 2001.

Hull, W. et al., "Heat-Enhanced Transdermal Drug Delivery. A Survey Paper", The Journal of Applied Research, vol. 2, No. 1, Winter 2002.

Rapoport, N., International Cancer Research Portfolio Abstract,—award funding period Jan. 15, 1999-Dec. 31, 2002, Award code CA076562.

Cho, C-W, et al., "Ultrasound Induced Mild Hyperthermia as a Novel Approach to Increase Drug Uptake in Brain Microvessel Endothelial Cells", Pharm. Res. Aug. 2002, 19(8)1123-9.

Folts, D., "An In Vivo Model of Experimental Arterial Stenosis, Intimal Damage, and Periodic Thrombosis", Circ. 1991, 83 supp. IV:pp. IV-3 IV-14.

Folts, D., "Folts Cyclic Flow Animal Model", Contemporary Cardiology, Vascular Disease and Injury Preclinical Research, pp. 127-145, Humana Press Inc., Nov. 9, 2000.

Google Web Address: "Good Vibrations Personal Energiser—Vitafon—IR", Title: "Vitafon—IR for the temporary relief of pain". Google cache retrieval date, Apr. 29, 2006.

Kurtus, R: Google Address: "Hearing Pitch or Sound Frequencies—Succeed Through Using your Senses". Title: "Hearing Pitch Sound Frequencies", Mar. 7, 2001.

Google Web Address: "Frequency Hearing Ranges in Dogs and other Species", Title: "How well do dogs and other animals hear?", Google cache retrieval date Jun. 12, 2006.

Siegel R.J., "Ultrasound augmentation of thrombolysis and tissue perfusion", Clin. Physiol. Funct. Imaging, 2004, 24, pp. 156-163.

Coleman et al., "Therapeutic Ultrasound in the Production of Ocular Lesions", American Journal of Ophthal., vol. 86, No. 2, 1978, pp. 185-192.

Coleman et al., "Application of therapeutic Ultrasound in Ophthalmology", Progress in Medical Ultrasound, 1981, pp. 263-270.

Blinc, et al., "Characterization of Ultrasound-Potentiated Fibrinolysis In Vitro", Blood, vol. 81, No. 10 (May 15, 1993), pp. 2636-2643.

Dalen, et al., "Coronary Spasm, Coronary Thrombosis, and Myocardial Infarction: A Hypothesis Concerning the Pathophysiology of Acute Myocardial Infarction", American Heart Journal, vol. 104, No. 5, Part 1, Nov. 1982, pp. 1119-1124.

Francis, et al., "Ultrasound Accelerates Transport of Recombinant Tissue Plasminogen Activator Into Clots", Ultrasound in Med. & Biol., vol. 21, No. 3, pp. 419-424, 1995.

Maseri, et al., "Coronary Vasospasm as a Possible Cause of Myocardial Infarction", The New England Journal of Medicine, vol. 299, No. 23, pp. 1271-1277, Dec. 1978.

Rosenschein, et al., "Shock-Wave Thrombus Ablation, a New Method for Noninvasive Mechanical Thrombolysis". The American Journal of Cardiology, vol. 70, Nov. 15, 1992, pp. 1358-1361.

Takagi, et al., "Diastolic Vibration Improves Systolic Function in Cases of Incomplete Relaxation", Circulation, vol. 86, No. 6, Dec. 1992, pp. 1955-1964.

Matsuda, T et al, Extracorporeal Cardiac Shock Wave Therapy Markadly Ameliorates Ischemia-Induced Mycardial Dysfunction in Pigs In Vivo, Circulation 2004; 110; 3055-3061.

Gutersohn, A et al, "Shock waves upregulate vascular endothelial growth factor m-RNA in human umbilical vascular endothelial cells." Circulation 2000: 102 (suppl): 18.

Fisher, AB et al, Endothelial cellular response to altered shear stress. Am J Physiol. 2001; 281:L529-L533.

Wang, CJ et al, "Shock wave-enhanced neovascularisation at the tendon-bone junction: an experiment in dogs." J Foot Ankle Surg. 2002;41:16-22.

Gutersohn, A et. al, "Non Invasive Cardiac Angiogenesis shock wave therapy (Ni-CATh) increased perfusion and exercise tolerance in endstage CAD patients." submitted WCC 2006.

Adams et al, "Periodic acceleration: effects on vasoactive, fibrinolytic, and coagulation factors." J Appl Physiol 98: 1083-1090, 2005.

Hudlicka, O et al, "Angiogenesis in skeletal and cardiac muscle." Physiol Rev 72: 369-417, 1992. pp. 377-378; 379-380; 383; 397-399; and 400-402.

Amaral S et al. "Angiotensin II and VEGF—are Involved in angiogenesis induced by short-term exercise training." Am J. Phys Heart Circ 281 (3):H1163-H1169, Sep. 2001.

Suhr, "Effects of Short-term Vibration and Hypoxie during High-Intensity Cycling Exercise on Circulating Levels of Angiogenic Regulatore in Humans" J App. Physiol Apr. 2007.

Malek et al, "Fluid shear stress differentially modulates expression of genes encoding basic fibroblast growth factor . . . " J Clin. Invest. 92: 2013-2021, 1993.

Mitsumata et al. "Fluid shear stress stimulates platelet-derived growth factor expression in endothelial cells." Am J. Physiol. 265 (1):H3-H8, Jul. 1993.

Sumpio "Hemodynamic forces and the biology of the endothelium: signal transduction pathways in endothelial cells subjected to physical forces," J Vasc Surg 13(5):744-6 May 1991.

Ichioka et al "Effects of shear stress on wound-healing angiogenesis in the rabbit ear chamber." J of Surg. Res. 72:29-35, 1997.

Pipp, F et al "Elevated Fluid Shear Stress Enhances Postocclusive Collateral Artery Growth and Gene Expression in Pig Hind Limb," Art Thromb Vasc Biol 2004;24;1664.

Zou, J et al "Vibration induced hearing loss in guinea pig cochlea: expression of TNF-alpha and VEGF," Hearing Research vol. 202, Apr. 1-2, 2005, pp. 13-20.

Davies, P "Turbulent fluid shear stress induces vascular endothelial cell turnover in vitro." Proc. Natl. Acad. Sci. USA vol. 63, pp. 2114-2117, Apr. 1986 Cell Biology.

Krishan, L "Effect of mechanical boundary conditions on orientation of angiogenic microvessels." Cardiovasc. Research 2008 78 (2):324-332.

Lacolley, "Mechanical influence of cyclic stretch on vascular endothelial cells." Card. Vasc. Research 64 (2004) 577-579.

Von Offenberg Sweeney et al, "Cyclic strain-mediated regulation of endothelial matrix metalloproteinase-2 expression and activity." Card Vesc Res. 2004 83(4): 525-534 Abstract.

Von Offenberg Sweeney et al,"Cylcic strain mediated regulation of vascular endothelial cell migration and tube formation." Bioch Biophys Res Comm 328(2)2005 572-582 Abstract.

Wilson, E et al, "Mechanical Stain Induces Growth of Vascular Smooth Muscle Cells via Autocrine Action of PDGF." J Cell Bio. vol. 123, 1993 pp. 741-747.

Antic S. et al, Music as an Auditory Stimulus in Stroke Patients, Coll Antropol., vol. 32, Feb. 2008 Suppl 1: pp. 19-23.

Chiu, W et al, Prolonged Stimulation with Sound Increases Angiogenesis . . . Abstract 1361—Feb. 24, 2004 Pub online http://www.aro.org/archives/2004/2004_1361.html.

Koiwa Y, Precordial or Epicardial Input of Phase-Controlled minute vibration: effect coronary flow rate in regional ischemia, New Horiz Fail. Heart Syndrome, 1996; 117-130.

Message Chairs.Co.uk. Advertisement on Internet. http://www.message-chairs.co.uk/understanding_message_chairs.htm.

* cited by examiner

VIBRATOR WITH A PLURALITY OF CONTACT NODES FOR TREATMENT OF MYOCARDIAL ISCHEMIA

CLAIM OF PRIORITY

The present application is a divisional of U.S. patent application Ser. No. 10/902,122, filed on Jul. 30, 2004 now U.S. Pat. No. 7,517,328, which claims priority to Canadian Patent Application No. 2439667 A1 filed Sep. 4, 2003. The contents of these applications are incorporated herein by reference in their entirety.

FIELD OF THE INVENTION

This invention relates to noninvasive medical systems for imparting transcutaneously applied low frequency mechanical vibrational energy to the human body, to improve first line emergency treatment of acute thrombotic vascular obstructions. More particularly, this invention relates to non-invasive drug delivery systems to improve delivery of systemically administered clot disrupting and vasodilatory medications to acutely obstructed blood vessels.

BACKGROUND OF THE INVENTION

Acute vascular obstructions, ischemia and infarction are common medical concerns. Acute Myocardial Infarction ("AMI") subsequent to coronary thromboses in particular is one of the leading causes of death in North America. Current first line treatment of thromboses in the acute phase when the patient reaches professional care is typically by intravenous introduction of thrombolytics, or a combination of drugs such as heparin, aspirin and/or GP 2b 3a platelet inhibitors to dissolve the blood clot. Intravenous and oral nitrates may also be introduced in order to dilate the culprit coronary or other vessel, which usually has a degree of spasm associated.

Thrombolytic drug treatment does not, however, have a high success rate. The success of systemically delivered IV drug therapy in increasing reperfusion rates in the treatment of ST elevation AMI is discussed in the following publications:

1.) American Heart Association, Satellite Symposium 73rd Scientific Session, St. Michael's Review, New Orleans, La.; Nov. 11, 2000.

2.) Francis W M.D., "Ultrasound—Enhanced Thrombolysis." Echocardiography: A. Jrnl. of CV Ultrasound & Allied Tech. Vol. 18, No. 3, 2001. pp 239-246.

3.) Sanborn T et al., "Impact of Thrombolysis Intra-aortic Balloon Pump Counter pulsation and their Combination in Cardiogenic Shock Complicating Acute Myocardial Infarction.", SHOCK REGISTRY JACC, 36 (3) Suppl. A. 2000, 1123-9.

The American Heart Association, Satellite Symposium 73rd Scientific Session, St. Michael's Review reported reperfusion rates (i.e. TIMI 3 flow @ 60-90 minutes) with standard thrombolytic therapy varying between 50 and 63%.

Francis reported that lytic therapy fails to achieve any reperfusion (at all) in up to 20% of patients.

Success with drug based reperfusion treatment and in-hospital survival declines markedly when the patient becomes hemodynamically unstable or enters cardiogenic shock, which is the leading cause of in-hospital deaths from MI in North America. Sanborn et al. report 63% in-hospital mortality despite the use of thrombolytic therapy.

In the case of ST elevation Acute Myocardial Infarction, when noninvasive drug treatment (i.e. systemically introduced IV thrombolysis) to achieve reperfusion fails, invasive catheter based techniques such as Percutaneous Coronary Intervention ("PCI") are employed. Sometimes, PCI is chosen as a direct measure, whereby a coordination of the immediate use of lytics or other agents may be first established in the field while en route to a cardiac catheterization laboratory where intervention can be performed. A disadvantage of invasive treatment for acute thrombotic obstructions (while very successful) is the infrastructure required, particularly the cardiac "cathlab" requiring substantial equipment and staff. Such infrastructure is not readily accessible in hospitals world wide, and even when available, there is a significant time requirement to coordinate and set up equipment and personnel. Due to the lack of immediate availability of cathlabs, patients, often unstable, must be transported and/or wait for the cathlab team to assemble. These difficulties result in a delay in treatment increasing myocardial necrosis, and reducing the likelihood of a successful and timely reperfusion.

Treatment systems utilizing noninvasive vibration in the low frequency ultrasonic range ("LFUS" e.g. 20 kHz-100 kHz) have been employed as an adjunct to systemically delivered IV thrombolysis including coronary thrombolysis, in attempting to overcome these disadvantages. The LFUS wave form provides mechanical agitation via cavitation and acoustic streaming to the blood within the culprit vasculature wherein a blood clot resides, thereby encouraging disruption of the clot and increased permeation of the drug into the clot to accelerate reperfusion.

LFUS to disrupt thromboses and assist thrombolysis, has however, only shown effectiveness in research applications (i.e. animal studies), for the treatment of relatively superficial thromboses, where the exact, fixed location of the blood clot was already known to the investigator. LFUS wave forms (which deliver low amplitude micro displacements which are imperceptible to a patient) offer no assurance of therapeutic ultrasonic penetration to reach a blood clot within a human body in a practical application, without, for example, the establishment of a viable acoustic energy delivery window and targeting via direction of an application probe (i.e. as in ultrasonographic imaging), which takes intelligible application of force and angulation of the probe against a patient's skin via a skilled operator. The subsequent resultant need for high skill to direct a LFUS application makes such a therapy a poor candidate for emergency cases where a skilled treatment operator would rarely be available. A non-directed LFUS treatment (without a skilled imaging approach) in particular, Is poorly suited towards human coronary applications as the human heart is a relatively deep structure, is located variably within the thoracic cavity, and the blood clot is a hidden, moving target located beneath highly attenuating anatomic structures such as lung, fat and dense intercostal muscle which does not transmit ultrasound.

Thompson, T. et al in U.S. patent application No. 20020049395-2002, disclose the emergency application of a non-directed LFUS treatment in conjunction with thrombolytic therapy in response to Acute MI in humans, wherein LFUS is delivered in a nonspecific manner to a patients skin surface through a liquid cooling medium without intelligible placement and direction of the ultrasonic source through a confirmed ultrasonic penetrating window. As stated this method is sub-optimal as it does not insure adequate penetration of the therapeutic signal, and no proof is provided that this style of technique will show a clinical benefit in humans. Further examples of this kind of noninvasive LFUS treatment for vascular thromboses are disclosed in U.S. Pat. Nos. 6,126,619, 5,713,831, 5,879,314, 6,126,619, and 6,398,772; as well as in U.S. patent application Nos. 20020082529, 20020107473, 20020072691, 20020055693, 200200726690 and 20020091339.

Non-invasively delivered ultrasonic treatment systems directed by skilled medical imaging techniques to disrupt an undesirable target (including thromboses), have been disclosed in numerous articles and publications.

Carter and Siegel in U.S. Pat. Nos. 5,509,896 and 5,695,460 respectively, disclose an externally applied LFUS treatment probe placed in direct contact with a patient's skin (with optional means to enable "directing" or "focusing" of the LFUS wave form towards the area or volume targeted) to improve emergency thrombolysis, including coronary thrombolysis. A thrombolytic agent and/or cavitating micro bubble solution is preferably introduced by a catheter placed "proximate" the site of the vascular obstruction, to ensure effectiveness of the treatment system. The requirement of high skill (both in directing the treatment probe, and in the invasive procedure of introducing a catheter) is not ideal (nor preferable) for first line therapy applications in the field or in the emergency room. Furthermore the probe contact will typically overheat and cause burning of the patient's skin.

Lithotriptic style techniques such as in U.S. Pat. Nos. 5,065,741, 5,207,214, 5,524,620, 5,613,940, 5,725,482, 6,068,596 and U.S. patent application Ser. No. 2004/0006288 A1 (which employ use of externally imparted focused ultrasonic waves or ultrasonic shock waves directed by an imaging modality to disrupt an internal target including thromboses) have also been disclosed. This style of therapy (while common in the treatment of kidney stones and the like) has not gained acceptance in the emergency treatment of acute vascular obstructions or thrombotic obstructions, probably because thrombotic lesions are difficult (if not impossible) to conveniently image, and these style of applications are inexpedient for use as they require advanced training, a controlled environment, calculations, and specialized equipment to employ. Furthermore, lithotriptic systems and other focused wave therapy techniques are generally limited to treatment of stationary targets within the human body, hence applications to the coronary arteries (such as in the acute treatment of coronary thrombotic lesions) cannot prospectively be performed.

Low frequency mechanical vibration treatment systems have been considered in the invasive treatment of thrombotic obstructions via catheter based techniques. U.S. Pat. No. 6,287,271 to Dubrul et al., for example, discloses a low-frequency (1-1000 Hz) vibrating catheter drug delivery system resulting in 68% lysing when placed proximally to an artificial clot in a test tube with the drug Urokinase, versus 4.5% lysing with Urokinase treatment alone. As stated above, this system is invasive, and thereby requiring great specialized skill and equipment to introduce a catheter directly to the thrombosis site, and thus has no utility as a first line measure in the field or in emergency room cases.

Generally non-invasively delivered low frequency vibration or percussion in the sonic to infrasonic ranges has received little focus in the field of treatment of acute vascular obstructions, ischemic events or blood flow disturbances.

Cardio Pulmonary Resuscitation ("CPR"), which is essentially high displacement amplitude compressional wave energy of 1.5 Hz (i.e. very low frequency vibration), was paired used successfully in conjunction with coronary thrombolysis in cases of known acute myocardial infarction which had deteriorated and a poor outcome was otherwise imminent. These cases were reported by Tiffany et al. in "Bolus Thrombolytic Infusions During CPR for Patients With Refractory Arrest Rhythms: Outcome of a Case Series" (Annals of Emergency Medicine, 31:1, January 1998, 134-136). This medical method, which was designed to sustain the life of the patient conjointly with the deliverance of thrombolysis (and not to act as an adjunct to thrombolysis per se), is limited to cardiac arrest situations, and the manual nature of the application of high displacement amplitude, mechanical energy by human hand would be labor intensive, potentially tiresome to an operator, and would eventually cause undue harm to a patient if delivered for sustained periods.

Wobser, E et al. in an article "Intragastral Disintegration of Blood Coagula by Mechanical Vibration" in Endoscopy 10, 1978, 15-19; discloses a 50-500 Hz "flexural electromagnetic resonator" for insertion into the stomach for disruption of "big blood coagula" in order to facilitate endoscopic examination in GI bleeds. Furthermore, Lee in U.S. Pat. No. 5,676,637 discloses a low frequency vibratory probe for insertion in the anus to dissolve venous thromboses to improve blood circulation in the treatment of hemorrhoids. Neither system is directed towards treatment of acute vascular blockages or emergency blood flow disturbances, and neither instrument is configured to enable effective penetration through a significantly attenuating barrier such as the chest wall or other external body surface.

Matsuura in U.S. Pat. No. 6,424,864 B1 discloses an all purpose wave therapy system (i.e. applying electric, electromagnetic and/or acoustic waves) for treatment of a plurality of ailments ranging from depression, to rheumatism, to infertility, to poor blood circulation in the hands and feet. In one disclosed embodiment, sound waves generated through one of a sonic platform apparatus or set of head phones enables acoustic therapy to the body (or "cuticle", or "ears") of a user in contact with the apparatus. The '864 patent describes a low intensity, dissipated therapeutic system of acoustic and electromagnetic wave transmission to a user, and is thereby not suitable to emergency disruptive and agitative applications wherein the importation of highly concentrated external percussive force to predetermined or selected application sites is required to ensure therapeutic penetration and effectiveness. Furthermore, this system is not prescribed towards the treatment of acute vascular obstructions or ischemic events, hence there are no methods by which these particular applications could be performed.

Randoll in U.S. Pat. No. 6,579,251 B1 discloses a low frequency oscillatory device for the treatment of a plurality of ailments including "micro circulation disorders", employing a rotating eccentrically mounted treatment head which effectively delivers (when rotating) oscillatory skin displacements of between 4 to 7 mm at a frequency of 5-25 Hz to its user. The '251 patent mimics patient "tremors" to drive sequestered fluids through the valved systems of the veins and lymphatics to clear tissue spaces. Such rotating head devices are not designed nor intended for the emergency treatment of acute blood flow disturbances, and are energy inefficient as the forces of vibration are directed tangentially to the skin surface.

Endo, Y in GB2167961 discloses a bed (or mattress) sheet with a plurality of vibrating members to be applied to the body surface of a user while sleeping, for several uses ranging from reduced "sleep latency" to the prevention of "interruption in blood circulation". The '961 patent Is not directed to emergency applications or response to ischemic events, and the vibration disclosed is ineffectual as it is of low amplitude and cannot be concentrated to a particular body part afflicted.

Cossone, A. et al. in PCT Appl. WO 02/0782 A2, and U.S. Pat. No. 6,500,134 B1 discloses a water-bath vibrating palliative, therapeutic system, with an optimal frequency of 600 Hz to generally improve coronary artery circulation in chronic cases. This water bath method is not designed (and is impractical) for use in the field and prospectively for heart attack or acute cases, and the water to skin vibrational coupling is energy transmission inefficient, of low amplitude, and does not enable focusing of treatment to key area's upon the chest wall or other body part which would confer maximum benefit.

Nagy in European Patent Appl. No. 0429109 B1 and U.S. Pat. No. 5,291,894 discloses a loud speaker system operational to generate acoustic waves (i.e. sound waves through air) in the 1-1000 Hz and 20 Hz-20 kHz range respectively, for the chronic degenerative treatment of vasoconstrictions resulting in poor circulation and stasis to the limbs of a patient. Nagy also names, in short, the optional use of a "piezoelectric element" which may alternatively be placed in direct contact against the body part treated. Sound waves through air are a highly inefficient means for delivering mechanical energy to the human body (i.e. the forces produced to the skin surface treated would be negligible), and there is no proof provided that this style of therapy would assist blood circulation in acute or chronic cases. Similarly "piezoelectric elements" (which are generally used to emit micro displacements in the ultrasonic ranges), are not operable to independently generate high displacements under load (i.e. in the low frequency ranges), hence cannot supply (prospectively) the agitative percussive force or mechanical energy required to ensure therapeutic penetration and effective treatment in emergency thrombotic applications which are often deeply situated.

Sackner in U.S. patent application No. 20020103454 discloses a "vibrating" "reciprocating movement platform" or bed which oscillates in a to and fro motion (i.e. in the head to foot direction), delivering "external pulses" to a human body in the frequency range of 0.25-6 Hz, for a plurality of applications including improving blood circulation in chronic and acute cases. The '454 patent application invokes hemodynamic forces or "pulses" by virtue of the accelerations and deceleration's of the movement platform which purportedly instill sheer stresses from blood to endothelium of the vasculature, which is known to invoke the liberation of endogenous "beneficial mediators" such as t-PA, EDRF, and Nitric Oxide (all of which are of assistance in the improvement of blood flow and prophylaxis to disease). Whole body "vibration" methods such as Sackner describes are not well suited for treatment of acute thrombotic lesions or emergency blood flow disturbances as relatively small (or insignificant) localized forces to the targeted vascular regions themselves are generated. Furthermore, the oscillations emitted are lower than the resonance frequency of the heart within the thoracic cavity, hence the vibratory effect to the heart (and coronaries) would be even further diminished in cardiac applications. Finally the treatment method invariably also shakes the patient's head which is potentially dangerous and inappropriate if the treatment system where ever to be used conjointly with thrombolytic therapy.

Jap. Pat. No. JP 8,089,549 ("549") to Koiwa and Honda discloses a noninvasive 50 Hz diastolic timed chest wall vibrator treatment system via a singular mechanical probe to skin coupling interface to treat cardiac ischemia. The '549 patent increases coronary blood flow to stable patients with known coronary artery narrowings, through a prescribed method of applying vibration specifically timed to the diastolic phase of the cardiac cycle via a hand held unit applied to the chest wall in a low amplitude, comfortable manner (i.e. such that the patient "experiences no pain"). Koiwa teaches that diastolic timed vibration relaxes the myocardium (which is particularly stiff in ischemic states), allowing it to perfuse more efficiently and thereby assist blood perfusion to the ischemic heart.

The '549 patent is not directed to the treatment of emergent coronary incidents or acute thrombotic events, hence there are inherent limitations to the disclosed system. For example, the disclosed single probe to skin coupling is a sub-optimal means of vibration to chest wall transmission and penetration, there is no provision for the delivery of vibration at high amplitude to ensure therapeutic penetration (without for example a skilled imaging or monitoring system), and the timed application of vibration limits its effectiveness as there is no vibration during systole. The comfort level of the patient, and timing of vibration specific to diastole, is of lesser importance (and in fact limiting) when the key point of the therapy is to agitate and disrupt a thrombus, as well as to encourage the mixing of drugs into the thrombus. Furthermore, complex monitoring and processing means via an electrocardiographic trigger are required to effect cardiac phase controlled varying vibration, thus the treatment system is somewhat awkward and difficult to use prospectively in emergency cases.

Low frequency vibrators or percussive devices of high power and displacement enablement are well known (e.g. for massage and mobilization of pulmonary congestions), but have found no utility in the treatment of acute vascular obstructions or response to ischemic events. These devices (such as the Mini Pro 2 Thumper™, Homedics Professional Percussion Massager, and the "Deep muscle stimulator device" disclosed in U.S. Pat. No. 6,682,496), while of potential employment to the current specification, are not ideal as they are equipped with one, non-adjustable high displacement amplitude setting, so their vibrations may be either too strong or too weak depending on the body surface and tolerance level of the patient treated. Also, such devices are known to quickly overheat and dampen oscillations when placed under load, which greatly diminishes their overall penetration power and application time.

Vibration devices with incrementally selectable force or power control (i.e. at a given frequency) have been generally described for a variety of medical uses ranging from penile stimulation (U.S. Pat. No. 6,027,444), gum massage (U.S. Pat. No. 3,664,331), fingertip massage (U.S. Pat. Nos. 2,181, 282, 1,498,680), assisting the diffusion of hair solutions into the scalp of a user (U.S. Pat. No. 5,830,177), eliminating mucus from the lung (U.S. Pat. No. 5,453,081), and for treatment of scoliosis of the spine (U.S. Pat. No. 6,082,365). These devices have not been optimally combined however, with a high powered vibration source (i.e. one adapted to emit a high displacement amplitude while under load) and an optimized attachment interface (i.e. enabling concentrated delivery of vibration localized to a selected body surface), to enable an effective, penetrative vibration delivery system suitable for treatment of acute vascular obstructions, which are often deeply situated within the human body.

Harris et al. in U.S. patent application Ser. No. 2002/0161315 A1 discloses a low frequency hand held percussive massager of indeterminate power (which purportedly enables at least marginal levels of force or intensity emission control), comprising a first vibratory massage element mounted to one side of the massage body and a pair of percussive "nodes" mounted to the opposite side. While of potential use to the current specification, the disclosed massager is not ideal as the placement and necessary operation of a vibratory element in diametric opposition to the percussive nodes is energy inefficient, and is inexpedient for use as it makes the device difficult to apply with significant engagement force by the hands of an operator. Furthermore the disclosed massager does not allow for the particular selection of variable stroke length or waveshape control, which may be advantageous in a controlled research or clinical setting wherein definable, variable, and reproducible percussive stimuli may be desired.

High powered low frequency oscillation devices operable under load with moduable vibratory wave forms (including selectable intensity and even wave shape) are known to industry, but have found no common use in direct human contact for application to selected body surfaces, hence the oscillations imparted would be either indirect and dissipated, or fundamentally unsafe to apply. Examples of such vibration sources consist of: Aura Bass Shakers, Clark Synthesis Tactile Sound Transducers, industrial linear motors, speakers (i.e. voice coils—"woofers"), and pile drivers.

There has also been little focus In the area of directing or confirming the penetration levels of low frequency vibration (or percussion) to an invasively located target in a patient, via an imaging or monitoring technique.

Japanese Pat. No. JP 4156823 to Takishima et al. discloses a miniaturized accelerometer disposed on a transesophageal lead for monitoring penetration levels of externally imparted cardiac phased modulated vibration to the heart, to facilitate the diagnosis and treatment of heart failure. The requirement of an invasive step of introducing a transesophageal probe to enable vibration monitoring and targeting is not ideal (nor preferred) in emergency settings.

U.S. Pat. No. 6,068,596 to Weth et al. discloses an ultrasonic shock wave emission device coupled to an ultrasonic imaging probe to focus and direct ultrasonic shock waves to internalized neural clusters in chronic pain management. The '596 patent is not directed towards treatment of thromboses or acute vascular obstructions, and the resulting "pulsed" waves (which are only emitted once every couple of minutes) are in the ultrasonic range hence are of low amplitude and must be focused to yield a significant internal effect. Furthermore the ultrasonic imaging probe is not utilized to emit the therapeutic ultrasonic shock waves, hence an optimal acoustic (or penetration) delivery window through the overlying body surface is not established.

U.S. Pat. No. 5,919,139 to Lin discloses a low amplitude (designed for "gentle percussive hitting or vibrating") sonic vibration source mounted side by side to an ultrasonic imaging transducer for diagnostic purposes, which enables visualization of the invasive target vibrated. This device is not designed for therapy, and is inexpedient for use (prospectively) in the location and disruption of tissue targets, as the sonic vibration source is not advantageously placed in the same position as the ultrasonic imaging probe upon the body surface, such as to conveniently enable an operator direct visualization and targeting of vibration through an optimized sonic penetration window proximate the vascular target.

As can be seen from above, there is an ongoing need to optimize a noninvasive system for the treatment of vascular ischemia and infarction by drug therapy and/or transcutaneously delivered mechanically therapeutic techniques. The prior art has failed to provide a simple to use, noninvasive mechanical method and apparatus that reliably ensures sufficient penetration to the culprit vessels and sites of vascular thromboses (in particular to the deeply situated vessels within the thoracic cavity such as the coronary arteries) to ensure an adequate agitative and disruptive therapeutic effect in emergency cases. Furthermore, none of the prior arts have successfully integrated a systemically delivered drug therapy system, and/or the optional use of a practical noninvasive imaging system for targeting therapy, to optimally enable such an apparatus.

There is accordingly a need for an effective and easy to apply emergency response system in the application of noninvasive, therapeutic mechanical energy to the human body for the treatment of acute vascular obstructions. The system should be optionally portable to enable reaching a victim in the field, employable with drugs, and preferably adaptable to suit the expertise of an operator (i.e. with the optional incorporation of a practical and convenient imaging system) whose skill level and experience (and thereby preferred clinical approach) may vary markedly.

SUMMARY OF THE INVENTION

The present invention relates to a first line emergency response system for the treatment of acute thrombotic and/or vasospastic vascular obstructions via the noninvasive, high amplitude application of low frequency vibration in the 1-1000 Hz range. The emergency response system optimally utilizes vibration as an adjunct to systemically administered drug therapy. The present invention is based on the intuition that external, transcutaneously imparted low frequency vibration at a high force or displacement amplitude can penetrate deeply within the human body and into the vasculature, without a requirement of undue skill (or imaging techniques), and provide a mechanical disruption of thromboses and synergistic support to systemically delivered drug therapy to improve localized drug effectiveness.

The preferred embodiment relates to an emergency response system employing a low frequency vibration blood perfusion apparatus designed to facilitate and improve the emergency treatment of acute ST elevation myocardial infarction, by externally imparting high amplitude sonic to infrasonic mechanical energy to the chest wall of a patient as an adjunct to systemically delivered thrombolytic therapy, (and/or any other form of drug therapy). A noninvasive vibrator comprising a vibration source with an attachment interface (to enhance transmission and/or effectiveness of emitted vibration), enables high amplitude low frequency external vibration to optimally penetrate to the heart, without the requirement of a skilled imaging technique, and thereby synergistically facilitate the action of systemically directed drug therapy by providing an agitative response to the culprit coronary circulation. Agitation of the epimyocardium by vibration stimuli, and hence the coronary arteries, will improve (by way of sonic streaming, sheer forces and cavitation) the mixing of systemically introduced drugs down an otherwise zero flow, or low flow vascular system. Mechanically delivered vibration further induces disruption of clots which leads to increased permeation of drugs into the clots, and also low frequency vibration independently results in a localized coronary vasodilatory response to the culprit circulation which often has a degree of spasm associated.

A practical emergency response system employing a high powered external low frequency mechanical vibrator, optimally employable in conjunction with systemically delivered drug therapy and operational in the low frequency ranges (i.e. <=1000 Hz range), which is specifically designed and suited to assist the localized process of coronary thrombotic disruption and thrombolysis (and relief of coronary spasm if associated) in the particular emergency treatment of Acute Myocardial Infarction, is disclosed.

The provided system is further adaptable to assist clot disruption and systemically delivered drug therapy and effectiveness localized to other body regions experiencing an acute state of low blood perfusion, such as in acute vascular obstructions to the cerebral, pulmonary and peripheral vasculature.

A first aspect of the present invention is to provide a system and a preferred apparatus enabling an easy to impart, non-skilled based vibration therapy, comprising the steps of placing a vibrator non-invasively (without an imaging modality) to a selected body surface deemed proximate to a culprit vascular obstruction, and applying low frequency vibration at a high force or displacement amplitude to the selected body surface, preferably as an adjunct to systemically administered drug therapy.

A second aspect of the present invention (as a means to optimize the system), provides methods and apparatus to the incorporation of ultrasonic imaging, which enables a "skilled" operator (when available) to intelligibly direct externally imparted vibration in a relatively easy and portable manner towards an invasive target. As a third aspect of the present invention (and as a means of further optimizing the system), methods and apparatus enabling cardiac phase controlled vibration delivery is additionally provided, which may be of use in cardiac applications, when or if the patient deteriorates to a state of cardiogenic shock.

A fourth aspect of the present invention is to integrate the foregoing into an effective emergency response system for treatment of acute vascular obstructions. The system is optionally portable to meet the needs of first line emergency treatment in the field, employable with drugs, and adaptable to meet the needs of differing operators with varying levels of training and skill.

It is accordingly a general object of this present invention to define a utility for externally placed, high amplitude, low frequency vibration to the thorax of a patient, as a synergistic adjunct to systemically delivered drug therapy, in a cardiological treatment application associated with acute myocardial infarction.

It is a further object of the present invention to provide an emergency response system whereby 1-1000 Hz, (or preferably 1-120 Hz and optimally 20-120 Hz compressional waves) are applied externally at high force and displacement amplitude to the chest wall of the patient, to act to as an adjunct to systemically introduced drug therapy in the first line treatment of acute ST elevation myocardial infarction.

It is a further object of the present invention to provide an emergency response system which is adaptable to provide externally imparted, high amplitude low frequency vibration to improve drug therapy and localized drug effectiveness to a variety of body regions suffering from an acute, emergent state of low blood perfusion, such as the body regions of the brain, lung, and the periphery.

It is a further object of the present invention to provide an emergency response system which is simple and easy to use, without a skill requirement beyond what a nurse, paramedic, or even the patient (i.e. by self administration) could typically provide.

It is a further object of the present invention to provide a preferred higher powered vibrator with a higher force and displacement amplitude potential for vibration delivery to selected body surfaces than what has been described in the prior art, in recognition that a potential degree of overlying soft Ussue injury such as a bruise or a degree of patient discomfort, is of small consequence relative to the gains of an improved thrombolysis in an emergency situation to restore vessel flow to a major infarcting internal organ such as the heart.

It is a further object of the present invention to provide a preferred vibrator of the aforementioned type which is of a size and shape to enable hand held operation, such as to add portability, maneuverability, and ease of placement of the vibrator to varying body surfaces, as well as a moduable or controllable means of applying engagement force by the hand or hands of an operator.

It is a further object of the present invention to provide a preferred vibrator of the aforementioned type with an amplitude regulating mechanism, such as to enable a manual adjustment of displacement amplitude or force of vibration emitted to a tolerance level of a patient, which may be very low or very high depending on the body surface and constitution of the patient treated.

It is a further object of the present invention to provide a preferred vibrator of the aforementioned type which is operable to a broad range of selectable frequency, amplitude and wave form parameters, such to enable an effective research as well as clinical tool.

It is a further object of the present invention to provide a vibrator with a selection of vibration/body surface attachment interfaces, such as to accommodate a preferred method and/or skill level of an operator in order to enhance vibration transmission and effectiveness.

It is a further object of the present invention to provide a vibration/body surface attachment interface of the above type, comprising at least one contact (or contact node) adapted in size and shape to enable efficient seating within a rib space of a patient in order to optimize vibration transmission to the chest wall and vascular structures within the thoracic cavity.

It is a further object of the present invention to provide an vibration/body surface attachment interface of the above type, comprising a pair of contacts (or contact nodes) such as to enable contact at a pair of application sites preferably bridging the sternum of the patient, in order to improve penetration to the mediasteinal cavity, and match the anatomic configuration of the base of the heart wherein the coronary anatomy is substantially distributed.

It is a further object of the present invention to provide a vibration/body surface attachment interface of the above type, comprising a plurality greater than a pair of contacts (or contact nodes) wherein pairs of contacts are grouped together bridging an elongated support structure at adjustable levels, such as to enable contact at a plurality of application sites (or intercostal space levels) preferably bridging the sternum of the patient, in order to maximize penetration to the heart which is variably situated depending on the anatomy of the patient.

It is a further object of the present invention to provide a vibration/body surface attachment interface of the above type, which in addition to supplying the means of transmitting low frequency vibration from a vibration source to a patient, is additionally enabled to provide ultrasonographic imaging such that a skilled operator (when available) may optimize penetration and target vibration to a culprit vascular region or target area while concurrently imaging the target.

It is a further object of the present invention to provide a vibration/body surface attachment interface of the above type, which in addition to supplying the means of transmitting low frequency vibration from a vibration source to a patient, is additionally enabled to emit a therapeutic low frequency ultrasonic wave form such as to provide a pair of therapeutic oscillating wave forms (i.e. low frequency vibration plus low frequency ultrasound) in concert.

It is a further object of the present invention to provide a vibration/body surface attachment interface of the above type, which is not only enabled to transmit low frequency vibration from the vibration source and concurrently emit a low frequency ultrasonic treatment wave form (i.e. as above), but is additionally enabled to provide ultrasonographic imaging such that an operator may optimize penetration and target low frequency vibration and low frequency ultrasonic emissions to a culprit vascular region or target area while concurrently imaging the target.

It is a further object of the present invention to provide a mechanical and adjustable engagement means to a vibrator comprising a clamp, wherein the clamp is adapted to bedside or stretcher use to hold the vibrator against a patient's body surface (such as the chest wall or back), so an operator need not hold the vibrator in place by hand throughout the course of vibration therapy.

It is a further object of the present invention to provide a mechanical and adjustable engagement means to a vibrator comprising a belt system, wherein the belt system is adapted to encircle a patient's body part (such as the thorax) and hold the vibrator against the body surface treated (such as the chest wall) so an operator need not hold the vibrator by hand, and so that the patient may sit up or even ambulate.

It is a further object of the present invention to provide a vibration method and apparatus for enabling cardiac phase controlled time and optionally frequency varying vibration delivery, to enable the selection of vibration timing algorithms designed to optimize vibration of the heart and coronary arteries. Cardiac phase controlled vibration is of particular importance in cases of acute myocardial infarction which have deteriorated into cardiogenic shock, wherein vibration timed exclusively to the diastolic cardiac phase provides a positive inotropic effect in addition to mechanical agitation of the heart and coronary arteries.

It is a primary object of the present invention to provide a self-contained, first line, mobile emergency response system and kit (and method of drug delivery) for treatment of acute, emergent, thrombotic and/or vasospastic vascular obstructions by trained professionals (in the ambulance, before transportation, or in hospital), wherein the mobile, emergency response kit comprises: a high powered low frequency vibrator, a selection of interchangeable attachment interfaces including those enabling ultrasonic imaging and low frequency ultrasonic therapeutic emissions, a drug delivery means, at least one and preferably a plurality of useful drugs to be delivered, and a portable carrying case enabling storage and portability of the aforementioned members. Options to the mobile, emergency response kit include: an engagement means (selectable between a clamp and belt apparatus), and a cardiac phase controlled vibration delivery system (to optimize the timing of vibration delivery specifically for cardiac applications, which is of special importance in the case where the patient deteriorates into a state of cardiogenic shock).

It is a final object of the present invention, to provide a self contained, portable, emergency response system and kit (and method of drug delivery) for outpatient community use, wherein the portable emergency response kit comprises a high powered low frequency vibrator, and preferably at least one anti-anginal drug to be delivered. The portable emergency response kit is employable to a victim (or bystander) in the community for self (or assisted) treatment of chest pain refractory to and/or complimentary with conventional anti-anginal therapy (e.g. nitro spray, or pill), wherein an acute coronary event cannot be ruled out.

BRIEF DESCRIPTION OF THE DRAWINGS

The apparatus and method of the present invention will now be described with reference to the accompanying drawing figures, in which.

DETAILED DESCRIPTION

Figure 1:
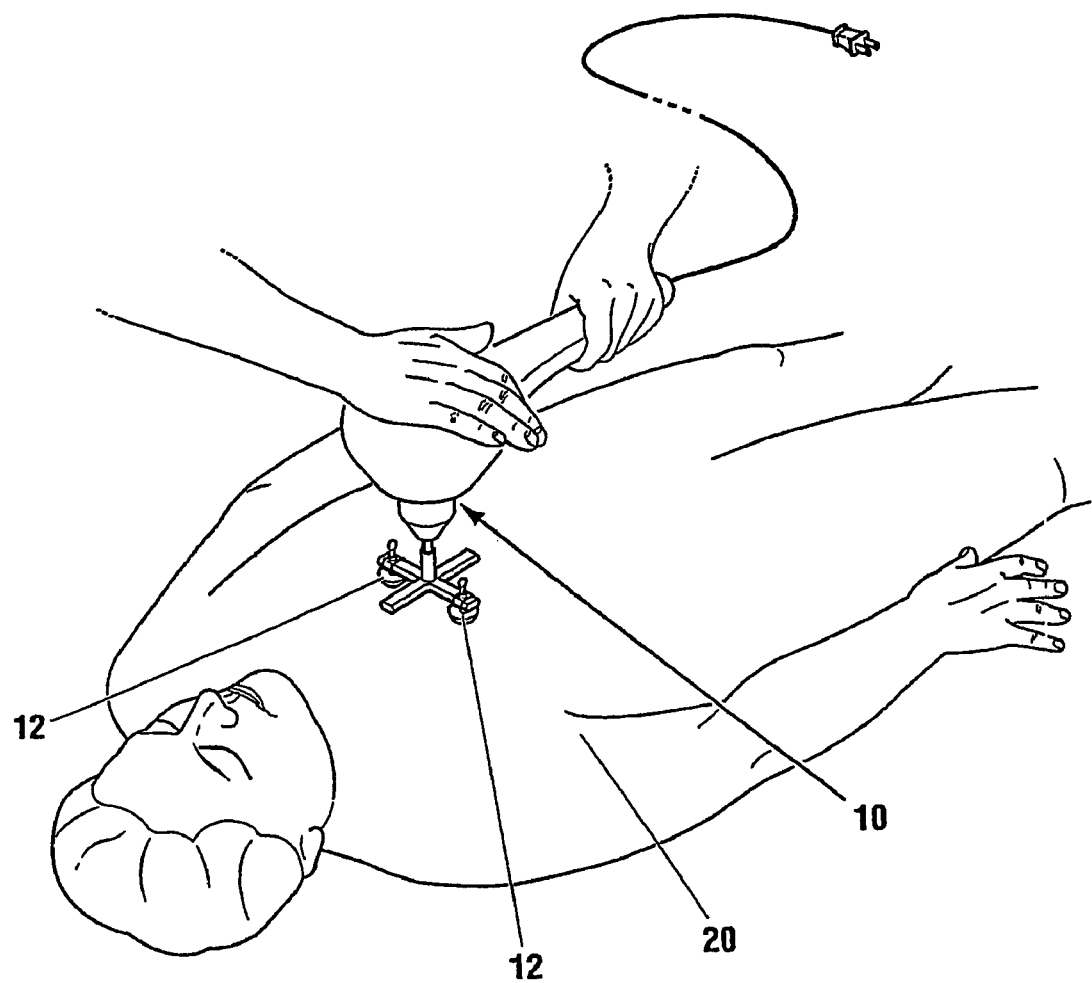
FIG. 1 is a perspective view of a supine patient receiving treatment from an operator held vibrator according to the invention.

The present invention is a first line emergency response system and apparatus for pre-hospital or initial in-hospital treatment of patients experiencing an acute to sub-acute thrombotic vascular obstruction and/or associated vessel spasm. The emergency application of high amplitude, noninvasive, transcutaneously imparted low frequency vibration, optimally as a synergistic adjunct to systemically delivered drug therapy, with or without concomitant ultrasonic imaging, for lysing and vasodilating acute vascular thrombotic obstructions, relieving spasm (if associated), and thereby restoring blood perfusion is disclosed. The invention is particularly effective against thromboses in the thoracic/mediasteinal cavity.

Low frequency vibration shortens the onset and accelerates the effectiveness of thrombolytics. Due to the urgency to treat heart attacks, strokes, pulmonary emboli, or acute peripheral arterial obstructions to major vessels, as cell death is directly proportional to time, it is of utmost importance to enhance the onset and accelerate the effectiveness of the imparted drug treatment in lysing or clearing vascular obstructions. The noninvasive application of low frequency vibration, in addition to its potential immediate availability to expedite emergency treatment, has the further advantage of not causing undue heating of the overlying tissue superficial to the site of vascular obstructions. Furthermore, the localized biophysical nature of low frequency vibration treatment is advantageous in that as it is not a drug, it will not cause adverse systemic biochemical effects, which can otherwise be difficult to reverse such as hemorrhage.

The term "vibration" according to the present invention relates broadly to a repetitive back and forth movement of an attachment interface (or vibratory contact) to be applied to or strike against (or percuss) a body surface of a patient, and should not be construed to mean, or be limited to any particular form of vibration unless otherwise specified. Furthermore, the term "continuously applied" or "continuous" vibration refers to vibration applied without a substantial break (or pause) in cadence (i.e. in accordance with the selected frequency), regardless of the duty factor of the wave form emitted. For cardiac applications in particular, "continuous" vibration refers to vibration imparted throughout (or substantially throughout) the cardiac cycle, and not just during the diastolic or systolic phase of the cardiac cycle.

The preferred embodiment of the emergency response system, or "Vibrinolytic Therapy", involves the application of continuously applied, noninvasive mechanical vibration at a frequency of 1-1000 Hz, preferably 20-120 Hz, and optimally 50 Hz to the chest wall as an adjunct to thrombolytic therapy in the treatment of acute myocardial infarction ("AMI"). A maximized source output displacement amplitude ranging from 1 up to 15 mm is selectively provided in the 1-120 Hz range. Displacement amplitude control enables the adjustment of vibration intensity to a tolerance level of a patient, which will vary markedly depending on the constitution of the individual treated. The emergency response system is not complicated and can be applied by a minimally trained paramedic or nurse without the need for special skilled imaging guidance or targeting.

The emergency response system facilitates the action of drugs such as: thrombolytics (e.g. ACTIVASE™ (Alteplase), TNKase™ (Tenecteplase), RETAVASE™ (Reteplase), Abbokinase™ (Urokinase), Kabikinase™ (Streptokinase with water), Streptase™ (Streptokinase with 0.9% NaCl solution), and Lanoteplase); GP 2b 3a platelet inhibitors (e.g. ReoPro™ (Abciximab), AGGRASTAT™ (Tirofiban hydrochloride), and Integrelin™ (Eptifibatide)); calcium channel blockers (e.g. ISOPTIN™ SR (Verapamil HCl), ADALAT™XL™ (Nifedipine), Cardizem™ (Diltiazem), and NORVASC™ (Amlodipine besylate)); Nitrates (e.g. Nitroglycerine (spray, pill or patch), isosorbide dinitrates (Isordil™ and Sorbitrate™), and Nipride™ (Nitroprusside)); Oral anti-platelets (e.g. Acetylsalicylic Acid (Aspirin), Plavix™ (Clopidogrel), and TICLID™ (Ticlopidine hydrochloride)); Anti-coagulants (such as heparin, and other blood thinning and coronary vasodilatory medication); concentrated oxygen and oxygen of ambient air. Micro bubble solutions which lower the cavitational threshold of a medium may also be considered as a further adjunct to the above listed pharmacological agents in conjunction with vibration therapy. Examples of micro bubble solutions include: EchoGen™ (Dodecafluoropentane emulsion), Albunex™ (5% human albumin), LEVOVIST™ (Galactose-Palmitic Acid ultrasound contrast agent), Air containing albumin microcapsules (Quantison™ and Myomap™), SonoVue™ (Sulfurhexafluoride) and Perfluorocarbon containing microbubbles (Perfluorocarbon exposed sonicated dextrose albumin PESDA). It should be understood that vibration therapy may be used to facilitate the action of a single drug, or a plurality of any of the aforementioned drugs in any combination, according to their preferred use.

The low frequency vibration is imparted to the chest wall (or other transthoracic body surface), and thereby by transmission to the epimyocardium of the heart and coronary arteries. The preferred embodiment (i.e. vibration adjunctive to thrombolytic therapy) is particularly effective for the treatment of acute ST elevation myocardial infarction. Vibration therapy can, with drug delivery, also be utilized for other forms of acute coronary syndromes such as Non Q wave (i.e. "Non ST elevation") MI or Unstable Angina where symptoms are otherwise refractory to medical management. A lower displacement amplitude may be considered for Non ST elevation coronary syndromes (e.g. to prevent bruising to the chest wall), wherein the displacement amplitude (or in a variation, force) of vibration is gradually titrated upwards until a relief of symptoms (or resolution of electrocardiographic evidence of ischemia) is realized.

Vibrinolytic therapy is effective as a first line medically adjunctive noninvasive mechanical intervention to coronary thrombolysis. During cardiogenic shock, lytic therapy alone, especially without the immediate availability of a cardiac cathlab, has a low rate of success, yet often remains the only realistic chance for reperfusion and in-hospital survival in centers without the option of emergency rescue Percutaneous Coronary Intervention ("PCI"). Vibration therapy may also be employed in conjunction with a lower dosage of thrombolytic drugs, independently, or in conjunction with other forms of medications when thrombolytic therapy is either contraindicated (e.g. because of a risk of bleeding), or not prescribed (e.g. non-ST elevation MI or unstable angina refractory to conventional medical management).

There are three primary effects of Vibrinolytic Therapy. First, thromboses or clots are disrupted as the mechanical agitation creates sheer stresses due to cavitation and sonic streaming and thereby loosens or breaks apart the clot, resulting in increased fibrin binding sites, and improved lytic penetration. Second, sonic streaming (unidirectional motion of fluid in a vibration field) and convection currents aid the diffusion process and promote mixing of intravenous drugs from the systemic circulation to the occluded, zero flow culprit vessel. Third, coronary vasodilatation within the culprit circulation is achieved as the smooth muscle within the thrombosed, often spasming coronary artery wall is relaxed by vibration (due to a vibration induced decoupling of the actin—myosin filaments of the sarcomere). Secondary therapeutic effects include a localized endogenous release of tissue plasminogen activator, an improved left ventricular ("LV") myocardial relaxation with a lowering of LV diastolic pressures (and thus potential improvements to diastolic, transmural coronary flow), the potential for a positive inotropic effect (leading to an increased lytic filtration pressure which is particularly useful in cardiogenic shock cases), the potential for decreased myocardial oxygen demand for equal contractility, and an improvement of lung/gas oxygen exchange (to provide additional oxygen to the heart and help relieve ischemic burden).

Referring to FIG. 1, a patient 20 undergoing Vibrinolytic Therapy according to the preferred embodiment is shown (IVs, drugs, nasal prongs and monitoring equipment etc. not shown). The preferred engagement means, the hands of an operator, for applying low-frequency vibration to the patient 20 is shown. Treatment begins with the administration of IV systemic thrombolytic therapy, plus any other helpful drug which is designed to effect clot dissolution and/or vasodilate the culprit coronary vessel. Thrombolytics may be continuously administered intravenously, and/or by bolus as prescribed by the physician. The contacts 12 of the preferred vibrator 10 are placed at the treatment site upon the chest wall of the patient 20, and vibration at high displacement amplitude (preferably the highest tolerable and judged safe to patient 20) is initiated. Vibration is preferably administered once drug therapy has been established, however may alternatively be initiated before or concurrent with the administration of drug therapy.

In acute myocardial infarction cases treated in an Emergency Room, preparation of the patient 20 should include sedation in similar manner to that of a cardiac cathlab PCI treatment where the patient is expected to remain flat (preferably supine) and relatively still for a period of time despite an anticipated uncomfortable procedure. The recommended application time is half an hour to an hour, or until clinical signs of reperfusion become manifest. An intravenous line is established for introduction of thrombolytic therapy, and any other IV therapy. Sedatives and anti-nausea medication and a foley catheter may be administered to avoid interruptions of treatment. A superficial administration of lidocaine to the skin of the chest wall application site may be considered. Oxygen should be administered to assist breathing. Intubation may be required with congestive heart failure cases in order to maintain oxygen saturation and patient positioning in a near supine position. When treatment commences in the field (as in an ambulance en route to hospital) a less extravagant preparation may be considered, and simply reclining a patient onto a stretcher with the establishment of an intravenous line would suffice in most situations.

For use of vibrator 10, the patient 20 is preferably placed supine, although two pillows behind the head may be allowable when the patient 20 is short of breath.

Figure 2:
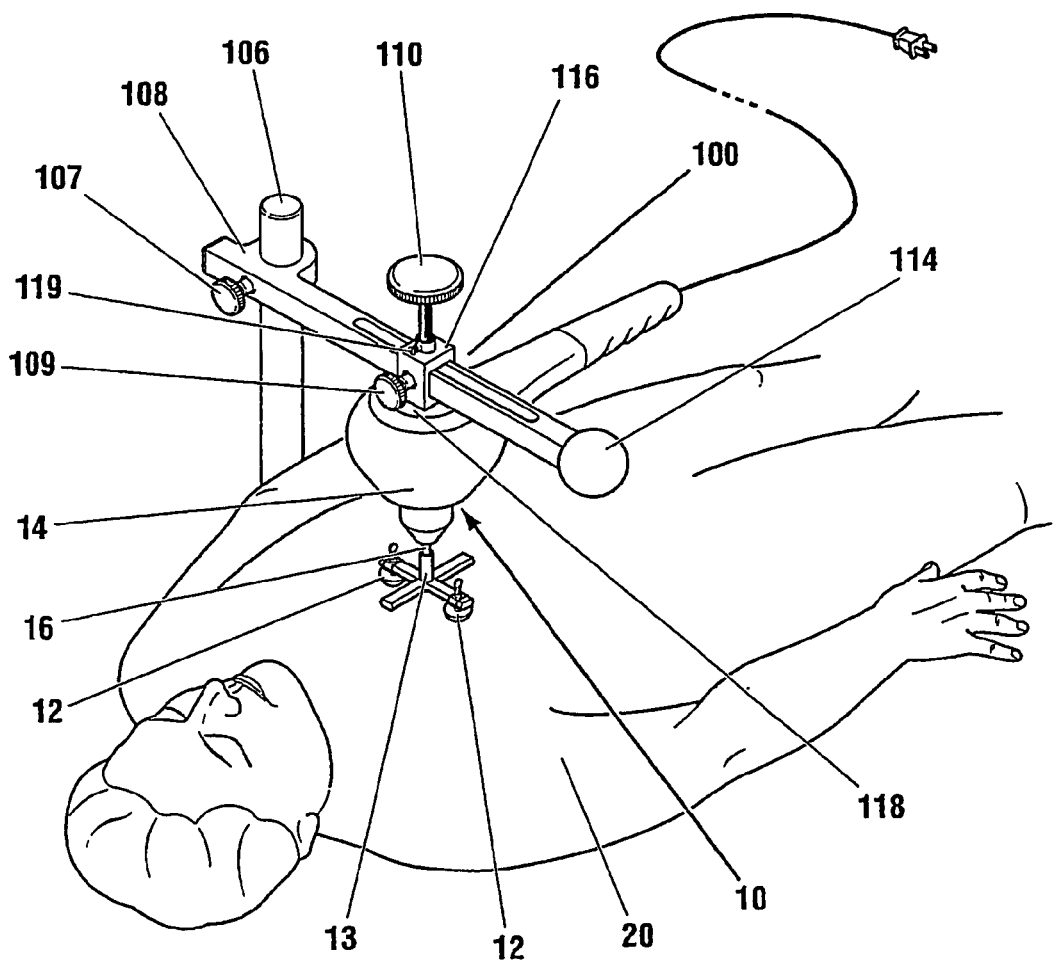
FIG. 2 is a perspective view of a supine patient receiving treatment from a clamped vibrator according to the invention.

Referring to FIG. 2, a variant means of engagement of vibrator 10 comprising clamp 100 is shown. The base (not shown) of clamp 100 is placed under the back or under the mattress of patient 20. Vertical bar 106 extends substantially vertically from the base. Horizontal arm 108 is slide-ably (i.e. in the vertical direction) and rotatably (i.e. in the horizontal plane) attached to bar 106 and extends at substantially 90 degrees from bar 106, whereby arm 108 will overhang the torso of patient 20. Horizontal arm 108 is lockable to vertical bar 106 by locking knob 107, or other suitable means. Vibrator 10 is attached to arm 108 via slide-able sleeve 116. Sleeve 116 is advantageously of a rectangular box shape, and is horizontally slide-able and disposed in the horizontal direction along arm 108. Sleeve 116 contains a central, threaded, vertical hole defining an internal threaded screw column (not shown), with a matching engagement screw 110 disposed and attached within the screw column. Sleeve 116 further includes locking knob 109, which tightens to lock vibrator 10 in place along arm 108. Vibrator 10 is selectively lowered and raised with engagement screw 110, which has threads that engage the interior surface of the threaded screw column. The lower or active end of engagement screw 110 removably attaches the non-active end of housing 14 of vibrator 10. Set screw 119 is mounted horizontally through the top portion of sleeve 116 and abuts engagement screw 110 thereby locking it in place during operation. A rotatable circular piece 118 disposed at the surface within the non-active end of housing 14 is provided such that housing 14 may remain stationary while engagement screw 110 adjusts vibrator 10 up or down. Inertial weight 114 is optionally added to arm 108 to dampen the movement of arm 108 during treatment. Clamp 100 engagement is advantageous as it frees an operator to perform other useful tasks.

The shaft 16 of vibrator 10 extends from the lower or active end of housing 14. A cross-shaped bifurcated connector 13 with a pair of bifurcated support arms (described later) is remove-ably attached to shaft 16. A pair of contacts 12, advantageously of silicone rubber, are attached to the support arms of bifurcated connector 13, and provide the attachment interface with the patient 20. The preferred placement of contacts 12 (i.e. the default placement) is the fourth intercostal space, about 2 cm anatomically rightward and leftward to the sternal margins (i.e. so the medial edge of each contact 12 is roughly 2 cm lateral to the sternal margins).

Alternatively, bifurcated connector 13 is oriented obliquely to the sternum of the patient 20 such that the contacts 12 are placed to the anatomic left fourth intercostal space and anatomic right fifth intercostal space, or as a further alternate, the anatomic left third intercostal space and anatomic right fourth intercostal space in order to better localize the source of vibration therapy to the plane of the base of the heart wherein the coronary arteries arise from the aorta, and are therein substantially distributed.

As an alternate for patient 20 positioning, patient 20 may be rolled over into the prone position, wherein contacts 12 of the vibrator 10 are placed to bridge the spine of patient 20 at the thoracic level. This offers a much more comfortable application to the patient 20 (which is of special importance in the case that patient 20 cannot tolerate high intensity concentrated forces to the chest wall), and a higher displacement amplitude vibration with a higher engagement force (i.e. force applied by the operator to vibrator 10 against the body surface treated—discussed later) may be selected. This position, as it is more stable and comfortable to the patient 20, is more particularly suited to clamp 100 engagement, which (as stated) advantageously frees the operator.

Figure 3:
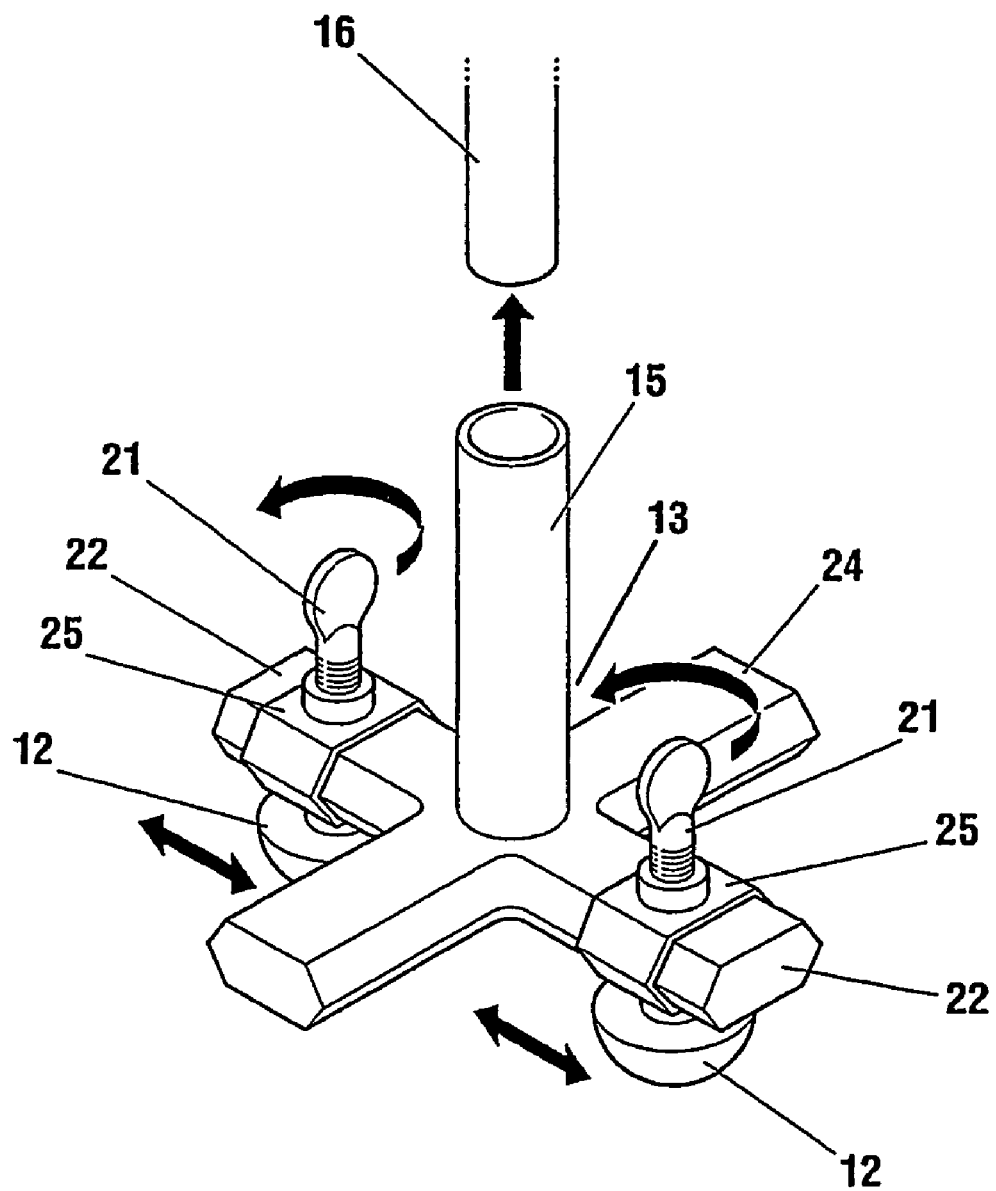
FIG. 3 is a perspective view of an attachment interface comprising a bifurcated connector with a pair of support arms, each support arm having a single contact according to the invention.

Referring to FIG. 3, the preferred attachment interface according to the preferred embodiment of bifurcated connector 13 is shown. Bifurcated connector 13 is comprised of a cross shaped base consisting of a pair of support arms 22, with a substantially columnar support structure 24 oriented at 90 degrees to support arms 22, and an upper vertical member 15, into which shaft 16 is inserted and is retained by means of friction, (or optionally any other known attachment means). Support structure 24 is not essential, but is preferred to enable the addition of further paired support arms 22 (and further contacts 12) at the discretion of an operator (described later). Bifurcated connector 13 is removably attached to shaft 16 of vibrator 10. As an option, bifurcated connector 13 may be fixed in place to shaft 16 of vibrator 10. The operator slides contacts 12 along support arms 22, so as to accommodate various chest wall sizes and sternum sizes. Each contact 12 is attached to sleeve 25 with locking screw 21, placed slide-ably and lock-ably upon each support arm 22 of bifurcated connector 13. Each sleeve 25 disposes a contact 12, wherein each contact 12 is removable to each sleeve 25 by a screw mechanism (not shown). Optionally, the spacing between contacts 12 may be made electronically adjustable by means of an operator adjustment control.

The choice of attachment interface and resultant number of contacts 12 utilized comprises a risk/benefit decision where the risk is patient bruising and the benefit is superior chest wall penetration of vibration thereby improving thrombolysis. The use of more contacts 12 will potentially result in relatively more bruising.

Figure 4:
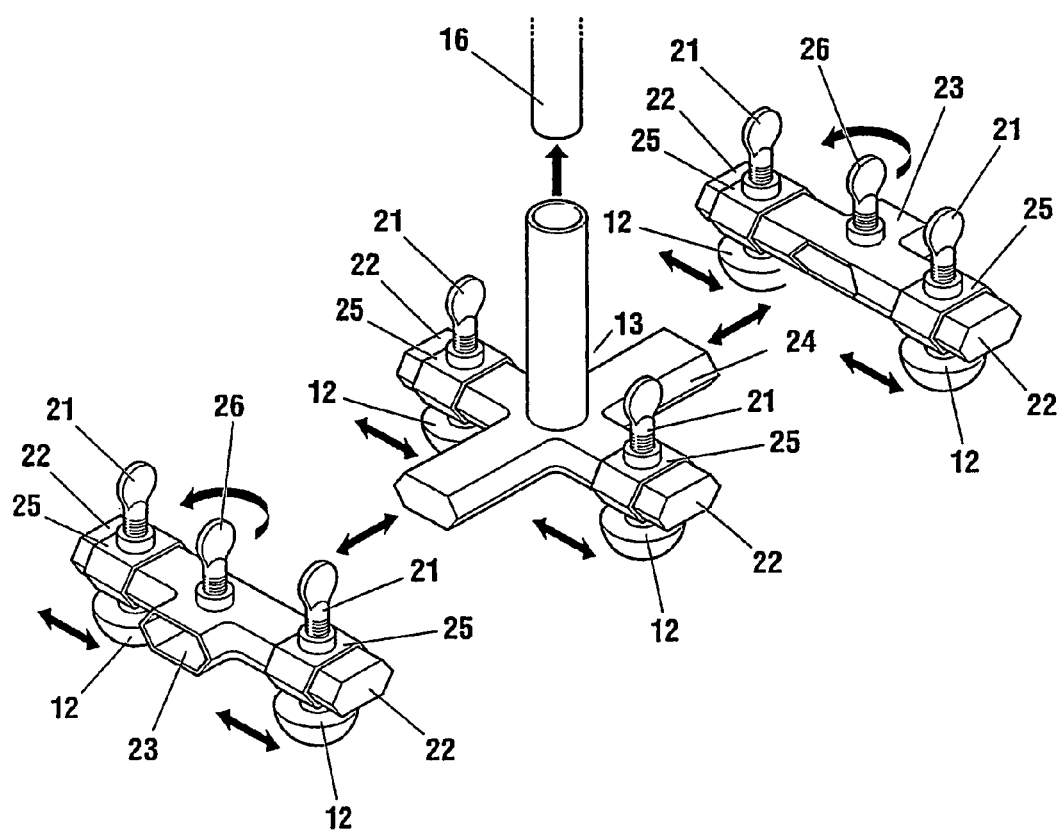
FIG. 4 is a perspective view of a variant attachment interface comprising a bifurcated connector having a plurality of support arms according to the invention.

In reference to FIG. 4, a variant means of chest wall attachment comprises the bifurcated connector 13, wherein support structure 24 is utilized to receive a pair of slide able sleeves 23, each sleeve 23 comprising an additional pair of support arms 22 to enable the attachment of up to three pairs of contacts 12 to preferably bridge the sternum at the level of multiple intercostal space levels, namely the 3rd, 4th and 5th intercostal space. Sleeves 23 are lockable to support structure 24 by locking screws 26.

To even further optimize the treatment, a further contact 12 with sleeve 25 (not shown) is optionally placed more laterally on at least one of the anatomically leftward oriented support arms 22 at the discretion of an operator, in order to enable application to the left mid clavicular line of the patient 20. This particular arrangement enables improved penetration to the mid Left Anterior Descending Artery in Acute Anterior Mich.

In further reference to FIG. 4, a modified chest wall attachment of bifurcated connector 13 (with additional two pairs of support arms 22) may optionally be utilized to provide attachment for contacts 12 to the anatomic left 3rd, 4th and 5th intercostal spaces along the anatomic left sternal border and anatomic left mid-clavicular line. This is accomplished by simply moving vibrator 10 (and thereby bifurcated connector 13 with additional two pairs of support arms 22) to the anatomic left of patient 20, such that the contacts 12 seat against the left sternal margin as well as within the left mid-clavicular line (i.e. as opposed to bridging the sternum). This modified chest wall attachment optimizes therapy directed specifically to the Left Anterior Descending Artery ("LAD"), where the diagnosis of acute anterior myocardial infarction has been made and the LAD, or any significant, large, leftward, coronary vessel is presumed the culprit. Alternatively, separate engagement means and a second vibration device (not shown) running preferably in phase (i.e. to avoid destructive interference of the vibratory signal) with pre-established vibrator 10 (or equivalent), may be utilized to provide additional therapy along the anatomical left mid-clavicular line and thereby the LAD distribution of the patient 20. It should be noted that vibration therapy may be contraindicated to the left 5th intercostal space (and lower intercostal spaces) at the level spanning the mid-clavicular line to the lateral margin of the chest wall of the patient 20 (i.e. approximating the apical window in standard 2D echocardiography), due to the remote possibility of intra-ventricular, apical early clot formation. While intra-ventricular thrombus formation is not generally considered a significant risk factor in the hyper-acute phase of an evolving acute myocardial infarction (i.e. period of time where thrombolytics are given), caution is warranted in certain cases. Such cases include patients who present "late" and who have the development of significant Q waves to the precordium on their initial 12 lead ECG. In these cases (and in reference again to FIG. 4) the contact 12 of the support arm 22 which is otherwise directed to the 5th intercostal space of the mid-clavicular line may be removed. Alternatively, an expedited 2D echocardiographic inspection of the apex of the heart of the patient 20 to rule out early clot formation (good Images supplying apical endocardial resolution in a non-foreshortened view as judged by an experienced echocardiographer must be obtained) would identify a low-risk group and thereby vibration therapy to the apex may commence as per the judgment of the attending clinician.

As a further option for thoracic cavity placement, (again when high intensity vibration is not tolerated to the chest wall of the patient 20), bifurcated connector 13 with additional two pairs of support arms 22 may be placed to bridge the spine of the patient 20, at a transverse level equating to approximately the 3rd, 4th and 5th intercostal space of the anterior chest wall, with the patient 20 reclined in the prone position.

Figure 5:
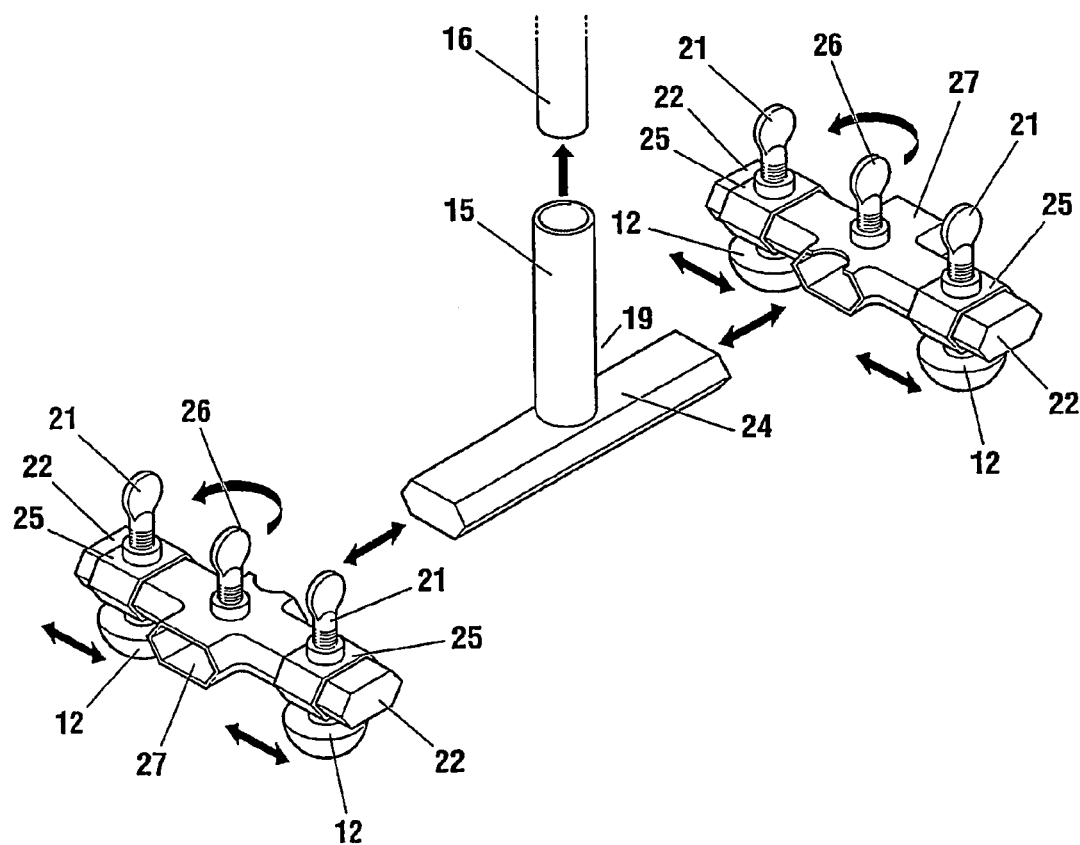
FIG. 5 is a perspective view of a variant attachment interface comprising a variant connector having two pairs of support arms according to the invention.

In reference to FIG. 5, a variant connector 19 comprising upper vertical member 15 (adapted for removable attachment to shaft 16 of the vibrator 10), and a variant base consisting of support structure 24 (in isolation) adapted to receive a pair of slide-able variant sleeves 27 is shown. Each variant sleeve 27 incorporates a medially located semicircular notch, and a pair of support arms 22 to enable the attachment of two pairs of contacts 12 in total (i.e. one contact 12 disposed on each support arm 22). This configuration enables the bridging of the sternum of the patient 20 via two pairs of application sites (i.e. via a total of four contacts 12) at the level of a pair of intercostal space levels, preferably the 3rd and 4th intercostal space. Alternatively, variant connector 19 may be placed such as to bridge the sternum at the 4th and 5th, or 3rd and 5th intercostal space level, and in yet a further variation, variant connector 19 may be placed obliquely across the sternum wherein the anatomically leftward oriented contacts 12 are placed one intercostal space higher (or superior), to the anatomically rightward oriented contacts 12 (i.e. such as to match the configuration of the base of the heart, as described earlier). The upper vertical member 15 (or optionally any other known attachment means) is disposed centrally and at a right angle to support structure 24 and preferably maintained equidistantly between slide able variant sleeves 27 (and thereby between the adjacent pair of supports arms 22), in order to enable a balanced configuration of attachment to the patient 20. The spacing between variant sleeves 27 (and thereby opposing support arms 22 and contacts 12) are slide-ably adjustable along support structure 24 (i.e. in a "longitudinal" direction, head to foot relative to the patient 20), and the spacing between contacts 12 is also adjustable along support arms 22 (i.e. in a "lateral" direction, side by side with respect to the patient 20). Optionally, the spacing between variant sleeves 27 (in the "longitudinal" direction) and contacts 12 (in the "lateral" direction) may be made electronically adjustable by means of an operator adjustment control.

To reduce the risk of bruising, the preferred bifurcated connector 13 giving rise to a pair of contacts 12 (as described) may be chosen.

Alternatively, to further minimize the extent of chest wall bruising to the patient 20, a solitary contact 12, attached to a variant, non-bifurcated connector (not shown), may be used. Solitary contact 12 may be located over a solitary target site on the patient 20 which by default is the 4th intercostal space, with the placement of the medial edge of the solitary contact 12 preferably about 2 cm anatomically leftward and lateral to the left sternal margin. In a further variation, the solitary contact 12 may be adapted to be placed by friction (or any other known attachment means) directly upon shaft 16 of the vibrator 10 without the use of variant, non-bifurcated connector (or other connecting means).

This variant technique (i.e. use of solitary contact 12), may be utilized, regardless of bleeding and or bruising risks, in the special cases of Anterior, Antero-Septal, or Antero-Lateral AMI, where the leftward coronary circulation is presumed the culprit and whereby solitary contact 12 is placed anatomically leftward to the sternum of the patient 20. To improve efficiency and penetration of this variant technique, the patient 20 may be rotated from the supine position onto his or her left side (e.g. between about 20 and 90 degrees from the plane of the bed) and supported for example by pillows or a wedge, as this position drops the heart and left coronary circulation further leftward from under the sternum bringing the culprit vessels (i.e. the Left Main, Left Anterior Descending and Left Circumflex) in closer proximity to solitary contact 12 which has been placed leftward the sternum. In the case of clamp 100 engagement, to maintain correct orientation and a perpendicular alignment between solitary contact 12 and the chest wall of the patient 20 (i.e. wherein patient 20 is not lying perfectly supine), a rotating, pivoting and locking universal joint (not shown) may be incorporated at the juncture of the lower aspect of engagement screw 110 and rotatable circular piece 118 of the non-active end of housing 14 of the vibrator 10. In these cases the patient 20 should preferably be only partially rotated onto his or her left side (i.e. up to about 20 degrees from the plane of the bed) such as to maintain structural stability of clamp 100 engagement. Alternatively (and preferably) the hand engagement, or a belt engagement (described later) may be utilized.

Next, the vibrator 10 is turned on, (preferably at a low displacement amplitude level such as 2 mm) and the contact or contacts 12 are placed against the target site (or sites) on the patient 20.

In an attempt to more exactingly position the contact or contacts 12 in relation to the heart, the attending physician, nurse or paramedic may first confirm or optimize a choice of a single selected intercostal space, chosen from the anatomically leftward 3rd, 4th or 5th intercostal space, using a stethoscope wherein relative loudness of heart sounds suggest anatomical location of the heart, as well as optimal sonic transmissibility through the chest wall. The pair of contacts 12 (comprising the preferred attachment means) should be placed to either side of the sternum, with the anatomically leftward oriented contact 12 placed upon the determined intercostal space as judged by the stethoscope method. The anatomically rightward oriented contact 12 should be placed either perpendicularly across the sternum at the level of the chosen "optimal" intercostal space, or obliquely across the sternum whereby the anatomic rightward placement of the contact 12 is placed one intercostal space lower (or inferior) to the anatomic leftward placement of the contact 12. The sternal margin (i.e. so the medial edge of the contacts 12 are applied directly over the sternal margin) may be considered for large breasted women. The heart sounds should be inspected along the anatomic left sternal margin, so as to identify the optimal leftward intercostal space. As an alternative means of attachment, solitary contact 12 may be placed anatomically leftward to the sternum at the determined optimal intercostal space chosen by the operator according to the stethoscope method. Relative loudness and sustain ability of heart sounds during gently held inspiration should preferably be evaluated by the operator (the louder the better) when judging the quality of a sonic treatment window and also inspecting for heart location which is known to vary markedly depending on the individual treated. The target intercostal space wherein heart sounds are best heard is then marked with ink (or crayon, or felt, or any other marker), and the anatomically leftward oriented (or solitary) contact 12 of the vibrator 10 is placed in proximity to the mark.

In a further alternative method to minimize bruising and to establish optimal transmission to the heart, vibration therapy may be provided in conjunction with high frequency, diagnostic ultrasonography (i.e. "HFUS" around 1-7 MHz), in order to optimize placement of the contact or contacts 12 of the vibrator 10 to the chest wall of the patient 20. To confirm the ideal placement of the low frequency treatment vibration source, a trained HFUS operator (such as a Cardiac Ultrasound Technologist, or echo trained Cardiologist for example) must first locate the ideal parastemal sonic penetration window via ultrasonographic techniques, wherein the preferred sonic window provides a clear visualization of the mid to basal aspect of the heart, (ideally depicting the basal aspect of the akinetic or hypo kinetic myocardial wall which represents by anatomic reference where the culprit thrombus is most likely to reside). The imaging probe is preferably maintained in a near perpendicular orientation relative to the surface of the chest wall interrogated. The attachment variation comprising solitary contact 12 is preferable in these cases to minimize overall chest wall trauma, and focus the intensity of the therapeutic vibration over the optimized placement site comprising the determined sonic penetration window. Optionally the otherwise preferred pair of contacts 12 may be placed to either side of the sternum, with the anatomically leftward oriented contact 12 placed upon the determined sonic penetration window, and the opposing anatomically rightward contact 12 placed either perpendicularly across the sternum at the same intercostal space level, or one intercostal space lower (or inferior) to the leftward oriented contact 12. The operator employs a conventional two-dimensional ultrasound device (not shown), so as to mark the determined sonic penetration window on the chest (e.g. with a pen or felt marker) and place and optionally angle the chosen attachment interface of the treatment vibrator 10 accordingly. As stated the sonographer should preferably (while imaging) hold the imaging probe substantially perpendicular to the chest surface (i.e. ideally less than a 20 to 30 degree angulation from the normal to the chest wall) such as to ensure a sonic penetration window which is proximate the target area, and which is also consistent with an anticipated perpendicular, or near perpendicular attachment of the contact or contacts 12 of the low frequency treatment vibrator 10. Pathologies such as COPD, with increased lung size and therefore interference with ultrasound, may indicate the use of different intercostal spaces (i.e. such as the 5th intercostal space) to establish the optimal sonic penetration window. Attachment means can be by hand, clamp 100 or a variety of engagement garments (which are described later). The parastemal chest wall is preferred but other sonic windows may be utilized (note that the apical window should be used judiciously as per the methodology as stated earlier).

In a further variation of the above HFUS imaging method, a "dual function", simultaneous vibration and imaging system may be employed via a single combined imaging/treatment probe (described in detail later). In this variation to the preferred embodiment, low frequency vibration therapy is advantageously employed in conjunction with high frequency ultrasonography (i.e. HFUS), where both high and low frequency wave forms are applied simultaneously (i.e. in real time) via a single instrument, which comprises an ultrasonic imaging transducer operatively connected (or acoustically coupled) to the active end of a low frequency vibration source operational in the 1-1000 Hz range. The ultrasound imaging transducer acts in this case as a variant attachment interface (or contact) to the patient 20, thereby enabling the transmission of low frequency vibration from the vibration source, while concurrently enabling ultrasonic imaging to direct vibration, at the discretion of an operator. The method of the dual function system comprises the placement of the imaging/treatment probe (with the accompaniment of ultrasonic conduction gel) to the skin of the patient 20, such as to establish a sonic penetration window depicting a target of low frequency vibration (such as the base of heart in AMI cases, as described earlier). Once a sonic penetration window is established, low frequency vibration is initiated and transmitted through the ultrasound imaging transducer attachment interface (preferably as an adjunct to drug therapy), and the application site is additionally maintained through continued monitoring of the ultrasonic image provided. In this manner, intelligible anatomic placement and angulation of the imaging/treatment probe is achieved, thereby optimizing the delivery of low frequency vibration therapy to the culprit vascular region targeted.

Optimally in still a further variation, low frequency ultrasonic treatment (LFUS) is also used in combination with HFUS imaging and low frequency treatment vibration in the 1-1000 Hz range, via a "multifunction system" employing a single variant LFUS enabled imaging/treatment probe (not shown and described later). In this variation to the preferred embodiment, low frequency vibration therapy is employed in conjunction with high frequency ultrasonography (i.e.

HFUS) and "treatment" low frequency ultrasound (i.e. LFUS) simultaneously and in real time, where all three wave forms are applied in concert via a single transmission instrument. In this manner, direct HFUS imaging and targeting may be combined with low frequency vibration in the 1-1000 Hz range, and low frequency ultrasonic energy (at around 20-100 kHz, preferably 27 kHz), to optimally agitate and disrupt the culprit vascular region targeted.

The use of a combined imaging/treatment probe, (or "single transmission instrument"), regardless of employment of the "dual function" or "multifunction" system, at least initially involves a skilled imaging technique to direct vibration therapy to the ideal sonic penetration window. The use of both hands to support and maintain the imaging/treatment probe with enough engagement force to the chest wall (or other body part) is suggested, or the operator can alternatively, use one hand, or utilize any of the suggested engagement means according to the present invention, as long as the appropriate sonic penetration window is visually monitored and maintained. An inertial weight may be placed to the backside (or optionally within the housing) of the chosen "transmission instrument" adding inertia to the apparatus and thereby assisting the operator ergonomically who may hold the transmission instrument in position by hand. While the supine position for the patient is generally preferred, different patient positioning (e.g. with the patient lying to some degree on his or her left side, up to the left lateral debecutis position) could be utilized as per the judgment of the operator, in order to establish the highest quality and most stable sonic penetration window available. The parasternal windows remain the preferred application site if available (i.e. in coronary applications), however other sonic windows may be considered (note that the apical window should be used judiciously as per the methodology as stated above). Duty factor and intensity level may be selected with respect to the LFUS application (i.e. in the multifunction system), such as to provide the means to avoid undue heating to the skin surface of the patient 20. Alternatively, a wet cool cloth applied intermittently to the skin surface, and/or a periodic change of application site (or even transmission instrument), may be utilized to prevent skin burning of the patient 20 during joint LFUS use.

The next step in the preferred treatment method is to apply appropriate engagement force to the chest wall of the patient 20 with the vibrator 10. The attending clinician applies force to the vibrator 10 against the target area by hand, or alternatively via rotation of engagement screw 110 of clamp 100. A relatively constant, firm engagement force of at least 5-10 N, preferably 20-100 N, and optimally 50-100 N, (measurable at shaft 16 of the vibrator 10 during operation), should be obtained according to the tolerance and safety of the patient 20. In the case of clamp 100 engagement, engagement force should preferably be first established during gentle held expiration of the patient 20. The engagement force should preferably not exceed 100 N, such as to avoid possible dampening of oscillations of the vibrator 10. A force meter (discussed later and not shown) is optionally utilized to confirm engagement force. For clamp 100 engagement, the placement of the base of clamp 100 (described later) under the mattress of the patient 20, may be advantageous in some cases, in that the mattress provides for a slight decompression when the patient 20 inhales, so as to limit the maximum engagement force on inspiration and make for a more comfortable application to the patent 20. In the preferred case where the vibrator 10 is engaged by the hand or hands of an operator, the engagement force can be monitored and maintained at a near constant level, as well as modulated as per the needs (or tolerance levels) of the patient 20. Referring back to FIG. 1, housing 14 of the vibrator 10 is advantageously "L" shaped, incorporating a handle to facilitate hand held operation. Activation of the vibrator 10 preferably precedes engagement, however alternatively the vibrator 10 may be activated after engagement to the patient 20, at the discretion of an operator.

As a rule of thumb, the engagement force should be the maximum force, which is tolerable for the patient 20, and will not cause the vibrator 10 to significantly dampen (or stop) its oscillations. Satisfactory engagement is further identified once the patient 20 identifies a "fluttering" in the teeth or jaw (or exhibits an undulation in the voice) which indicates efficient transmission. It should be noted that patient comfort can be greatly improved by moving the application sites about, even slightly within the rib spaces, or alternatively to differing rib spaces (in keeping to the selection of methods previously described). Once engaged satisfactorily (i.e. in the case of clamp 100 engagement), the operator tightens set-screw 119 to lock engagement screw 110 in place.

Vibration therapy preferably commences with selection of the maximum displacement amplitude or force judged safe and tolerable applied for emergency situations. This maximal setting, may result in bruising to the chest wall (or other body surface treated), and an informed consent should preferably be signed by the patient 20 if feasible.

It should be understood that the exact order (or selection of steps) in the application of engagement force vs. displacement amplitude level of the vibrator 10 against the body surface of the patient 20 is not critical, as long as the end result (i.e. for vibration therapy) is that a firm engagement force (i.e. at least 5-10 N. and preferably within the range of 20-100 N) at a high displacement amplitude (i.e. greater than 2 mm, and preferably in the range of at least 4-15 mm, and ideally maximized to patient 20 tolerance) is ultimately established.

If displacement amplitudes of less than or equal to about 2 mm, and/or engagement forces of less than approximately 10 N are not tolerated to the chest wall of the patient 20 (even in the special case where lidocaine is administered to the chest wall surface), then patient 20 may optionally be placed in the prone position (not shown) and the contacts 12 may be placed to bridge the spine of patient 20 In the upper thoracic region. Vibration at higher displacement amplitudes (often tolerable to about 15 mm), and higher engagement forces (often tolerable to 100 N or greater), may be safely utilized in the majority of these cases, to ensure and maximize penetration to the mediasteinal cavity and enhance clinical effectiveness of vibration.

Tests by the applicant have shown that low frequency vibration penetration through soft tissue is related to the applied displacement amplitude and engagement force of the vibration contact to the body surface vibrated. It has been ascertained that the desired engagement force of a vibration source placed against the chest wall of the patient 20 is preferably at least 5-10 N, and optimally greater than 20 N, and up to 100 N (when tolerated), to confer ideal penetration. When vibration is applied to the muscle groups adjacent to the spine of the patient 20 (as an alternative means of transthoracic vibration to the mediasteinal cavity), optimal engagement force is much higher (i.e. greater than 100 N may be utilized), as the application is far better tolerated by the patient 20, and higher engagement force and displacement amplitudes are generally required to achieve therapeutic levels of mediasteinal cavity penetration. Optimal displacement amplitudes also vary significantly with the constitution and tolerance levels of the patient 20, as well as the selected body surface treated. Vibration displacement amplitudes of greater than 2 mm (and preferably in the range of at least about 4 mm-12 mm), are preferred for chest wall applications, and displacement amplitudes of at least about 6 mm-15 mm are preferred for transthoracic applications from the backside of the patient 20. In the case where ultrasonic (HFUS) imaging is employed to direct or target vibration therapy, penetration to the heart is generally increased, and higher amplitudes and engagement forces of vibration (i.e. which may cause bruising to the skin surface vibrated and patient 20 discomfort) are not absolutely required. Still however (regardless of the use of HFUS enabled directed therapy), the highest possible combination of engagement force and displacement amplitude is still recommended to yield best results in emergency treatment of acute thrombotic vascular obstructions.

In the case that the patient 20 is unable to tolerate even modest levels of vibration (i.e. both displacement amplitude and engagement force, regardless of body surface vibrated), then a gentle application utilizing the weight of the vibrator 10 (or at the least 5 newtons of engagement force) and the maximum low level of displacement amplitude tolerable to patient 20 should be utilized. Displacement amplitudes of 1-2 mm (or even less, e.g. 0.1-1.0 mm—accomplished through dampening vibration through a cushion for example) may be used in these cases.

The frequency range employed is between 1-1000 Hz, preferably between 20-120 Hz, and optimally 50 Hz. It is preferable to match the resonance frequency of the heart, which falls within a 20-120 Hz range. The heart, receiving vibration stimulus at or near its resonance frequency will vibrate with the highest possible displacement amplitudes at the localized areas which best receive the signal. External vibration at the resonance frequency enables transmission of the vibration signal internally throughout the ventricular chambers with highest efficiency, thereby vibrating the entire heart and effecting optimal intra ventricular transmissibility. Optimal intra ventricular transmissibility aids agitation of the entire coronary tree, including those parts of the tree hidden behind lung or soft tissue which are poor transmitters of vibration and therefore otherwise difficult to penetrate directly with sonic mechanical energy. The preferred frequency for chest wall vibration is a 50 Hz sinusoidal compressional wave, owing to this wave-forms known superior chest wall penetration, intra-ventricular transmissibility, lytic penetration, clot disruption, and arterial vasodilatation characteristics.

Higher frequencies (i.e. 150-1000 Hz), or even in the sub-ultrasonic to ultrasonic range (i.e. 1000 Hz-100 kHz), while optional for clot disruption and improved drug action to sites of thromboses, are generally higher than the resonance frequency of the heart and hence not readily transmissible to all areas of the coronary anatomy by intra ventricular transverse transmission means. Higher frequency vibration also requires diminished displacement amplitude for safe clinical use, which is a further limitation to this wave-form's potential penetrating and agitative power (i.e. through the chest wall or other body part treated). A directed approach through an identifiable sonic penetration window to ensure adequate penetration to target areas by the much weaker (i.e. lower displacement amplitude—in the low millimeter to sub millimeter ranges) signal is strongly recommended for frequencies greater than 150 Hz, again at the highest amplitudes and forces judged tolerable to a patient in emergency situations. Concomitant simultaneous high frequency ultrasound imaging (i.e. HFUS) in conjunction with lower displacement amplitude vibration therapy at frequencies of greater than 150 Hz, to target and direct a sonic penetration pathway to culprit areas (as per the dual function system described earlier), is the optimal method of employment for such higher vibration treatment frequencies.

Generally, a range of frequencies selectively chosen between 1-1000 Hz, with the selection of multiple displacement wave-forms is disclosed. The present invention provides a broad range of frequencies and wave-forms which are advantageous, as the apparatus and system is optionally employed both as a treatment system and a research tool.

Treatment continues during and/or post the administration of preferred drug agent(s) wherein stated agents may be selected solely or in any combination from the group of thrombolytics, GP 2b 3a platelet inhibitors, anticoagulants, oral anti-platelets, vasodilators, cavitating micro bubble solutions, concentrated oxygen, and the oxygen of ambient air. Vibration treatment ends once clinical signs of reperfusion are identified or until emergency invasive treatment (i.e. PCI and/or emergency revascularization surgery) is established.

Figure 6:
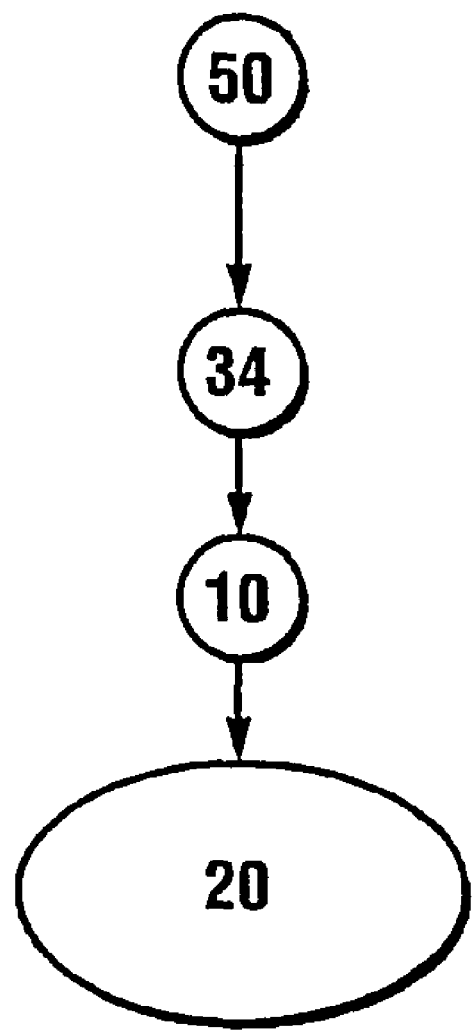
FIG. 6 is a schematic diagram of the preferred vibrator and its operable components according to the invention.

The preferred vibration apparatus for deliverance of vibration therapy is represented diagrammatically in FIG. 6, where an operator (not shown) provides input to processor 34 via interface 50 of the preferred vibrator 10. Interface 50 comprises a set of manually operated control switches (not shown), advantageously located for easy access on the exterior surface of housing 14 of vibrator 10. Processor 34 in turn controls vibrator 10, delivering the prescribed frequency, displacement amplitude and displacement wave form (described later) of continuously applied vibration to the target site (or sites) on the patient 20 via a sole attachment interface. As an option to interface 50, other variant interfacing means such as an electronic touch pad or key board (either located remote or on housing 14) may alternatively be employed. Processor 34 is advantageously located within housing 14 of vibrator 10, and comprises a programmable logic control of known type. The preferred vibrator 10 is particularly appropriate for first line treatment such as in emergency rooms and ambulances during transport, where in both cases non-experts are operating the device. The preferred embodiment is designed to provide a simple and reliable first line response to AMI incidents, which can be operated with minimal training and easily applied in the field or emergency room setting.

Figure 7:
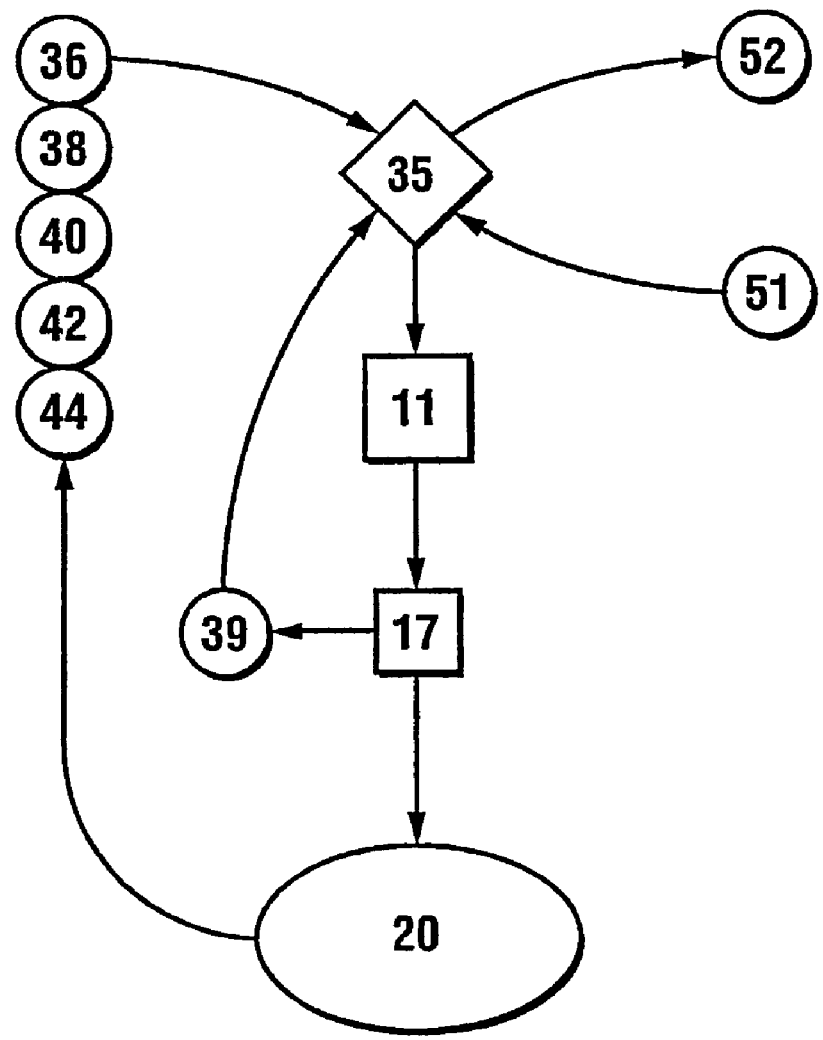
FIG. 7 is a schematic diagram of the variant cardiac phase controlled vibrator and its operable components according to the invention.

Referring now to FIG. 7, in some cases it may be preferable to apply vibration therapy with an "advanced method" comprising use of physiological and mechanical monitoring or sensing equipment and varying timing and/or frequency algorithms for vibration delivery. With varying algorithms, cardiac phase dependent time and optionally frequency varied vibration therapy may be employed when best suited to the clinical situation. Enablement of the "advanced method" is provided via a variant cardiac phase controlled vibrator 11 (i.e. "variant 1"), which is advantageously of like construction to preferred vibrator 10, but is adapted to receive and respond to more advanced commands from variant processor 35 and a variant interface 51. In this variation, both variant processor 35 and variant interface 51 are located remote from the housing of variant cardiac phase controlled vibrator 11.

The needs for varying timing and frequency algorithms in vibration therapy will differ depending on the clinical presentation. For example, in cases of hemodynamically stable acute ST elevation myocardial infarction, continuous vibration which is cardiac phase controlled whereby approximately 50 Hz vibration is imparted during ventricular diastole and approximately 100 Hz during ventricular systole may be employed, which is suspected by the applicant of the present invention to produce a more therapeutic result. Any known phase monitoring means (see below) may be used to determine the timing of the cardiac phase, and this is firstly determined automatically via variant processor 35, and then is optionally further fine-tuned by an operator via an adjustment (or "vibratory timing adjustment control") made to variant interface 51. Cases of complicating cardiogenic shock or unmanageable congestive heart failure with acute ST elevation myocardial infarction dictate diastolic only timed vibration. Vibration timed specifically to the diastolic phase of the cardiac cycle provides a form of ventricular assist with a positive inotropic effect, and, as the diastolic myocardium is particularly stiff in times of profound ischemia, the vibration signal exhibits excellent intra ventricular transmissibility (i.e. transversely propagated internal vibration) to ensure an agitative treatment response to all areas of the coronary circulation. It is significant that the conventional treatment of acute MI with the complication of cardiogenic shock with thrombolytics only (i.e. with no adjunctive interventional or mechanical treatment) is extremely ineffective, with a low likelihood of reperfusion and a 63% in-house mortality reported.

In the advanced method, additional physiological monitoring equipment is provided to make possible the application of special vibration timing algorithms according to cardiac phase. Such physiological monitors include; electrocardiogram ("ECG") 36, impedance plethysmograph 40 (optional), phonocardiography system 42 (optional), and noninvasive blood pressure apparatus 44 (optional). The monitoring and sensing equipment, all of commercially known types, are interfaced with the patient 20. A transesophageal accelerometer 38 placed on a transesophageal lead may be used, (as disclosed in Japanese Pat. No. JP 4156823 to Takishima et al., incorporated herein by reference), to confirm and monitor maximal sonic penetration to the esophagus, which represents the posterior aspect of the heart. An external accelerometer 39 is also provided, which is advantageously placed on shaft 17 of variant cardiac phase controlled vibrator 11 ("variant 1"), to assist in monitoring the timing of vibration therapy in real time, and to confirm the functioning (i.e. frequency and amplitude) of the applied vibration. Alternatively, variant processor 35 may optionally emit a signal indicating when variant cardiac phase controlled vibrator 11 ("variant 1") is active. The monitored physiological and mechanical output interfaces with variant processor 35, which is thereafter processed and sent to display monitor 52 for real time wave form display. The operator, based on the output displayed on display monitor 52, may select and modulate programmed timing and frequency algorithms designed to optimize therapy by entering a selection to variant interface 51 which interfaces with the operator and sends commands to variant processor 35. For example (as mentioned previously), specifically timed sinusoidal cardiac phase controlled vibration at 50 Hz In ventricular diastole and 100 Hz in ventricular systole, at maximum tolerable force or displacement amplitude, is preferred for use with the advanced method in the treatment of hemodynamically stable ST elevation infarcts. Vibration timed exclusively to the diastolic phase of the cardiac cycle at 50 Hz (known to produce a positive inotropic effect), is preferred for hemodynamically unstable ST elevation infarcts, (e.g. with associated cardiogenic shock). ECG 36 output is essential to provide a timing differentiation means between the diastolic and systolic phase of the cardiac cycle. Variant processor 35 will interpret the ORS deflection as the onset of systole, and will assign a preprogrammed default rate related time delay to dictate the timing of the onset of diastole. The default time delay may be monitored and adjusted by the operator (i.e. with the vibratory timing adjustment control), based on physiological signals viewed upon display monitor 52. Monitoring ECG 36 output can additionally provide information to heart rhythm and reperfusion which is represented by a sudden decrease in ST segment elevation.

Display monitor 52 comprises a CRT (or other) monitoring screen enabling real time output wave form display, and digital read outs plus annotations where all necessary information for an operator to make judgments is displayed. Variant interface 51, comprises a combination of an electronic control touch screen and a keyboard entry (although other known interfaces such as voice recognition, push buttons, sliding switches, control knobs or any other suitable interface may be used), to allow for selection and modification of: vibration displacement amplitude, displacement amplitude according to cardiac phase, displacement wave form selection, ECG 36 monitoring selection, low pass ECG filter (on/off), mode selection (i.e. diastolic vs. continuous vibration emission), vibratory timing adjustment control, and frequency algorithms. Variant processor 35 is adapted to receive and process input from variant interface 51, and through analysis of the physiological information delivered from the monitoring equipment, control variant cardiac phase controlled vibrator 11 ("variant 1") to cause vibration at the time period, frequency, displacement amplitude and wave form, as selected by the operator. ECG 36 employs a standard monitoring system to represent inferior (II, III, avF), anterior (V lead) and lateral (V5, I, aVL) electrocardiographic information, but may be of other configurations. Impedance plethysmograph 40 comprises a commercially known impedance plethysmography system enabling a relative comparison of real time changes in intra thoracic blood pressure. Impedance plethysmograph 40 further relays the timing of the dichrotic notch (signifying the onset of diastole) to display monitor 52 and thereby to the operator, making manual adjustments to the timing of the onset of diastolic vibration more accurate (however in the absence of impedance plethysmograph 40, the onset of diastole may be judged at the termination of the T wave of the wave form displayed from the ECG 36). The termination of diastolic vibration is triggered automatically by variant processor 35 in recognition of the deflection of the QRS complex provided by ECG 36 monitoring means. It is therefore important to achieve a good "tall" QRS complex on the chosen ECG 36 monitoring lead without a great deal of muscle artifact. A low pass ECG 36 filter (filter not shown), operational with a 40 Hz cutoff is included to minimize such artifact. A wedge filter (automatically set to the frequency of the vibratory signal) is also included, to substantially eliminate vibratory artifact on the ECG 36 waveform trace. Phonocardiography system 42 of known type is optionally included as it also provides information as to the timing of the onset of diastole (i.e. by the initial deflection of the "S2" heart sound), and thereby provides additional information to assist in the manual adjustment for diastolic only vibration.

Noninvasive blood pressure apparatus 44 comprises a noninvasive real time blood pressure monitor provided by arterial tonometry which non-invasively senses the pressure of the radial artery by way of an external pressure transducer to provide a real time arterial blood pressure wave form, but may alternatively be a noninvasive blood pressure monitor of any commercially known type, which quantifies the blood pressure of the patient 20. For example an automatic noninvasive blood pressure cuff system could be utilized with periodic digital readouts sent to variant processor 35 and thereby to display monitor 52. An electronic strain gauge force meter (not shown) is optionally employed to monitor the engagement force of the variant cardiac phase controlled vibrator 11 ("variant 1") to the chest wall (or thorax) of the patient 20. Alternatively, any commercially known gauge such as a weight scale may be used to determine the engagement force. Accelerometer 39, placed on the shaft 17 of variant cardiac phase controlled vibrator 11 ("variant 1") is utilized to confirm that appropriate vibration is being applied, and to provide a real time comparison of treatment vibration application versus ECG 36 and optionally impedance plethysmograph 40, and/or phonocardiography system 42 wave form trace.

Regardless of method employed (i.e. "simple" or "advanced"), the patient 20 should preferably be monitored by at least one clinician or nurse during the course of vibration therapy for treatment of acute ST elevation myocardial infarction. Pain and nausea may require an adjustment in the amplitude or engagement force of vibration or even a cessation of treatment. The operator can readily adjust or remove the vibrator 10 (or provided variant) as required. Particularly using the "advanced method", the operator or clinician may adjust the treatment to suit patient 20 physiological status which is displayed on display monitor 52. For instance a sudden drop in blood pressure, usually indicating deterioration into cardiogenic shock, would be registered by plethysmograph 40 and/or noninvasive blood pressure apparatus 44. The operator may decide to discontinue continuous vibration therapy (i.e. vibration applied throughout the cardiac cycle), which may have a negative inotropic effect on heart failure, and switch to diastolic only vibration, which is known to provide a positive inotropic effect. If hemodynamic compromise is borderline, the operator may optionally limit or reduce the displacement amplitude of vibration selectively during the time period of ventricular systole, while maintaining maximized displacement amplitude during ventricular diastole.

Figure 8:
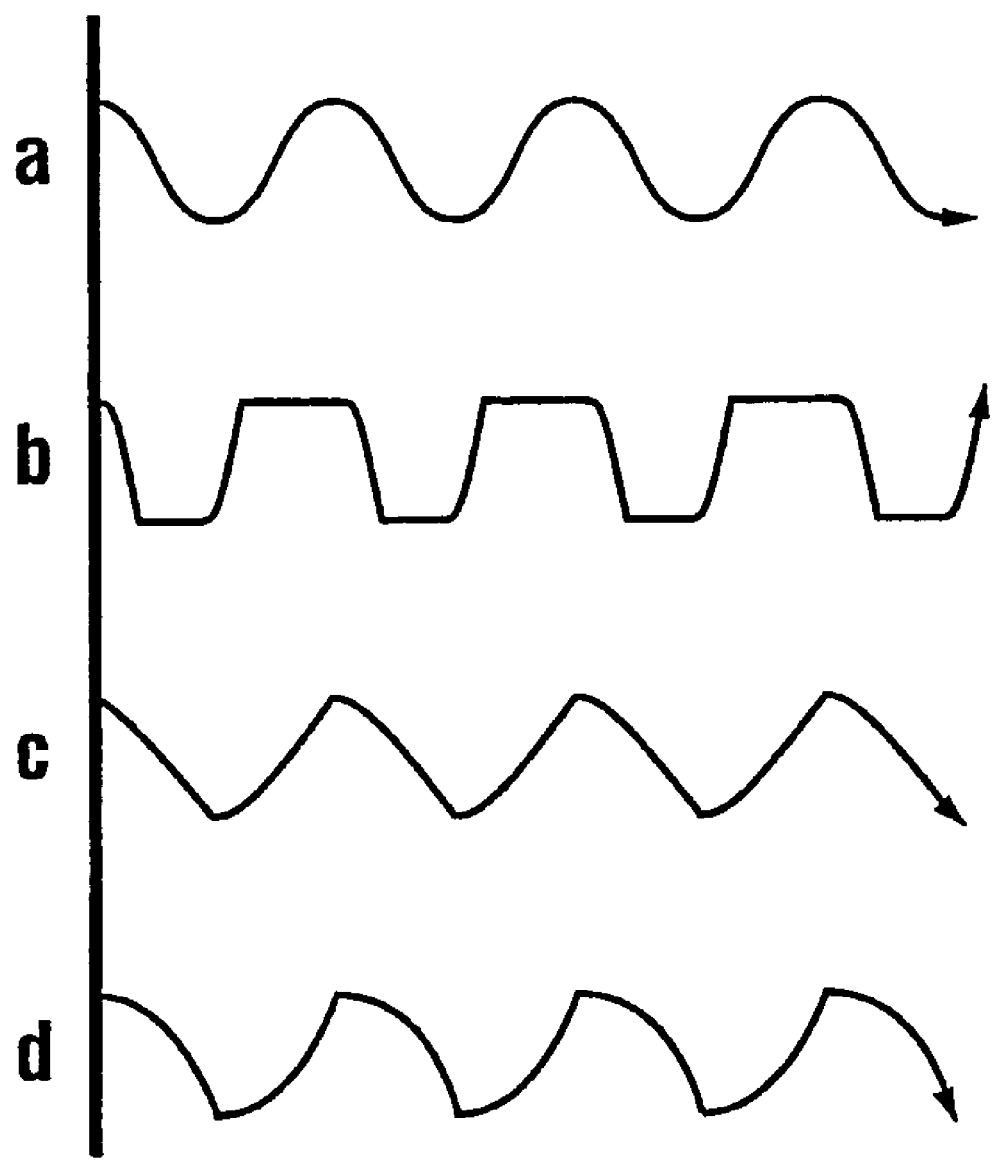
FIG. 8 is a graphic illustration of a variety of vibratory displacement wave forms according to the invention.

In reference to FIG. 8, low frequency vibration via a plurality of displacement wave forms with "displacement" on the vertical axis and "time" on the horizontal axis, (with respect to the movement of a contact 12) is shown. While the preferred embodiment incorporates use of a sinusoidal vibration displacement wave form <a>, other displacement wave forms of vibration may alternatively be selected such as; square waves <b> (or "pulsed" or "percussive" waves, with a steep displacement rise), saw tooth waves <c> (with a gradual displacement rise), exponential waves <d> (with an acceletory, non-linear displacement rise) or any other linear or non-linear wave shape (or combinations thereof according to the invention. High impact square wave <b> vibration may be particularly advantageous in some instances due to its known superior penetration and disruptive characteristics through human tissue.

The above methods of low frequency vibration therapy may be used for several pathologies and in different settings. Six prophetic examples of clinical use illustrated in reference to the heart, in various in-hospital or pre-hospital settings are as follows:

First, vibration therapy may be employed in an emergency room or ambulance in the first line treatment of acute ST elevation myocardial infarction, preferably adjunctive to thrombolytics, or any other form of medical therapy.

Second, also in an emergency room or ambulance as a first line treatment, vibration therapy may be employed to reduce the dosage of thrombolytics and/or anti-platelet agents required for those patients where thrombolytic therapy and/or anti-platelet therapy is relatively contraindicated due to increased bleeding risks (and also to save costs), or even eliminate the use of drug therapy entirely.

Third, vibration therapy may be employed in the in-hospital or pre-hospital setting for treatment of chest pain refractory to medical management in cases of Non-ST elevation MI or cardiac ischemia preferably as an adjunct to drugs such as but not restricted to IV or SL nitroglycerin, GP 2b-3a platelet inhibitors, and heparin. Lytics are not indicated in such cases. Gently applied vibration timed to the diastolic phase of the cardiac cycle (i.e. via the "advanced method"), which is known to increase coronary flow in stable, ischemic, non occlusive states (as per the teachings of JP 8089549 to Koiwa et al., incorporated herein by reference), may be tried in these cases as a first measure to limit vibration therapy and thereby limit potential bruising to the patent 20 who may be anti coagulated. The intensity level of the applied vibration may be gradually (or incrementally) increased to a threshold of patient comfort. If diastolic only vibration does not relieve the chest pain (or if not available) continuously applied vibration (i.e. throughout the cardiac cycle, in systole and diastole) should be selected, which is more effective for more serious coronary syndromes wherein the mechanisms are either or both of coronary artery spasm and coronary thromboses formation. Continuous vibration should preferably be applied at incrementally increasing displacement amplitudes (or force) until the maximal levels of comfort and safety are realized and the symptoms are relieved. This gentle method of progression of phase modulation and displacement amplitude in ischemic but substantially non-infarcting syndromes is important as the situation is not acute, and the patient will likely be (as previously stated) anti-coagulated and will bruise easily.

Fourth, vibration therapy may be employed prophylactically in the step down telemetry unit or CCU for example, adjunctive to nitrates (and/or blood thinning medications) for more pronounced coronary events (i.e. with ST/T wave changes on the ECG telemetry monitor) which are otherwise refractory to conventional drug management, whereby an acute denovo blood clot and/or acute coronary vessel spasm at the earliest of stages may be in the process of formation. Newly formed (or forming) blood clots are easily disrupted and mobilized prior to the deposition of fibrin by the vibration methods disclosed.

Fifth, vibration therapy may be applied to the chest wall in the cardiac cathlab setting as an adjunct to drugs such as nitroglycerine, nipride, verapamil, GP 2b 3a platelet inhibitors, and thrombolytics, for acute to sub-acute procedures prior to, during, or after PCI (or heart catheterization), where there may be significant clotting in the artery at the onset of or immediately following the procedure. Vibration therapy could for example be utilized pre-procedure, as an adjunct to GP 2b 3a platelet inhibitors. +−. thrombolytics while the patient 20 is en route to the cathlab for emergency PCI. Post procedure, vibration therapy may for example be appropriate in "no-reflow" or "slow-flow" situations following or during an intervention, for instance when clots and/or micro emboli dislodge and affix themselves to the distal, arteriolar circulation to cause very poor flow, chest pain and injury. It should be noted that if chest wall vibration therapy where to be imparted during a heart catheterization (or PCI procedure), the guide or diagnostic catheter should be withdrawn from the ostia of the selected coronary artery prior to initiation of the vibration therapy in order to avoid shear forces and possible dissection to the ostia of the coronary.

Sixth, vibration therapy may be employed in the community for acute states of coronary insufficiency resulting in symptoms of possible acute myocardial infarction refractory to nitroglycerine treatment in the patient 20. Every bout of "angina" that patient 20 in the community experiences might represent an acute coronary event wherein a plaque has ruptured and a blood clot (and/or vessel spasm) has formed. In these cases, patient 20 will typically have tried nitro spray-.times.3, each dose spread five minutes apart, without relief of chest pain which may be quite severe. Patient 20 will then proceed to dial "911" for emergency assistance, wherein the diagnosis of an acute coronary obstruction leading to an acute MI cannot be ruled out until professional care arrives. As stated above, hyper acute early clot formation is particularly amenable to dissolution via mechanical agitation. High amplitude vibration therapy concentrated to the chest wall in these instances can provide such agitation, and can be therefore (prospectively) an extremely important first line emergency tool, for capturing the window of susceptibility of a newly formed blood clot and eradicate it before it has a chance to grow and harden, and cause damage to the myocardium, or even sudden death to the patient 20. For treatment, the patient 20 should be ideally resting in either the supine position or seated comfortably upright in a chair. Ideally a friend or bystander should provide vibration therapy to the patient 20 (preferably with the continued administration of nitrates) until symptoms have dissipated or until professional care arrives.

Vibration therapy is effective in emergency situations where an acute vascular obstruction has occurred and cell death or hemodynamic compromise is imminent, particularly when there is a poor prognosis for drug therapy alone and emergency invasive intervention is delayed or not available.

Acute pulmonary emboli and in particular saddle emboli (which involves a critical life and death situation) are also good candidates for external, transcutaneous vibration therapy adjunctive to standard drug therapy (e.g. IV thrombolytics, anticoagulants etc.). Chest wall vibration to the vascular region of the lung (pulmonary vasculature) and pulmonary artery are readily achieved by the methods disclosed below. The underperfused body region in this case is the organ and tissues of the lung and, in the case of saddle emboli, the entire body. A frequency of less than 1000 Hz, and preferably selected from the 1-120 Hz range at maximum tolerable force or displacement amplitude is suitable for such applications. The choice of 50 Hz sinusoidal vibration is preferred, as 50 Hz sinusoidal vibration can be delivered at relatively high amplitude, has excellent chest wall to thoracic cavity penetrability, and is also a well established frequency known to produce cavitation and acoustic streaming (to assist in thrombolytic to clot filtration), as well as vascular dilation and clot disruption. As an option, square wave <b> (i.e. with a steep displacement rise for better penetration and disruptive action), saw tooth wave <c>, exponential wave <d>, or any linear or nonlinear (or combination thereof displacement wave form, may be used (see FIG. 8). As the lungs also reside in the thoracic cavity, the present invention also functions to vibrate the vasculature of the lungs and pulmonary artery with low frequency vibration. Ultrasonic imaging means to target the pulmonary artery (i.e. where saddle embolus is presumed the culprit) may be employed to target the vibration therapy. Without ultrasonic imaging, the preferred vibrator 10 (with preferably a pair of contacts 12) is preferably placed to bridge the sternum at the level of the third intercostal space of the patient 20 (which approximates the bifurcation point of the left and right pulmonary artery). Alternatively, chest wall attachment may comprise a plurality of contacts 12 either bridging the sternum or applied to the left sternal margin of preferably the third, fourth and fifth intercostal space. A frequency of less than 1000 Hz, preferably 1-120 Hz and optimally about 50 Hz is then applied at maximum tolerable amplitude in conjunction with a systemically delivered drug such as a thrombolytic, anti-platelet, anticoagulant or vasodilatory drug. The application of high amplitude low frequency vibration commences adjunctively to drug therapy until signs of reperfusion or until invasive corrective measures may be established. Optionally, vibration therapy may be utilized independently (i.e. without a drug), or with a decreased dosage of drugs.

Vibration therapy may also be employed to treat acute Cerebral Vasculature Accidents, preferably once determined as ischemic or embolic in origin, adjunctive to thrombolytic therapy where brain function is still arguably salvageable. Transcutaneous cranial vibration to the vascular regions of the brain of the patient 20 are readily achieved by the methods below. The underperfused body region in this case is the organ and tissues of the brain of the patient 20. The vibrator 10 (with preferably a pair of contacts 12) is advantageously attached to the posterior aspect of the neck of the patient 20, however the lateral or posterolateral aspects of the neck may also be used. Alternatively, vibration may be applied directly to the cranium of the patient 20 via a helmet (not shown), cushioned to avoid bruising to the head of patient 20, which comprises an alternative attachment interface to vibrator 10. A frequency of less than 1000 Hz, and preferably selected from the 1-120 Hz range, is then applied at a selected displacement amplitude (i.e. from 1 mm to 15 mm displacements), in conjunction with a systemically delivered drug such as a thrombolytic, anti-platelet, anticoagulant, or vaso-dilatory drug. The choice of 50 Hz sinusoidal vibration is preferred, as 50 Hz sinusoidal vibration can be delivered at a relatively high displacement amplitude, and is a well established frequency known to produce cavitation and acoustic streaming (to assist in thrombolytic to clot filtration), as well as vascular dilation and clot disruption. As an option, square wave <b>, saw tooth wave <C>, exponential wave <d>, or any linear or nonlinear displacement wave form (or combinations thereof may be used (see FIG. 8). The displacement amplitude of vibration should be selected judiciously with the more serious natured acute ischemic strokes (i.e. where there is a traumatic deficit noted), preferably receiving relatively higher displacement amplitudes in keeping with an increased benefit to risk ratio (i.e. benefit of improved thrombolysis to restore vital function vs. risk of cerebral bleeding). Optionally, vibration therapy may be utilized independently (i.e. without a drug), or with a decreased dosage of drugs.

Vibration therapy in accordance with the present invention may be further utilized to facilitate the restoration of blood flow In acute, emergent peripheral arterial obstructions such as those occurring in the limbs of a patient. When the obstruction (which is usually thrombo-embolic in nature or involving acute thrombosis on a preexisting ulcerative plaque) involves a critical segment of the arterial system where the collateral potential of blood perfusion is poor, the clinical picture is dramatic with loss of limb viability and amputation imminent if not treated effectively within six hours. Transcutaneous peripheral vibration to the vascular region of the effected peripheral body part (including all organs and tissues distal to and including the clavicles and groin region of the patient 20) are readily achieved by the methods disclosed below. A vibration frequency of less than 1000 Hz, preferably 1-120 Hz, and optimally 50 Hz sinusoidal vibration, is applied transcutaneously to the presumed culprit area, at a high force or displacement amplitude (preferably at the highest levels deemed tolerable and safe to the patient 20). As an option, square wave <b>, saw tooth wave <C>, exponential wave <d>, or any linear or nonlinear (or combination thereof) displacement wave form, may be used (see FIG. 8). Vibration therapy is preferably used in conjunction with pharmacologically active agents such as thrombolytics, anti-platelets, vaso-dilatory or anticoagulant drugs as a first line method to restore early flow, and to also act as a bridge to emergency corrective surgery or intervention. A singular or plurality of contacts 12 are utilized to provide maximal agitative vibration energy imparted to the culprit area. The contacts 12 are placed on the limb surface affected, with contact preferably established at the point at which distal pulses are lost. Typical attachment areas comprise the pelvis/groin area (i.e. iliac and femoral arteries), thigh (femoral artery), popliteal space (popliteal artery), lower leg (tibial artery), periosteum of the clavicle and first rib (sub-clavian artery), soft tissue area between the clavicle and trapezius muscle (sub-clavian artery), axilla (axillary artery), brachium (brachial artery), anti-cubital fossa (brachial artery), and forearm (radial artery). The contacts 12 are advantageously comprised of silicone rubber, however any commercially available material, preferably resilient and substantially non-distortable may be used to form the contact surface of contacts 12. Alternatively, the contact surface of specially adapted "peripheral" contact heads (not shown) are malleable to enable a more exacting vibration contact to complex, uneven and rigid contours (such as in contours overlying or directly adjacent to bone) of the body surface of the patient 20. The peripheral contact heads in this variation (which are of a known type) are comprised of a solid base piece, which partially encapsulates an incompressible fluid with a semi-compliant membrane overlying the active end of the base piece and incompressible fluid. For acute peripheral vascular obstruction applications, the engagement means of vibrator 10 may be by hand, by clamp 100, or alternatively via a belt engagement system with Velcro™ strap securement (described later). Ultrasonic imaging means to target a culprit blood clot within a culprit vascular region may be employed to enable direct visualization and targeting of the vibration therapy with highest efficiency. The application of vibration optionally commences with adjunctive drug therapy until signs of reperfusion or until invasive corrective measures may be established. Optionally, vibration therapy may be utilized independently (i.e. without a drug), or with a decreased dosage of drugs.

Referring again to FIG. 1, the preferred embodiment of the vibrator 10 (i.e. in the emergency treatment of ST elevation MI) is applied by the hands of an operator with the patient 20 lying substantially in the supine position.

The preferred vibrator 10 of the present invention is operable to generate and emit vibration selectably in the 1-120 Hz range. A second variant "research" vibrator (i.e. "variant 2"—not shown), is also provided, being adapted to operate in a higher frequency range, above 150 Hz, and up to 1000 Hz (which is designed primarily for research applications and applications directed by ultrasonic imaging). Thus, vibration therapy within the range of 1-1000 Hz is provided according to the invention.

Vibrator 10 contains a high powered linear stepper motor (not shown—located within housing 14), with sufficient power to enable operation at engagement forces of up to approximately 100 N. Vibrator 10 is characterized to enable selective frequency and displacement amplitude control in the 1-120 Hz and 1-15 mm range respectively, as well as selectable displacement "wave form" control (comprising a selection of sinusoidal <a>, square <b>, saw tooth <c>, and exponential <d> wave shapes—see FIG. 8.). Vibrator 10 is further programmable to emit any other linear or nonlinear displacement wave shape (or combination thereof. Use of vibrator 10 enables the delivery of high amplitude forces of vibration concentrated to the selected body surface treated.

The active end of the provided linear stepper motor is operatively linked with and drives the proximal "non-active end" of shaft 16 (not shown—within housing 14), which is thereafter projected through housing 14 (now shown), to enable contact with the selected attachment interface. As an option, a displacement amplifier (such as a lever or a pneumatic displacement amplification system) may be incorporated to establish the necessary displacement amplitude emission required.

The selection of displacement amplitudes ranging from 0 (off), 1 to 15 mm deflection is provided by an amplitude regulatory mechanism which is incrementally controlled by the operator. The amplitude regulatory mechanism is enabled by the provided linear stepper motor stroke length control. The stroke length control is coordinated via commands from processor 34 and interface 50, which all taken together comprise the "amplitude regulatory mechanism" of vibrator 10. Vibrator 10 is also optionally programmable to enable selectable vibration force (or power) control at a given frequency, as an alternate to (or in addition to) the provided selectable displacement amplitude (or stroke length) control.

Operation of the preferred vibrator 10 is as follows. The operator inputs commands to the interface 50, which thereafter sends commands to processor 34, located upon and within (respectively) housing 14 of the vibrator 10. Commands from interface 50 to processor 34 indicate the operator selection of various vibration signal parameters such as emission frequency (i.e. 0 off, 1-120 Hz), vibratory displacement waveform emission shape (i.e. sinusoidal <a>, square <b>, saw tooth <c>, or exponential <d>—see FIG. 8.), and stroke length (i.e. 0 off, 1-15 mm deflection). Processor 34 (with signal generator and amplifier) generates the appropriate signal at the appropriate power level to feed the input of the provided linear stepper motor.

As an option, vibrator 10 will also contain programming and controls to enable the selection of variable frequency response algorithms (or variations in vibration cadence), such as in the Sharper Image Massager Model HF 757 incorporated herein by reference.

A fan (not shown) is advantageously disposed within housing 14 of vibrator 10, (as well as a pair of ventilation holes through housing 14—also not shown), to assist convective air cooling of the provided linear stepper motor therein, which enables prolonged application times such that the device will not overheat. Alternatively, any other known suitable cooling mechanism may be used. Vibrator 10 is also optionally equipped with a controllable heating system for heating the contact surface of contacts 12, which may add benefit to clot disruption in superficial treatments of thromboses. Any one of the amplifier or signal generator within processor 34 or interface 50 (in any combination) may optionally be disposed remote from housing 14 of vibrator 10, such as to enable a more compact and lighter weight hand held instrument.

Vibrator 10 is powered by an AC power cord, or as a second means via a portable DC battery pack (not shown), which is slide-ably and removably disposed within the handle of housing 14. The DC battery pack is advantageous as it enables operation of vibrator 10 in the field wherein no AC power is commonly available.

It should be emphasized that vibrator 10 as herein described comprises a "preferred" means (or apparatus) for the deliverance of emergency vibration therapy in the treatment of acute vascular obstructions, and accordingly may be varied in many ways to enable function of an effective emergency response system. In essence, any low frequency non-invasive vibrator (or percussion, or oscillation device by other name) with an attachment interface suitable to enable direct selected body surface contact, operational in the range of 1-120 Hz (and optimally within the range of 20-120 Hz), with a displacement amplitude enablement of greater than 2 mm (and preferably greater than 4 mm), which is operable under engagement forces at least 5-10 N (and preferably greater than 20 N), may be used to provide an effective emergency tool in the emergency response system. Possible variations to vibrator 10 for enablement of the emergency system are described later.

The variant research vibrator ("variant 2") of the present invention contains a high powered voice coil adapted to generate vibration at higher frequencies within the 1-1000 Hz range. The variant research vibrator ("variant 2"), is characterized to enable both selective frequency and force (or power) control at a given frequency, and is also operational under engagement forces to the human body of up to about 100 N. Frequency settings above 150 Hz have limited displacement amplitude emission capability, in keeping with clinical safety concerns and the mechanical constraints of the provided system, and are thereby confined to the low millimeter to sub millimeter emission ranges (i.e. as low as about 0.1 mm). The provided high powered voice coil (which is located within a housing adapted in size and shape for hand held use) is operatively linked to the proximal "non-active end" of the vibratory shaft of the variant research vibrator ("variant 2"). The vibratory shaft is thereafter projected through the housing, enabling removable attachment to any of the attachment interfaces described according to the invention. The variant research vibrator is also powered in like fashion to the preferred vibrator 10 (as described above); through AC power cord and removable DC battery pack. The variant research vibrator is of preferred use in conjunction with simultaneous ultrasonic imaging (as per the dual function system—described earlier), as the low displacement amplitude signal at higher frequencies requires direction and the establishment of a sonic penetration window, to ensure therapeutic penetration to target vascular areas within the patient 20.

It should be understood that the choice of a voice coil is not critical to enable vibration therapy in the 1-1000 Hz range, and a high powered peristaltic linear motor for example with frequency and power (or force/stroke) control, may alternatively be employed. An exemplary peristaltic linear motor may be comprised of a magnetostrictive material optimally incorporating Terfenol D. Alternatively, a linear stepper motor assembly could be used independently, or in conjunction with the magnetostrictive material.

A variant "light weight" vibrator (i.e. "variant 3"—not shown) is also provided according to the invention (described later), which enables maximum displacement amplitude emissions limited to 10 mm deflections with sufficient power to enable operation under engagement forces to the body surface of the patient 20 of up to about 50 N. Variant light weight vibrator 10 ("variant 3") is of like design to vibrator 10, but is of lighter weight (i.e. with a smaller, less powerful linear stepper motor) and is thereby better suited for self administration by the patient 20, who may be too weak to hold a heavier device.

Yet another variant "heavy duty" vibrator (i.e. "variant 4"—not shown) of like design to vibrator 10 but of greater weight and of higher power (i.e. with a larger, more powerful linear stepper motor) is provided for obese patients (or when the backside of the patient 20 is utilized) and will not dampen its oscillations when engagement forces of significantly greater than 100 N are applied.

The preferred vibrator 10 is of a size and weight well suited for clamp 100 engagement, belt engagement (described later) or engagement by the hand of an operator preferably via a double-handed technique. The variant lightweight vibrator ("variant 3") is of a size and weight well suited to single hand or double handed engagement. The variant heavy duty vibrator ("variant 4") is of a size and weight more suited to clamp 100 engagement, or engagement by both hands of an operator.

The variant heavy duty vibrator ("variant 4") is well suited for use with obese patients, or in cases where the backside of the patient 20 is utilized (described earlier), wherein higher displacement amplitudes and engagement forces may be required to ensure therapeutic penetration.

The housing 14 of vibrator 10 (and all provided variants) is advantageously made of ABS Cycolac (™) material, however any alternative durable and lightweight material (such as polycarbonate or stainless steel) may be used.

The preferred vibrator 10 (and provided variants) is powered by battery or power cord at a range of voltages (e.g. North America—110, 120 V, Europe—220V, Japan 95, 105 V, Australia 240 V) and is (as stated) operable both by battery and power cord for emergency settings. The vibrator 10 (plus all provided variants), cumulatively enables a selection means for a range of frequencies in increments of 0 (off), 1, 5, 10, 20, 30, 40, 50, 60, 70, 80, 90, 100, 110, 120, 150, 200, 300, 400, 500, 600, 700, 800, 900 and 1000 Hz (although other variations in frequency selection may be employed).

Detachable contacts 12 are provided in a plurality of sizes, (i.e. small, medium and large), and made substantially of silicone rubber, however any resilient yet non-obtrusive material (preferably shaped with a convex contact surface), to allow comfortable application against the body of patient 20 may be used. The contacts 12 are sized to make contact with an intercostal space of the human body, and rest evenly against the upper and lower rib, with an outward dome shaped convexity to ensure soft tissue contact and concentrate vibration therapy effectively. The preferred contact 12 advantageously comprises a semi spherical dome shape, with a flat planar circular base (the base being of similar size to the head of a stethoscope), wherein the base ranges in size between 2 cm, 3 cm and 4 cm diameter. It should be understood that the exact shape of contacts 12 (i.e. a semi spherical dome) is not critical, and that any convexly shaped contact head may be used, as long as efficient seating within the intercostal spaces of the patient 20 is enabled. Optionally, a variety of contacts comprising suction cups (not shown) are provided to enable an additional active retraction force, provided the patient 20 is not significantly diaphoretic. A soft rubber lining (or more specifically, a vinyl lining with foam rubber underlay of known type) may optionally overly the engagement surface of contacts 12 in order to impart a more comfortable application (which is especially useful for extremely tender skinned females with fleshy breast tissue who often are very sensitive to pressure applications to the chest wall). It should also be understood that the exact size of contacts 12 is not critical, and a selection of variant contacts (not shown) with even smaller contact surfaces may be used, enabling a direct seating within the rib space of the patient 20 such that the ribs themselves are minimally or not touched. This manner of chest wall contact provides a more comfortable application for some individuals.

The preferred embodiment comprises a pair of adjustably spaced contacts 12, separated by bifurcated connector 13 which is attached to shaft 16 of vibrator 10, to provide concentrated therapy (preferably) to either side of sternum at the selected intercostal space as per the prescribed methodology. Alternatively, to avoid unnecessary bruising (or trauma) to the chest wall, a solitary contact 12 (either attached directly to shaft 16 or via the variant connector—described earlier) placed leftward the sternum can be utilized, this method particularly suitable in cases of known Anterior or Lateral AMI (i.e. wherein leftward coronary involvement is diagnosed). In a further variation, to optimize sonic penetrability to the heart and to account for variable location of the heart within the thoracic cavity, a plurality beyond a pair of contacts 12 may be used. In this case, bifurcated connector 13 further utilizes the incorporated support structure 24 (depicted in FIG. 4), to allow for the addition of up to two slide-able and lockable sleeves 23, wherein each sleeve 23 incorporates a pair of support arms 22, with each support arm disposing at least a single contact 12. Placement of the plurality beyond a pair of contacts 12 could be, for example along, or just lateral to the anatomic right and left sternal border, encompassing the 3rd, 4th and 5th intercostal spaces. In yet another variation, variant connector 19 disposing two pairs of adjustably spaced contacts 12, may be applied to bridge the sternum along the 3rd and 4th intercostal spaces, along the 4th and 5th intercostal spaces, or even along the 3rd and 5th intercostal spaces of the patient 20.

To maximize sonic penetrability in particular to the left anterior descending artery, the vibrator 10 and chosen attachment interface may be placed more anatomically leftward with respect to the patient 20, such that one or more contacts 12 will interface with the left mid clavicular line (or thereabouts). Alternatively, any one of the utilized contacts 12 may be slide-ably placed more laterally along any one of the chosen anatomically leftward oriented support arms 22 (i.e. relative to patient 20), with the position of vibrator 10 remaining substantially over the sternum of patient 20. In yet a further variation, stimulation of the left mid clavicular line of the patient 20 may be ensured via the use of a second vibration device with second attachment interface, preferably running in phase with the vibrator 10 (or equivalent) to avoid destructive interference of the vibratory signal Referring again to FIG. 7, peripheral devices to variant cardiac phase controlled vibrator 11 ("variant 1") are required for use of the "advanced method" variation of the invention. The advanced method is specifically designed for cardiac use, to enable cardiac phase controlled vibration therapy (timed in accordance to the cardiac cycle) and the optional use of frequency algorithms to optimize the system.

Display monitor 52 (located remote to the housing of variant cardiac phase controlled vibrator 11<"variant 1">) receives output from variant interface 51, and peripheral physiologic sensors (as specified below) via variant processor 35. Display monitor 52 displays: ECG 36 output (up to three leads, e.g. V lead (anterior), Lead II (inferior) and V5 (lateral)); a digital readout of heart rate; external accelerometer 39 wave form output comprising the delivered surface vibration displacement amplitude on the vertical axis in (mm), and a real time display moving right to left at 25 mm/second to match the waveform output of ECG 36 in real time on the 'horizontal' axis; the waveform output of optional impedance plethysmograph 40 also moving in real time to match the output of ECG 36 (to monitor relative real time blood pressure, and inspect for timing of diastolic therapy); optional phonocardiography system 42 signal trace; the chosen frequency and mode of delivery (written annotations); the chosen displacement amplitude of the therapy (written annotation); and optionally a noninvasive blood pressure wave form output also moving in real time to match ECG 36 wave form output via noninvasive blood pressure apparatus 44 arterial tonometry, to support an absolute value to the otherwise relative plethysmography wave form analogue. As an alternative to arterial tonometry, a noninvasive automatic blood pressure cuff system may be used, wherein a periodic digital readout of systemic blood pressure may be displayed on display monitor 52.

Variant interface 51 comprises a combination of an electronic control touch screen and keyboard entry which is (as stated previously) also located remote to variant cardiac phase controlled vibrator 11 ("variant 1"), and is preferably placed alongside display monitor 52 and variant processor 35 on a portable work bench or stand (not shown). Variant interface 51 enables the reception of input from the operator and supplies the interface with variant processor 35. Variant interface 51 is adapted to receive and transmit information relating to: the mode of vibration to be delivered (i.e. continuous, or diastolic only vibration); the displacement amplitude of vibration (0 off, 1-15 mm displacements); the displacement amplitude of vibration according to cardiac phase (0 off, 1-15 mm displacements); the frequency of vibration (0 off, 1-120 Hz); the frequency according to cardiac phase; the displacement wave form type (i.e. sinusoidal, square, saw tooth or exponential); the fine tuning control of vibration emission timing (or "vibration emission timing control"); the preferred ECG 36 lead to be utilized for determining or "tracking" the QRS complex via variant processor 35; and an electrocardiographic low pass frequency filter (i.e. with 40 Hz cutoff) suitable for eliminating muscle tremor and vibrational artifact from the resultant ECG 36 trace prior to processing via variant processor 35.

Variant processor 35 receives information from the physiological monitoring and sensing equipment and variant interface 51, and provides output to display monitor 52 and variant cardiac phase controlled vibrator 11 ("variant 1"). A preprogrammed, default rate related time delay tracking the deflection of the QRS complex (used to signify and electronically trigger the onset of diastolic vibration) is provided by variant processor 35 programmable control. Variant processor 35 thereby is enabled to determine systolic and diastolic phases based on ECG 36 output. The beginning of the diastolic phase of vibration is further adjustable by the operator according to an additional operator input (or vibration emission timing control) to variant interface 51, based on information gained by physiological timing parameters as viewed on display monitor 52. These timing parameters are represented by; the wave form produced by accelerometer 39 on shaft 17 (which defines the timing and amplitude of the applied vibration), the wave form produced by ECG 36 (which defines the beginning of systole via the onset of the QRS complex), and optionally impedance plethysmograph 40 (which defines the beginning of diastole via the dichrotic notch of the arterial wave form analogue). As a further option, phonocardiogram 42 is used to define with more exacting precision the onset of diastole (i.e. via the initial split of the "S2" heart sound signifying closure of the Aortic Valve). Phonocardiogram 42 however is not useful in continuous mode vibration therapy because of the continuous vibration noise, which contaminates the signal. In the case where both impedance plethysmograph 40 and phonocardiography system 42 are not employed, the onset of diastole can be approximated as (and/or verified by) the termination of the T wave as seen on the waveform output of ECG 36. Variant processor 35, upon receiving input from variant interface 51, and upon receiving information from the physiological monitoring and sensing equipment, will process the information and provide output to variant cardiac phase controlled vibrator 11 ("variant 1") which applies the selected timing, mode, displacement wave form, frequency and displacement amplitude of vibration therapy.

ECG 36 comprises a six electrode system, with a left arm, left leg, right arm, right leg (ground) and an anterior pre-cordial lead (modified V lead preferably placed on the sternum) and a lateral pre-cordial lead (V5). Output from leads 11, modified V lead, and V5 are preferably displayed on display monitor 52. Any lead may be selected for variant processor 35 automatic tracking of the QRS complex, with the lead presenting with the tallest QRS complexes and/or relatively smallest T waves preferred to ensure appropriate tracking and avoid "double counting". In an option, a pair of ECG electrodes may be advantageously incorporated within or mounted upon the contact surfaces of the contacts 12, to enable an expedited means of obtaining electrocardiographic information.

Impedance plethysmograph 40 requires the placement of two electrodes on the arms of the patient 20 and the application of a minimal current in order to monitor relative changes of blood pressure in real time, checking, for example, for any beneficial inotropic effects with diastolic only vibration in cardiogenic shock patients, or sudden deterioration of blood pressure during treatment in an otherwise hemodynamically stable case of evolving myocardial infarction. The present invention employs a Tektronix™ type 3C66 impedance plethysmograph system; however any known impedance plethysmography system may be used for plethysmograph 40. Impedance plethysmograph 40 is also employed to check the timing of the closure of the aortic valve and therefore the beginning of diastole, and is useful to confirm or to facilitate the manual adjustment (or vibration emission timing control) of the default rate related time delay set after sensing of the QRS complex to ensure that diastole is captured properly in the timing algorithms. Alternatively, a variant photo plethysmograph (such as the Tektronix™ Plethysmography Pulse Sensor) placed to the finger or forehead of the patient 20, with wave form signal output to display monitor 52 (to inspect for inotropic changes) may be employed. Impedance plethysmograph 40 is preferable as it yields a closer analogue trace of a central arterial wave form (i.e. yielding an closer approximation of the true timing of Aortic Valve closure via the dichrotic notch) than the variant photo plethysmograph which incorporates an analogue trace of a peripheral arterial wave form.

Phonocardiogram 42 is of a commercially known type, consisting of a small microphone placed on the chest wall which provides output to display monitor 52 representing the heart sounds in time with ECG 36, plethysmograph 40 and accelerometer 39 signals. The heart sound "S1" represents the onset of systole, and the initial component (or "split") of the heart sound "S2" represents the onset of diastole. Phonocardiogram 42 can with extreme precision, provide the timing of aortic valve closure marking the onset of diastole, however the device is limited to diastolic only mode vibration therapy as continuous mode vibration contaminates the audio trace.

Noninvasive blood pressure apparatus 44 comprises a modern state of the art arterial tonometry noninvasive blood pressure monitoring system (i.e. Pilot arterial tonometry device manufactured by Colin Medical Instruments Corp.). Optionally, a noninvasive blood pressure monitor, comprising a blood pressure cuff system which takes a periodic blood pressure reading from the arm of the patient 20 and displays the information on display monitor 52, may be used. Vibration therapy, in this latter example, may be programmed to temporarily cease during the measurements of the blood pressure cuff system to avoid interference in the audio blood pressure measurements.

External accelerometer 39 (i.e. Shin Nipon Sokki C. Ltd Emic 540) is placed on shaft 17 of variant cardiac phase controlled vibrator 11 ("variant 1") to monitor the timing, frequency and displacement amplitude of emitted vibration from variant cardiac phase controlled vibrator 11 ("variant 1"). Optionally, transesophageal accelerometer 38 (i.e. Shin Nipon Sokki Co. Ltd Emic 540M) placed on a transesophageal lead is used to monitor chest wall penetration of low frequency vibration to behind the heart. Alternatively, any commercially available miniature accelerometers can be used for either application.

A strain gauge force transducer (not shown) or optionally a weight scale to indicate the engagement force of contact or contacts 12 against the chest wall (or other body part) of the patient 20 is optionally provided.

It should be understood that the location of variant interface 51, display monitor 52 and variant processor 35 relative to variant cardiac phase controlled vibrator 11 ("variant 1") is not critical to enable use of the advanced method, and is provided as separate distinctly located elements (e.g. on a portable workbench) only to facilitate operative links between the instruments and necessary sensing and monitoring equipment which may be quite extensive (especially in the case wherein all possible sensing and monitoring equipment are utilized). For example, in an alternative embodiment, variant cardiac phase controlled vibrator 11 may be altered to comprise a functionally self contained operator held unit (or device), comprising a display means (such as a LED display on the housing of the device), a control means (such as control switches on the handle of the device), a cardiac phase monitoring means (such as an ECG monitor operable in conjunction with or as part of the device), a vibratory emission monitoring means (such as an accelerometer system placed on a vibratory component of the device or alternatively a vibration emission indicator), and a processing means (such as a microchip or other programmable logic controller located within the housing of the device). This "self contained" arrangement of the cardiac phase controlled vibration delivery system may be advantageous to an operator (or paramedic) in the field, wherein maneuverability and ease of portability of the utilized apparatus are important factors towards expediency and effectiveness in emergency situations.

Figure 9:
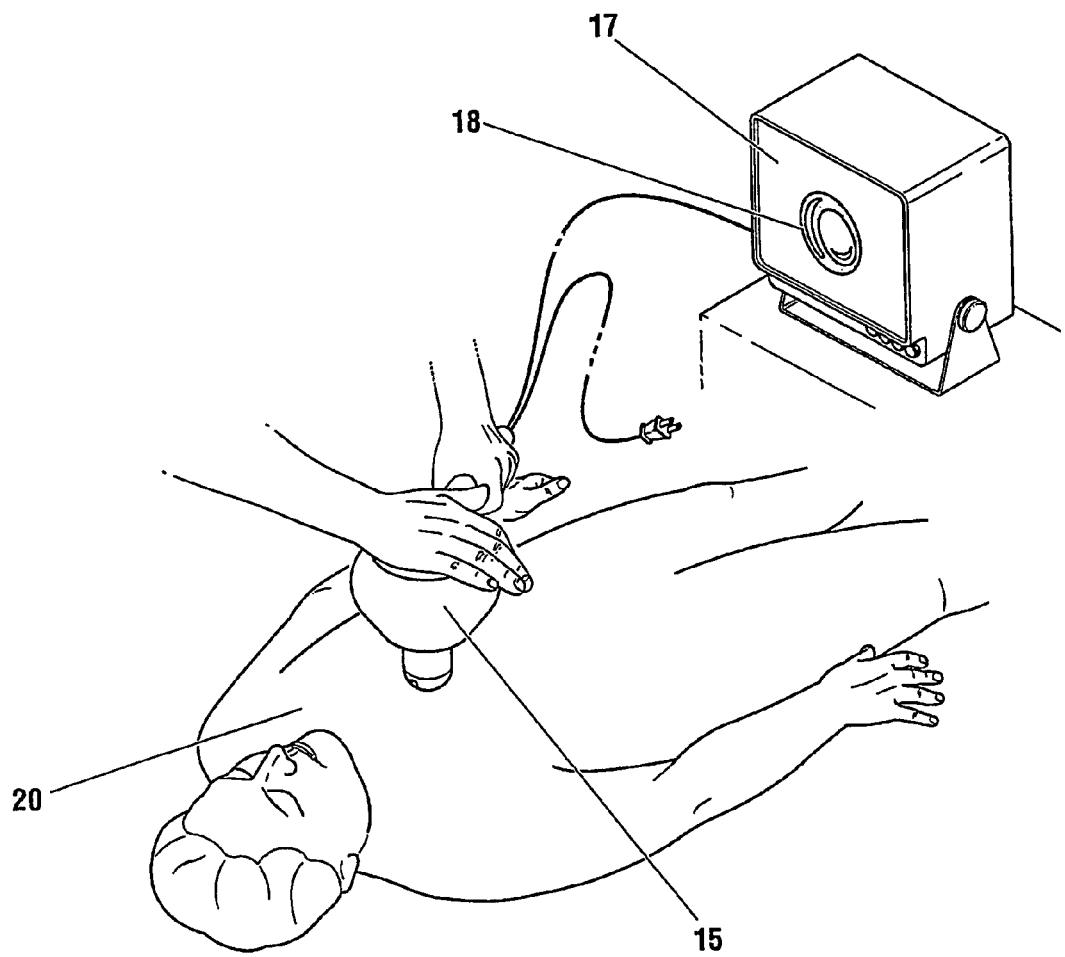
FIG. 9 is a perspective view of a variation of the vibrator incorporating ultrasonographic imaging with treatment vibration via a hand held technique according to the invention.

Referring now to FIG. 9, a perspective view of a variation of the preferred embodiment, a hand held single imaging/treatment probe (herein set forth as the "variant dual function imaging vibration device 15"), and method as applied to the patient 20 is shown. This system (as per the "dual function system" described earlier) employs both low frequency vibration and high frequency ultrasonographic imaging (HFUS) taken together in concert (simultaneously) via a single combined hand held transmission unit, for visually directing low frequency vibration therapy within the body of the patient 20. The attachment interface of variant dual function imaging vibration device 15 contains an ultrasonic imaging transducer (not shown—located at the active end of variant dual function imaging vibration device 15, proximate patient 20), whereby an image can be viewed on ultrasonographic 2-D display 17. The ultrasonic imaging transducer is operatively connected (or acoustically coupled) to a low frequency vibration source (also not shown—located within the housing of dual function imaging vibration device 15) such that upon activation, when the low frequency vibration source generates vibration, the ultrasonic imaging transducer vibrates and thereby is enabled to deliver low frequency vibration simultaneously (i.e. together in real time) with HFUS imaging, all via a shared contact surface to the patient 20. An optional weight added within or exterior to the housing of variant dual function imaging vibration device 15 (weight not shown), adds inertia to the system to ergonomically assist the operator (i.e. to apply engagement force) during hand held placement of dual function imaging vibration device 15. An example of a useful ultrasonic image 18 (in this case an image of the heart is depicted), is shown on ultrasonographic 2-D display 17.

The vibration source of the variant dual function imaging vibration device 15 advantageously comprises the same active components of preferred vibrator 10 (described earlier), and thereby enables selectable displacement amplitude and selectable displacement wave form control within a 1-120 Hz range. It should be understood however that this particular selection of vibration source is not critical to enable use of the dual function system, and any known vibration source operable to generate vibration within the 1-1000 Hz range (so long as the therapeutic vibration wave form does not disable or interfere with the necessary ultrasonic imaging wave form) may be used, regardless of the level of provided vibratory emission control. Such vibration sources may for example comprise but not be limited to; linear stepper motors, linear stepper motors with displacement amplification, linear (non-stepper) motors, rotary motors with a rotary to linear conversion element such as a cam or crank, eccentrically spinning weights, magnetostrictive actuators, voice coils, shakers (e.g. with or without neodymium magnet transducers), and ceramic servo motors coupled to either a rotary (with cam) or linear stage. The preferred vibration source should be operable at high force or displacement amplitude settings while under load, such as to optimally enable a high energy penetrative system of vibration therapy (or oscillatory or percussive therapy by other name).

Figure 10:
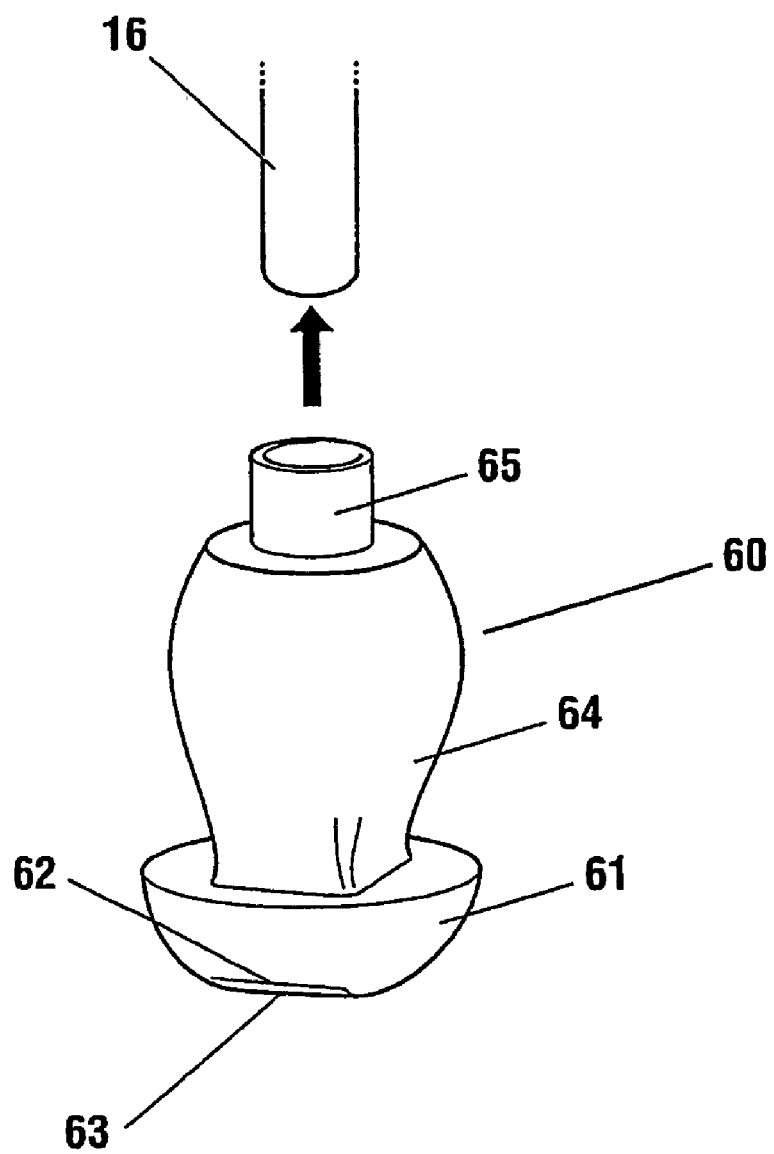
FIG. 10 is a perspective view of a variant ultrasonic imaging contact according to the invention.

In a variation to the above dual function system (i.e. apparatus), a simply adapted ultrasonographic imaging transducer is provided, which is readily incorporated for use as an attachment interface via removable attachment to shaft 16 of vibrator 10. In reference to FIG. 10, this variation of the dual function system utilizes variant "ultrasonographic imaging" contact 60, advantageously comprising semi spherical silicone dome 61 attached to and partially encapsulating a distal active end of a pediatric HFUS imaging transducer of known type. Rectangular slit 62 is centered at the curved "distal", contact surface of semi spherical silicone dome 61 to provide for a minimal protrusion of engagement face 63 (or imaging contact surface by other name) of the pediatric HFUS imaging transducer. This arrangement enables stable contact of both engagement face 63 (i.e. for imaging), and the distal contact surface of semi spherical silicone dome 61 (i.e. for improved seating and transmission of low frequency vibration) to the chest wall, or other body part, of the patient 20. The "proximal" end (i.e. away from patient 20) of variant ultrasonographic imaging contact 60 comprises housing 64 for the electronic components of the provided pediatric HFUS imaging transducer. Hollow connecting column 65 is attached to and projected from housing 64, which enables removable attachment (by friction) to shaft 16 of vibrator 10 (or to the shaft of any of the provided variations to vibrator 10 according to the invention), however any known means of attachment (fixed or removable) may be used, as long as a sound vibratory connection is established. In this variation to the dual function system, shaft 16 once activated, vibrates connecting column 65, which vibrates housing 64 for the electronic components of the pediatric HFUS imaging transducer, which in turn vibrates attached semi spherical silicone dome 61 and engagement face 63, which taken together comprises variant ultrasonographic imaging contact 60. The electronic control cord (not shown) of the pediatric HFUS imaging transducer is optionally removably secured to the exterior surface of housing 14 of vibrator 10. The electronic control cord is thereafter removably attached to an ultrasound imaging apparatus (not shown) of known type; however any commercially available ultrasonic imaging apparatus may be adapted for use.

It should be understood that while ultrasonographic imaging contact 60 of the dual function system incorporates the use of a partially encapsulating structure (i.e. semispherical silicone dome 61) disposed about the provided distal active end of the pediatric HFUS imaging transducer to improve contact and transmission of the low frequency therapeutic vibration, this arrangement is not critical, and the pediatric HFUS imaging transducer (or any other known ultrasonic imaging transducer) may be optionally applied alone (or by any other means), directly to the skin surface of the patient 20, without such an accompaniment. Furthermore, while a pediatric variety of HFUS imaging transducer is preferred because of its smaller size (i.e. to enable optimal rib space application), alternatively, any known ultrasonic imaging transducer adapted in size and shape to enable human contact (preferably of a size to enable seating within a rib space) may be adapted for use.

As a further option of enablement to the dual function system (and yet another variation), an ultrasonic imaging probe (or preferably variant ultrasonographic imaging contact 60 as described above) may be adapted for attachment to the anatomically leftward oriented (relative to patient 20) attachment site of bifurcated connector 13 of vibrator 10 (or alternatively any equivalent bifurcated attachment interface stemming from any low frequency vibration source operable to generate vibration in the 1-1000 Hz range). This arrangement enables ultrasonic imaging guided placement via the preferred pair of attachment sites (i.e. to the chest wall of the patient 20), wherein the ultrasonic imaging transducer (or variant ultrasonographic imaging contact 60) is placed to an application site on the patient 20 comprising a determined feasible sonic penetration window (as per the methods described earlier), which will usually be near the sternal margin, at the anatomically leftward third, fourth or fifth intercostal space. The opposing (or anatomically rightward oriented contact, which may or may not comprise an ultrasonic imaging transducer), is preferably placed anatomically rightward to the sternum at the same determined intercostal level, or optionally one intercostal spacer lower (or inferior) as per the methodology described earlier. It should be understood that the incorporation of one, or more than one ultrasonic imaging transducer may be used, in any number of orientations according to the invention (i.e. depending on the style of attachment interface selected).

A "multifunction system" is also provided, which in addition to providing a means of transmission for low frequency vibration therapy concurrently and simultaneously with ultrasonic imaging via a single transmission instrument (i.e. as above in the "dual function" system), further enables a LFUS treatment wave form emission. A variant "ultrasonographic imaging and LFUS treatment" contact (not shown) adapted for removable attachment to shaft 16 of vibrator 10 (and provided variants), with low frequency ultrasonic treatment emission capabilities as well as high frequency ultrasonic imaging capabilities, is provided. The variant ultrasonographic imaging and LFUS treatment contact comprises an ultrasonic phased array imaging transducer mounted upon and acoustically coupled to the active surface of a low frequency ultrasonic transducer (both of known types), such as to enable transmission of the LFUS treatment wave form emission through the active components of the ultrasonic phased array imaging transducer, and thereby to the patient 20. The low frequency ultrasonic transducer (or ULFUS transducer") component of the multifunction system advantageously comprises a piezoelectric actuator which is operational to emit a frequency at 27 kHz, which is a frequency known for its superior tissue penetration characteristics and thrombo-disruptive properties (although other LFUS frequencies within the range of 20-100 kHz may be used, via the incorporation of alternate piezoelectric actuators). The LFUS transducer and ultrasonic phased array imaging transducer assembly work together simultaneously and nondestructively, to supply continuous high resolution imaging with HFUS and simultaneous treatment with a LFUS wave form, all in conjunction with low frequency (i.e. sonic to infrasonic range) vibration therapy.

Variant ultrasonographic imaging and LFUS treatment contact, (as with variant ultrasonographic imaging contact 60—described earlier), is also removably attached to shaft 16 of vibrator 10 (or provided variant) by friction via a hollow connector (not shown), wherein in this case, the hollow connector is attached to the "proximal" non-active end of the LFUS transducer electronic housing. Alternatively, any known attachment means (removable or fixed) may be used, as long as a stable vibratory connection is established. A first electronic control cord joins the variant ultrasonographic imaging and LFUS treatment contact to an ultrasonic imaging device, and a second electronic control cord joins the variant ultrasonographic imaging and LFUS treatment contact to a LFUS control apparatus to enable an operator control of the function of the LFUS transducer of the multifunction system. A selectable duty factor between 1% and 100%, plus a selectable intensity level of between 0.5 W/sq. cm and 25 W/sq. cm is provided to the operator via the LFUS control apparatus. The preferred LFUS treatment waveform comprises a frequency of 27 kHz, with a 100% duty factor emission at maximum tolerable intensity by the patient 20 in emergency situations. A temperature probe (not shown) is optionally attached to the periphery of the engagement face of the variant ultrasonographic imaging and LFUS treatment contact (which equates to the active contact surface of the provided ultrasonic phased array Imaging transducer) in order to supply a readout such that the operator can adjust the duty factor and/or intensity levels of the LFUS treatment when (or if) the temperature at the tissue interface rises to an unacceptable level to avoid burning of the skin of the patient 20. Alternatively, the variant ultrasonographic imaging and LFUS treatment contact may be exchanged, with the application skin surface cooled down by a wash cloth or ice bag in between variant ultrasonographic imaging and LFUS treatment contact exchanges. In this multifunction system embodiment, noninvasive low frequency vibration (i.e. in the sonic to infrasonic range), low frequency treatment ultrasound, and high frequency ultrasonic imaging are utilized nondestructively in concert (i.e. simultaneously) to provide an optimized therapy system for acute vascular obstructions and treatment of ischemic events, optimally employed as an adjunct to systemically delivered drug therapy, to improve localized drug effectiveness.

It should be understood that while the low frequency vibration source to the multifunction system advantageously comprises the active components of preferred vibrator 10 (i.e. to enable a high degree of low frequency vibration control), this selection of low frequency vibration source Is not critical to enable use of the multi function system according to the invention, and any known vibration source operable to generate vibration within the 1-1000 Hz range (so long as the therapeutic vibration wave form does not disable or interfere with the necessary ultrasonic imaging wave form, or therapeutic low frequency ultrasonic wave form) may be used, regardless of the level of provided vibratory emission control. Such vibration sources may for example comprise, but not be limited to: linear stepper motors, linear stepper motors with displacement amplification, linear (non stepper) motors, ceramic servo motors coupled to either a rotary (with cam) or linear stage, rotary motors with rotary to linear conversion elements, eccentrically spinning weights, magnetostrictive linear motors, voice coils, and shakers (e.g. with or without neodymium magnet transducers).

Furthermore, it should be understood that the type of LFUS transducer of the multifunction system may be varied and a magnetostrictive actuator operable within the 20-100 kHz range may be used in the stead of the provided piezoelectric actuator. Also, while the embodiment shown (i.e. apparatus) provides a "variant ultrasonographic imaging and LFUS treatment contact" with an end to end acoustic coupling between the provided LFUS transducer and provided ultrasonic phased array imaging transducer (i.e. such that the emitted LFUS wave form is transmitted through the active components of the ultrasonic phased array imaging transducer), alternatively other structural variations are possible to enable use of the multifunction system. For example, an ultrasonic imaging transducer may be disposed around or alternatively placed side by side to an incorporated LFUS transducer, such that the active ends (or engagement faces) of both units are directly adjacent to one another and thereby sharing a common application surface for contact to the patient 20. Treatment applicators of similar design to this are discussed in U.S. Pat. No. 5,558,092 to Unger et al., incorporated herein by reference. The relative geometry (i.e. ultrasonic imaging transducer disposed about the LFUS transducer (or vice versa) and the relative contact surface areas of the two complimentary engagement faces are not critical, as long as both the active contact surface of the LFUS transducer and the active contact surface of the ultrasonic imaging transducer are represented to a sufficient degree to enable their respective functions, and are placed in close proximity to one another. Preferably the shared contact surface provided would be of a size, and shape, to enable efficient seating in a rib space of the patient 20, to optimize use in transthoracic applications.

As the cost of incorporation of an ultrasonic phased array imaging transducer to enable ultrasonic imaging for low frequency vibration directed therapy may be prohibitive in some medical centers, a more cost effective LFUS therapy concurrently with the transmission of low frequency vibration therapy (i.e. a "dual therapy"), without ultrasonographic imaging capabilities is provided. This "dual therapy" option to the present invention comprises a variant "LFUS treatment" contact (not shown), adapted for removable attachment to shaft 16 of vibrator 10 (or provided variants thereof, wherein a semi spherical silicone dome advantageously attaches and partially encapsulates a distal, active end of a low frequency ultrasound transducer which is operational at 27 kHz (although any low frequency ultrasonic transducer operational within the 20-100 kHz range, which is adaptable in size and shape to enable seating within a rib space may be used. A rectangular slit is centered at the semi spherical silicone dome's curved contact surface to provide for a minimal protrusion of the distal, active surface of the low frequency ultrasound transducer's distal, active end which is advantageously slide-ably engaged there through. This arrangement enables stable contact of both the distal, active surface of the low frequency ultrasound transducer and the curved contact surface of the silicone dome, such as to enable optimal transmission of low frequency vibration and the LFUS therapeutic signal to the chest wall (i.e. within the rib spaces) and/or other body part treated. Optionally, the distal, active surface of the low frequency ultrasound transducer is adapted in size and shape, such as to seat uniformly within a selected rib space of the patient 20, and thus eliminating the need of an accompanying silicone dome, which serves only to optimize seating and transmission of the low frequency vibration aspect of the dual therapy. The non-active "proximal" end of the variant LFUS treatment contact the housing for the electronic components of the provided low frequency ultrasound transducer, wherein a hollow connecting column is attached which enables removable attachment of variant LFUS treatment contact to shaft 16 of vibrator 10 (or provided variants thereof). In this LFUS dual therapy option, shaft 16, once activated, vibrates the connecting column which thereafter vibrates the housing for the electronic components of the low frequency ultrasound transducer, which in turn vibrates the attached distal, active surface of the low frequency ultrasound transducer and the attached silicone dome, which taken together, comprises the variant LFUS treatment contact. The simultaneous delivery of a low frequency ultrasonic wave form and low frequency vibration therapy (i.e. in the sonic to infrasonic ranges) via a common application surface is thus enabled.

Alternatively, in a variant assembly, a pair of LFUS treatment contacts are slide-ably and lock-ably mounted along the length of a variant bifurcated connector (not shown), such as to enable bridging of the sternum of the patient 20, as per the preferred method of attachment in cardiac applications. In still-another variant assembly, a plurality beyond a pair of LFUS treatment contacts may be employed to enable placement to a plurality of intercostal spaces.

Like in the aforementioned "multifunction system" a selectable duty factor of between 1% and 100%, and selectable intensity level of between 0.5 W/sq. cm and 25 W/sq. cm, is provided to the operator via a LFUS control apparatus in the LFUS dual therapy system. A temperature probe placed at the periphery of the active contact surface of the low frequency ultrasound transducer (i.e. wherein the active contact surface interfaces with the skin of the patient 20) is optionally provided with a readout, such that the operator can adjust the duty factor and intensity levels when (or in the temperature at the tissue interface rises to an unacceptable level to avoid burning of the skin of the patient 20. Alternatively, the variant LFUS treatment contact may be exchanged, with the application skin surface cooled down by a cool wash cloth or ice in-between variant LFUS treatment contact exchanges.

The provided low frequency ultrasound transducer in the dual therapy variation employs a piezoelectric actuator, however alternatively a magnetostrictive element (preferably operational within the range of 20-100 kHz), may be used to enable the method and dual therapy system. It should also be understood that while the embodiment shown (i.e. apparatus—the LFUS treatment contact) preferably incorporates the use of a partially encapsulating structure with a slit disposed about the provided low frequency ultrasound transducer, this arrangement is not critical and the low frequency ultrasound transducer may be optionally applied alone (or by any other means), directly to the skin surface of the patient 20, without such an accompaniment. In this "dual therapy" option, low frequency vibration (i.e. in the sonic to infrasonic range) and low frequency ultrasound (without high frequency ultrasonic imaging) are utilized nondestructively in concert to provide an optimized therapy system for acute vascular obstructions and ischemic events, optimally employed as an adjunct to systemically delivered drug therapy to improve localized drug effectiveness.

In the preferred embodiment, (which utilizes low frequency vibration solely in the sonic to infrasonic ranges), vibrator 10 is secured to patient 20 by the hand or hands of an operator, wherein an alternative means of engagement employs use of clamp 100.

Figure 11:
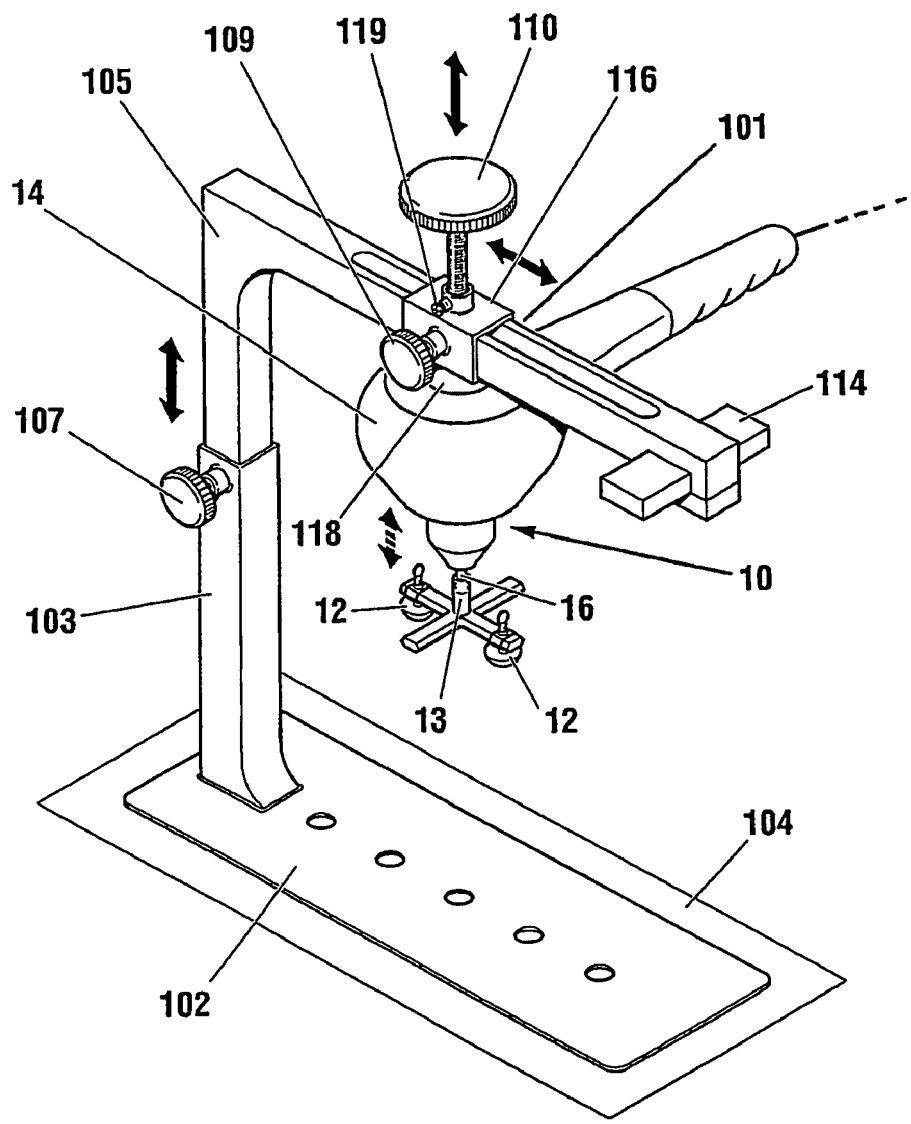
FIG. 11 is a perspective view of a variation of the clamp mechanism according to the invention.

Referring now to FIG. 11, a perspective view of a variation of clamp 100, namely "clamp 101" is shown. Clamp 101 is used to attach vibrator 10 to the chest wall for cardiac applications or for any body part. The clamp 101 is made of steel, but may alternatively be made of aluminum or any other suitable material which can supply sufficient strength and stiffness to maintain the necessary position of vibrator 10 and application force to patient 20. Clamp 101 optionally comes with board 104, which can slide underneath a supine patient's back. Base 102 is preferably placed on top of board 104. A vertical hollow bar 103 extends at substantially 90 degrees from base 102. An extendable arm 105 extends horizontally from hollow bar 103, and can be slide-ably moved up and down hollow bar 103 to accommodate different sizes for patient 20. Once positioned extendable arm 105 is locked in place to hollow bar 103 with locking knob 107, however other mechanisms such as a clip or notch may be used. Extendable arm 105 in this variation is non-rotatable about the longitudinal axis of hollow bar 103 and advantageously comprises an angle bracket to provide a more stable platform for vibration therapy. Weight 114 is optionally placed on extendable arm 105 to add further inertia to clamp 101 if required. Sleeve 116, which articulates with and supports vibrator 10, is slide-able along extendable arm 105. Sleeve 116 includes locking knob 109, which tightens to lock vibrator 10 in place along extendable arm 105. Vibrator 10 is selectively lowered and raised with engagement screw 110, which articulates with and vertically transverses sleeve 116 via a vertical screw column (not shown). Engagement screw 110 comprises an upper end disposing a turning knob, and a lower end that attaches the proximal, non-active end of housing 14 of vibrator 10. Set screw 119 is provided to abut against engagement screw 110 thereby locking it in place during operation. Rotatable circular piece 118 in articulation with the lower end of engagement screw 110 and disposed at the surface within the non-active end of housing 14 is provided such that housing 14 may remain stationary while engagement screw 110 screws vibrator 10 up or down. The exact dimensions of the components of clamp 101 (or 100) are not critical, as the height of the vertical support of vibrator 10 and the horizontal distance of vibrator 10 along extendable arm105 (and arm 108) is made adjustable.

The force of engagement of vibrator 10 is optionally evaluated by a strain gauge force meter (not shown) or in a variation a weight scale (not shown). Optionally, a pivoting, rotating and locking universal joint (not shown), located at the juncture between the non-active end of the housing 14 and the lower end of engagement screw 110, allows for the adjustment of the correct angulation and orientation of vibrator 10 relative to engagement screw 110, to ensure a perpendicular contact between the attachment point of the contacts 12 and the chest wall (or other body part treated), wherein the patient 20 may not always rest perfectly supine or lying flat. Universal joint adjustments comprising angulations of less than or equal to 20 degrees (i.e. from the axis of the engagement screw 110) are recommended to ensure structural stability of clamp 100 or 101 engagement of vibrator 10 to the selected treatment body surface of the patient 20.

In both the clamp 100 and 101 variation of engagement, an emergency quick release system comprising a mechanical lever (not shown) disposed to the underside of sleeve 116 is provided such that the screw column which is internalized within the vibrator sleeve 116, can be quickly disengaged by the mechanical lever from engagement screw 110, thus (once quickly releasing set screw 119) liberating vibrator 10 from the patient 20. Alternatively, a quick unlocking and detachment means (not shown) of vertical bar 106 (and/or hollow bar 103) and the horizontal arm 108 (and/or extendable arm 105) may be provided in the clamp 100 and 101 variation, to allow an alternative means of quick release. An electrical shutoff switch (not shown) is provided to both clamp 100 and 101, in case of emergency.

Figure 12:
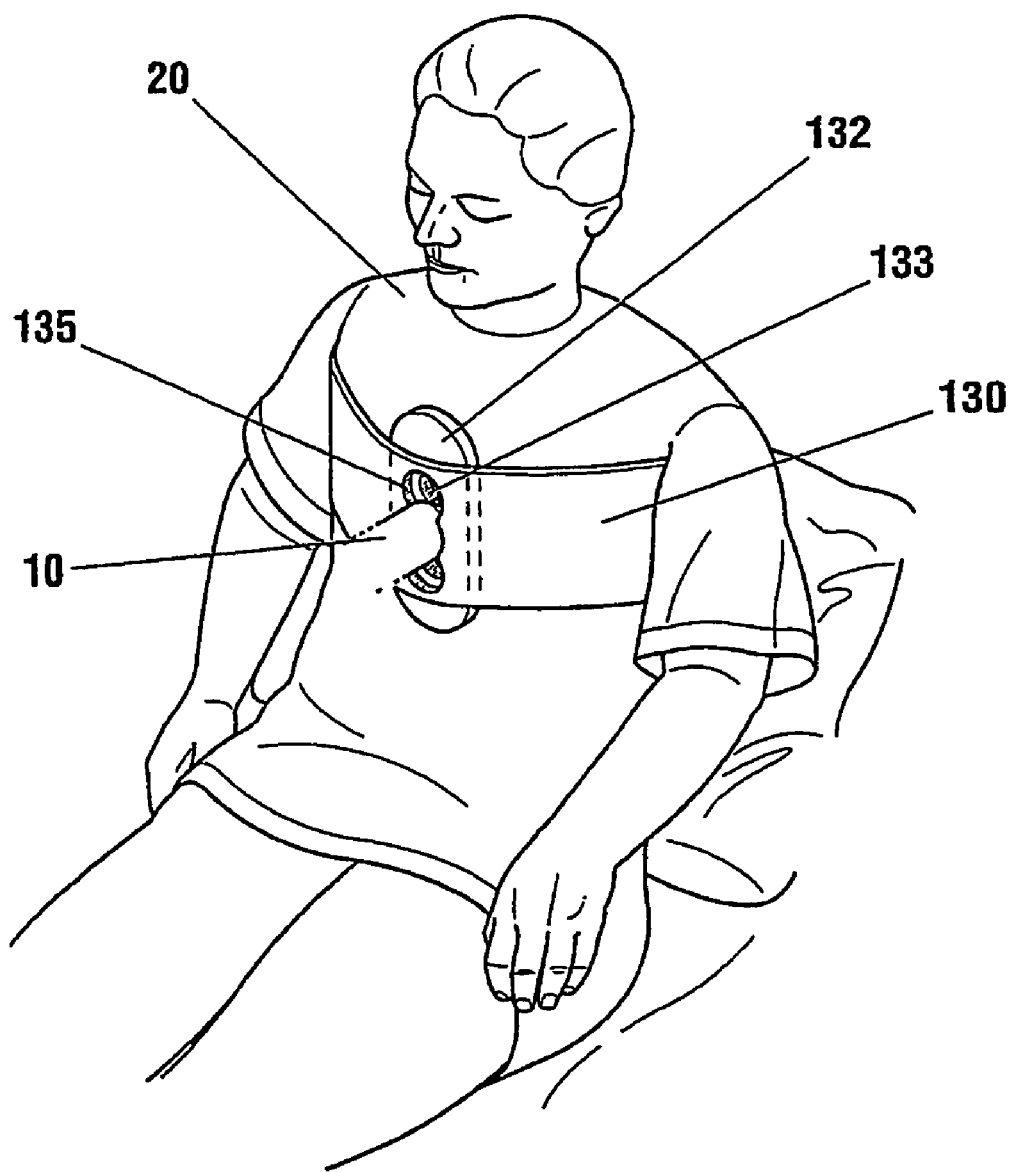
FIG. 12 is a perspective view of a patient in fowler's position receiving treatment from a belt engaged vibrator according to the invention.

Referring now to FIG. 12, a belt 130 variation of attachment means to the chest wall of the patient 20 is shown wherein patient 20 is (in this case) sitting upright in Fowler's position (emergency use of IV's, nasal prongs and monitoring equipment according to the preferred embodiment is not shown). Belt 130 is comprised of semi-flexible poly carbonate plastic, selectable in various curves to accommodate varying sizes of chest for patient 20. The polycarbonate material may optionally be transparent. Alternatively, belt 130 may be comprised of any other flexible material, which is highly resistant to longitudinal strain (such as reinforced leather, nylon or vinyl). Belt 130 is adapted to overly substantially flat central panel 132, which is made lightweight and stiff in material and design. Central panel 132 is located to match an area on the chest of patient 20 over the sternum. Central panel 132 is provided in various sizes to accommodate different chest wall dimensions and will optimally cover the 2nd to 6th intercostal spaces of the patient 20. The distal, cone shaped, active end of housing 14 of vibrator 10 is attached and stabilized through slit 133 within central panel 132, having sides defined by a series of holes with semicircular edges, such that the vibrating attachment surfaces of contact or contacts 12 of vibrator 10 make contact with the target site or sites (not shown in FIG. 12) on the patient 20. Slit 133 within central panel 132 has beveled edges (not shown) which taper inwards towards patient 20 to match the beveled distal active surface of the conical head of housing 14 of vibrator 10. Central panel 132, by means of the operator selecting the appropriate location in slit 133, will allow for variable placement of housing 14 of vibrator 10 and contact or contacts 12 to differing intercostal spaces according to the optimal placement established by the operator (according to the methods described earlier). Belt 130 covers the central panel 132 and partially encircles the torso of the patient 20 such that the ends of belt 130 extend up to and not beyond the front side of the mid-axial line of the patient 20 (or, in other words, up to and not beyond the anterior half of the torso of patient 20). Alternatively, in the flexible belt 130 variations, belt 130 is preferably longer and is adapted to substantially encircle the torso of the patient 20. Central panel 132 further includes a means of securing vibrator 10 comprising slide-able and insert-able bolts (not shown) adapted to snap into corresponding slots (not shown) located at the distal, active end of housing 14 to thereby lock vibrator 10 in place. Belt 130 further comprises matching (but slightly larger) belt slit 135 to slit 133 in central panel 132, to further cradle the beveled distal active end of the housing 14 of vibrator 10, such that the proximal, non active end of housing 14 is projected away from the patient 20. The securement means of belt 130 to the backside of the patient 20 is enabled through utilization of a bungee cord (not shown), which is selectable in varying lengths and diameters. The provided bungee cords have ends comprising metal hooks, which are made securable to reinforced holes (not shown) placed near the ends of belt 130. Optionally, the securement means of belt 130 may comprise any highly elastic material which allows for an appropriate degree of strain and recoil under load, in order to allow for expansion of the chest of the patient 20 during inspiration while still maintaining adequate tension to belt 130 and thereby maintaining adequate engagement force (i.e. at least 5-10 N, preferably 20-100 N, and optimally 50-100 N) to central panel 132 (and thereby vibrator 10) to enable the application of vibration therapy regardless of phase of respiration of the patient 20. Fine tuning of the engagement force to the chest wall of patient 20 is provided to the operator by an inflatable bladder (not shown) which is removably placed (while deflated) to the underside of the securement means of belt 130, preferably to the hollow between the shoulder blades of the patient 20 once the bungee cord securement (or variation thereof is secured in place. The operator (which may in this case be or include the patient 20) incrementally inflates (or deflates) the inflatable bladder until the desired engagement force of vibrator 10 to the chest wall of patient 20 is achieved (i.e. about 10-20 N, and preferably about 20 N in expiration, and less than or equal to about 100 N in inspiration).

A force meter (not shown) is also optionally provided to determine and monitor engagement force of contact or contacts 12 against the chest wall (or other body part) of the patient 20. The maximum engagement force tolerable to the patient 20 is recommended, so long as vibrator 10 does not dampen (or stop) its oscillations from too great an engagement force, and the patient 20 can breathe freely, and tolerate the vibration therapy within a determined or predetermined safety limit). Belt 130 once secured with adequate tension, will provide appropriate engagement force to central panel 132, which in turn supplies appropriate engagement force to vibrator 10, (and contact or contacts 12—not shown in FIG. 12) to enable the application of vibration therapy to the chest wall of the patient 20, or alternatively the backside or any body part of patient 20. The design of belt 130 is advantageous as the patient 20 when nauseous may sit up or roll over during vibration therapy.

Variant securement means of belt 130 to the backside (or contra lateral untreated side) of the patient 20 is obtained by a resilient, substantially inelastic pair of Velcro™ straps (not shown), but may as a further variant comprise a pair of like securement straps with holes connected by a tang (not shown), or as a further option a pair of securement straps connected by a tightenable friction buckle (not shown). In this resilient, substantially inelastic variant securement system (which is preferable for body parts which do not substantially change size or shape), the same bladder, (which has a greater length than the securement strap's width) is removably centered to the underside of the secured inelastic straps, once the straps are fastened. Again placement of the bladder is preferably to the hollow of the back between the shoulder blades of the patient 20 for chest wall applications, or to the contra lateral (or diametrically opposed) untreated side to the body part treated. In addition to the provision of a control means for engagement force, the bladder (which is made of a semi compliant material), will buckle slightly at the securement site while under load hence providing a degree of compliance to the otherwise substantially non yielding variant securement means which (unlike the preferred bungee cord rubber securement means) is highly resistant to longitudinal strain, thereby enabling the chest of the patient 20 to expand and relax with respiration in transthoracic applications. The advantage to the Velcro™ straps variant securement system, while less compliant and thus offering less comfort to the patient 20 during inspiration in transthoracic applications, is that it provides for the most stable platform to central panel 132 for engagement of vibrator 10 to the chest wall (or any other body part treated).

Other variations to the engagement system of belt 130 such as a halter, strap, sling or vest (i.e. for sitting up or ambulation), may be adapted to the present invention by those skilled in the art of vibration or percussion garment manufacture, to enable support and necessary engagement force for the relatively high amplitude vibration therapy to be applied to the anterior chest wall of the patient 20 while in an upright position. The present invention provides a set of removable, and length adjustable shoulder straps (not shown) which connect with belt 130 via reinforced alligator clips, such as to provide vertical support to belt 130 engagement when the patient 20 is in the upright position. Alternatively, any other commercially available or adaptable means of shoulder strap attachment is acceptable. The garment variations will allow fixation of vibrator 10 (or provided variant) to the target site upon the anterior region of the chest wall (i.e. overlying the mediasteinal cavity), while allowing patient 20 movement or even ambulation during vibration therapy.

It should be understood that the above described variation of engagement means for belt 130 (and all variations thereof can be utilized or adapted for any body part, and not just to provide engagement to the thorax of the patient 20, and may also be adapted to provide support to other suitable vibrators (or percussion instruments by other name), and not just the preferred vibrator 10 (or provided variations thereof.

Mobile, Emergency Response System for Paramedic Use:

For first line response by paramedics in an ambulance or before transportation, a self-contained, mobile, emergency, response kit for the treatment of acute, thrombotic and/or vasospastic vascular obstructions, including a selection of drugs, drug delivery supplies, and the preferred vibrator 10 (with a selection of attachment interfaces to enhance vibration transmission and effectiveness) is provided. The mobile, emergency response kit may also be employed by nurses and/or physicians in the Emergency room, upon arrival of the patient 20 to hospital. The preferred application is for acute coronary vascular obstructions, yielding a diagnosis of Acute ST elevation Myocardial Infarction.

The mobile, emergency response kit includes:

a) Vibrator 10 (with bifurcated connector 13 and a set of removably attached contacts 12 of varying size), b) Portable, compartmentalized storage carrying case, c) Drugs, d) Drug delivery supplies, e) Portable high powered DC battery pack, (operational with vibrator 10), f) A pair of sleeves 23 (each sleeve 23 incorporating an additional pair of support arms 22) for optional attachment to bifurcated connector 13, g) Variant Connector 19 with a pair of variant sleeves 27, h) Variant non bifurcated connector, i) Variant ultrasonographic imaging contact 60, and portable ultrasonic imaging device plus ultrasonic conducting gel, and j) Xylocalne 2% (for optional freezing of the skin surface treated).

Optional provisions for the mobile, emergency response kit include:

a) Clamp 100 (engagement means), b) Variant clamp 101 (engagement means), c) Belt 130 system (engagement means), d) Variant LFUS treatment contacts with variant bifurcated connector and LFUS control apparatus, e) Variant ultrasonographic imaging and LFUS treatment contact with LFUS control apparatus, f) Variant peripheral contact heads with semi malleable attachment interface, g) Cardiac phase controlled vibration delivery system comprising; variant cardiac phase controlled vibrator 11 ("variant 1"), ECG monitoring system 36, variant processor 35, display monitor 52, variant interface 51, and external accelerometer 39, h) Variant research vibrator ("variant 2"), i) Variant light weight vibrator ("variant 3"), j) Variant heavy duty vibrator ("variant 4"), k) Larger, portable, compartmentalized storage carrying case, and l) Set of helmet attachment means comprising helmets of various sizes.

The preferred vibrator 10 for the mobile, emergency response kit is operable to emit vibration within the 1-120 Hz range, and provides a selection of displacement wave form emissions (i.e. sinusoidal, square, saw tooth, and exponential waves), with a maximum displacement amplitude of up to 15 mm. Vibrator 10 is operational under engagement forces of up to about 100 N, such as to enable a high energy, deeply penetrating emergency system of vibration therapy. Vibrator 10 runs on AC power via a power cord, or alternatively by battery power via a high powered removable and interchangeable DC battery pack.

The variant research vibrator ("variant 2") is of optional inclusion to the mobile emergency response kit, and offers a higher range of vibration frequencies within the range of 1-1000 Hz. The variant research vibrator ("variant 2") has a limited displacement amplitude enablement (i.e. in the low millimeter to sub millimeter ranges) and is primarily used for research purposes (i.e. in the 150-1000 Hz range) and/or use with variant ultrasonographic imaging contact 60 for directed vibration therapy. Also, the variant light weight vibrator ("variant 3"), and the variant heavy duty vibrator ("variant 4"), are both optionally included. The variant heavy duty vibrator is particularly effective in cases where high engagement forces are required to ensure therapeutic penetration, such as when the patient 20 is obese, or when the upper back (or posterior thoracic region) of patient 20 is utilized as an application site (as described earlier). The variant light weight vibrator ("variant 3") is preferable if the patient 20 is utilized to engage the device, or self administer the vibration application.

The mobile, emergency response system comprises a self contained system, employing a module and portable storage carrying case (not shown) which houses the components of the mobile emergency response kit. A variant larger portable storage carrying case (not shown) is adapted to additionally house optional components.

The mobile, emergency response system enables systemic drug delivery, via intravenous, intra arterial, subcutaneous, oral, topical and nasal drug administration means. Drugs within the mobile, emergency response kit include: thrombolytic agents (e.g. ACTIVASE™ (Alteplase), TNKase™ (Tenecteplase), RETAVASE™ (Reteplase), Abbokinase™ (Urokinase), Kabikinase™ (Streptokinase with water), Streptase™ (Streptokinase with 0.9% NaCl solution), Lanoteplase); GP 2b 3a platelet inhibitors (e.g. ReoPro™ (Abciximab), AGGRASTAT™ (Tirofiban hydrochloride), Integrelin™ (Eptifibatide)); calcium channel blockers (e.g. ISOPTIN™ SR (Verapamil HCl), ADALAT XL™ (Nifedipine), Cardize™ (Diltiazem), NORVASC™ (Amlodipine besylate); Nitrates (Nitroglycerine (spray, pill or patch), isosorbide dinitrates (Isordil™ and Sorbitrate™), Nipride™ (Nitroprusside); Oral anti-platelets (e.g. Acetylsalicylic Acid (Aspirin), Plavix™ (Clopidogrel), TICLID™ (Ticlopidine hydrochloride); Anti-coagulants such as heparin; and concentrated oxygen. It should be understood that the mobile emergency response kit may contain any one of the above listed drugs, or any number of the above listed drugs in any combination.

Non-pharmacological "drugs" such as echo contrast agents (i.e. micro bubble solutions which lower the cavitational threshold of a medium), which may be delivered systemically along with other IV drugs, are optionally included in the mobile, emergency response kit to enhance the agitative internal effects of externally delivered vibration therapy. Optional cavitating micro bubble solutions within the mobile, emergency response kit include: EchoGen™ (Dodecafluoropentane emulsion), Albunex™ (5% human albumin), LEVOVIST™ (Galactose Palmitic Acid ultrasound contrast agent), Air containing albumin microcapsules (Quantison™ and Myomap™), SonoVue™ (Sulfurhexafluoride) and Perfluorocarbon containing microbubbles (Perfluorocarbon exposed sonicated dextrose albumin PESDA). Cavitating microbubbles solutions are particularly effective in conjunction with joint LFUS administration, and are readily implemented in conjunction with use of the variant LFUS treatment contacts, or variant ultrasonographic imaging and LFUS treatment contact, as per the "dual therapy" or "multifunction system" methods of LFUS administration as described earlier.

Drug delivery supplies within the mobile, emergency response kit include: IV tubing, IV start kits, sterile IV introduction needles, tape, IV pole, 0.9 NaCl IV solutions, Dextrose IV solutions, Code 8 IV solutions, Heparinized IV solutions, IV pressure bag with pressure gauge and pressure bulb, sterile intra arterial introduction needles, guide wires, sheaths with dilators, scalpel blades, one way stopcocks, three way stop cocks, sterile drapes, sterile gowns, sterile gloves, sterile skin preparation solution, needles adapted to subcutaneous drug delivery, alcohol swabs, paper cups, straws, sublingual sprays, aerosol sprays, oxygen tank, ambubag, oxygen tubing, oxygen mask, and nasal prongs. It should be understood that the mobile emergency response kit may include any one of the above listed drug delivery supplies, or any number of the above listed drug delivery supplies in any combination.

The variant ultrasonographic imaging contact 60 (with a portable hand carried ultrasonic imaging device—not shown), is also provided to the mobile, emergency response kit, so a skilled operator (when available) can optionally establish a viable sonic penetration window and target the culprit vascular region (directly or by anatomic reference) with low frequency vibration with optimal efficiency. Variant ultrasonographic imaging contact 60 is readily adaptable for use in all provided variations of vibrator 10 (i.e. as per the "optional provisions" listed above), and is of preferred use when a trained operator is available, and with the variant research vibrator ("variant 2"), whereby a directed approach for higher frequency lower displacement amplitude vibration (i.e. above 150 Hz) is generally required to ensure therapeutic levels of penetration to the culprit region targeted.

The variant ultrasonographic imaging and LFUS treatment contact is also optionally provided to the mobile, emergency response kit to enable the application of ultrasonic imaging, low frequency vibration, and low frequency ultrasound (as a second therapeutic wave form) simultaneously and in concert via the multifunction system (as previously described). For cost effectiveness, a pair of variant LFUS treatment contacts (with variant bifurcated connector), enabling emissions of low frequency ultrasound without imaging capabilities (i.e. without the use of a relatively expensive incorporated ultrasound imaging transducer—as per the "dual therapy" option) is also optionally provided. The IV or IA administration of cavitating microbubbles, with or without other helpful drug agents (e.g. as per the methods disclosed in U.S. Pat. No. 5,695,460, said being incorporated herein in toto by this specific reference thereto) are recommended as an adjunct low frequency vibration and joint LFUS wave form delivery.

The cardiac phase controlled vibration delivery system is optionally included within the mobile, emergency response kit for treatment of Acute Myocardial Infarction complicated by cardiogenic shock. A cardiac phase "mode" selection enables cardiac phase dependent vibration delivery, wherein "mode" defines the timing of emission of vibration therapy according to cardiac phase (i.e. systole vs. diastole). The selection of vibration mode enables the application of vibration specifically during the diastolic phase of the cardiac cycle, which is useful in AMI cases which have deteriorated to cardiogenic shock as diastolic vibration, besides agitating and assisting dissolution of the culprit coronary obstruction, is also known to provide a positive inotropic effect. The provided cardiac phase dependent vibration delivery system is optionally programmable to enable the selection of varying frequency of vibration according to cardiac phase. It is advantageous to for example vibrate the myocardium between 20-60 Hz (and optimally 50 Hz) during ventricular diastole (approximating the diastolic resonance frequency of the myocardium) and to vibrate the myocardium between 70-120 Hz (and optimally 100 Hz) during ventricular systole (thereby approximating the systolic resonance frequency of the myocardium which is stiffer in systole). Higher frequencies at same displacement amplitude are generally known to improve blood clot disruption and induce cavitation and acoustic streaming, thus taking advantage of the myocardium's higher vibration resonance frequency during the systolic period (or debatably at any time throughout the cardiac cycle) is advantageous.

For the sake of simplicity and ease of portability, the mobile, emergency response kit of the present invention incorporates only the mandatory elements to enable the aforementioned cardiac phase controlled vibration delivery system wherein ECG 36, variant processor 35, variant interface 51, display monitor 52, external accelerometer 39, and variant cardiac phase controlled vibrator 11 ("variant 1"), is all that is utilized to enable cardiac phase controlled vibration delivery. The deflection of the QRS complex from ECG 36 is interpreted by variant processor 35 (which defines the timing of the onset of "ventricular systole"), and a rate related timing delay is thereafter applied following the QRS complex (which defines the timing of the onset of "ventricular diastole"). Variant processor 35 is thereby enabled to respond to operator inputted cardiac phase modulated vibration algorithms and therein provide output commands to variant cardiac phase controlled vibrator 11 ("variant 1"), to enable the delivery of cardiac phase dependent time and optionally frequency varying vibration therapy. The operator, upon viewing the ECG 36 and accelerometer 39 output on the display monitor 52, can adjust (or fine tune) the timing of vibration emission via the variant interface 51. Ideally diastolic vibration should commence from the terminal end of the T wave, and then discontinue upon the onset of the deflection of the QRS complex as visualized by the provided ECG 36 wave form. As stated the use of the "advanced method" is of significant importance when the patient 20 is suffering from an acute coronary vascular obstruction which has deteriorated to a state of cardiogenic shock.

In a variation, the variant cardiac phase controlled vibrator 11 may be adapted to provide a self contained operator held unit (i.e. complete with control means, processing means, display means, cardiac phase monitoring means, and vibration timing indication means—as described earlier), such as to enable a more easily portable and expedited cardiac phase controlled vibration delivery system to the mobile, emergency response kit.

Further options to the mobile, emergency response kit include an engagement means (i.e. clamp 100 or clamp 101, and/or belt 130 system) so that an operator need not hold vibrator 10 (or provided variant) by hand throughout the course of vibration therapy. A retractable IV stand (not shown) is optionally incorporated within and extending from bar 106 of clamp 100. In another variation of clamp engagement, bar 106 (i.e. in clamp 100) and/or hollow bar 103 (i.e. in clamp 101) may be placed and supported directly to the stretcher of the patient 20 by a vice grip or other locking mechanism (i.e. rather than to base 102), or, arm 108 (i.e. in clamp 100) and/or extendable arm 105 (i.e. in clamp 101) may be alternatively supported by a portable unit with lockable wheels or directly to a wall or fixture in the emergency room or within the ambulance.

It should be understood that while the mobile, emergency response kit advantageously employs the preferred vibrator 10 (such as to enable a high degree of operator enabled vibration emission control), this employment (or choice of vibrator 10) is not critical in the mobile, emergency response system and alternatively any known (or adaptable) low frequency (i.e. operational in the 1-120 Hz range) vibrator (or percussion, or oscillation device by other name), with a suitable attachment interface for selected body surface contact (preferably enabling concentrated delivery of vibration between the rib space or spaces of the patient 20), being operable at high displacement amplitudes (i.e. >2 mm, and preferably >4 mm deflections) and engagement forces (i.e. >5-10 Newtons, and preferably >20 Newtons), may alternatively be used, regardless of the level of operator enabled vibration control.

It should similarly be understood that cardiac phase controlled vibration delivery according to the mobile, emergency response system may be embodied (by apparatus) in many ways, and should not be restricted to the system herein described. Any low frequency vibrator (or vibration system), preferably operable at a high displacement amplitude (i.e. greater than 2 mm and preferably greater than 4 mm deflections) and high engagement forces (i.e. at least 5-10 N, and preferably greater than 20 N), which is adapted to provide cardiac phase controlled vibration delivery (i.e. with vibration timing emission algorithms and optionally vibration frequency algorithms) may be used. The apparatus may comprise a plurality of separately located elements (as provided), or may alternatively comprise a single, self contained operator held instrument (as described earlier).

Figure 13:
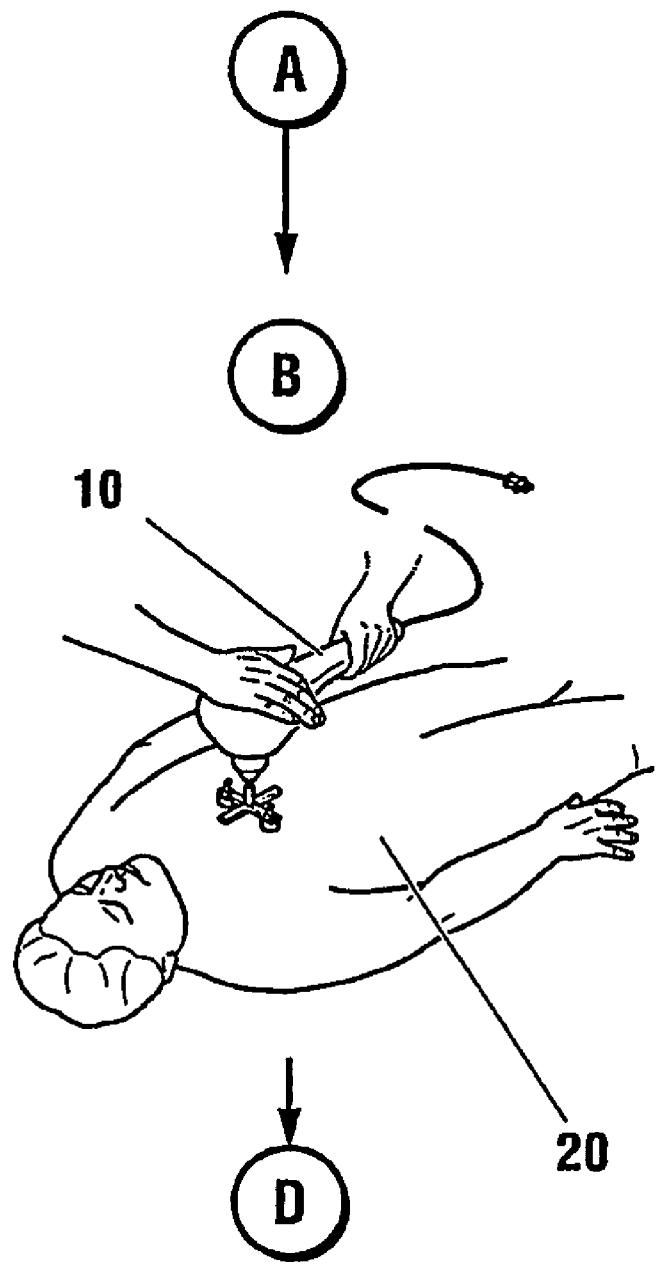
FIG. 13 is a schematic diagram of the preferred vibration method for the remediation of acute thrombotic vascular obstructions according to the invention.

Referring now to FIG. 13, the preferred method of employment of the vibrator 10 (or percussion device by other name) for treatment of acute vascular obstructions is schematically shown. Step (A) comprises the step of systemically administrating at least one and preferably a plurality of useful drugs adapted for treatment of an acute vascular obstruction which is usually a combination of thromboses and vessel spasm. Such drugs may include but not be limited to thrombolytics, GP 2b 3a platelet inhibitors, nitrates, anti coagulants, oral anti-platelets, concentrated oxygen and morphine. Step (B) comprises the step of applying vibration to a selected or pre-determined external body surface deemed proximate the acute vascular obstruction via the preferred vibrator 10 (or other suitable percussion device as described above). Application by vibrator 10 is preferred in the case where the operator has no specialized skill or training in ultrasonic imaging (which would be the most common scenario in the field or in the ER). Engagement to the anterior chest wall bridging the sternum is shown (which is preferred in acute myocardial infarction cases, although the backside of the patient and other areas upon the chest wall may also be utilized), and ideally the highest force or displacement amplitude deemed safe and tolerable to the patient 20 is selected to ensure optimal penetration and effectiveness of the percussive signal. Step (D) comprises the provisional step of employing diastolic timed vibration via the cardiac phase controlled vibration delivery system (or any suitable variation thereof) in the special case wherein the patient 20 deteriorates into a state of cardiogenic shock or cardiac failure, which is not uncommon in acute myocardial infarction cases. Diastolic timed vibration is known to reduce LV diastolic pressures and promote a positive inotropic effect to LV function. Otherwise "continuous" vibration may be continued or discontinued in accordance to a risk/benefit decision by a responsible operator. It should be understood that the initiation of vibration (B) may proceed or be concurrent with the administration of drug therapy (A). Furthermore, it should also be understood that vibration therapy (B) may alternatively be utilized alone without adjunctive drug therapy (A), such as in the special cases whereby drug therapy is not indicated (i.e. for patients with substantial bleeding risks or other co-morbid factors), drug therapy is not available (i.e. at home or in the field), wherein drug therapy is not allowed or not authorized (e.g. patient refusal, or in the case where the operator is not authorized to give drugs), and/or wherein drug therapy is not preferred or not prescribed.

Figure 14:
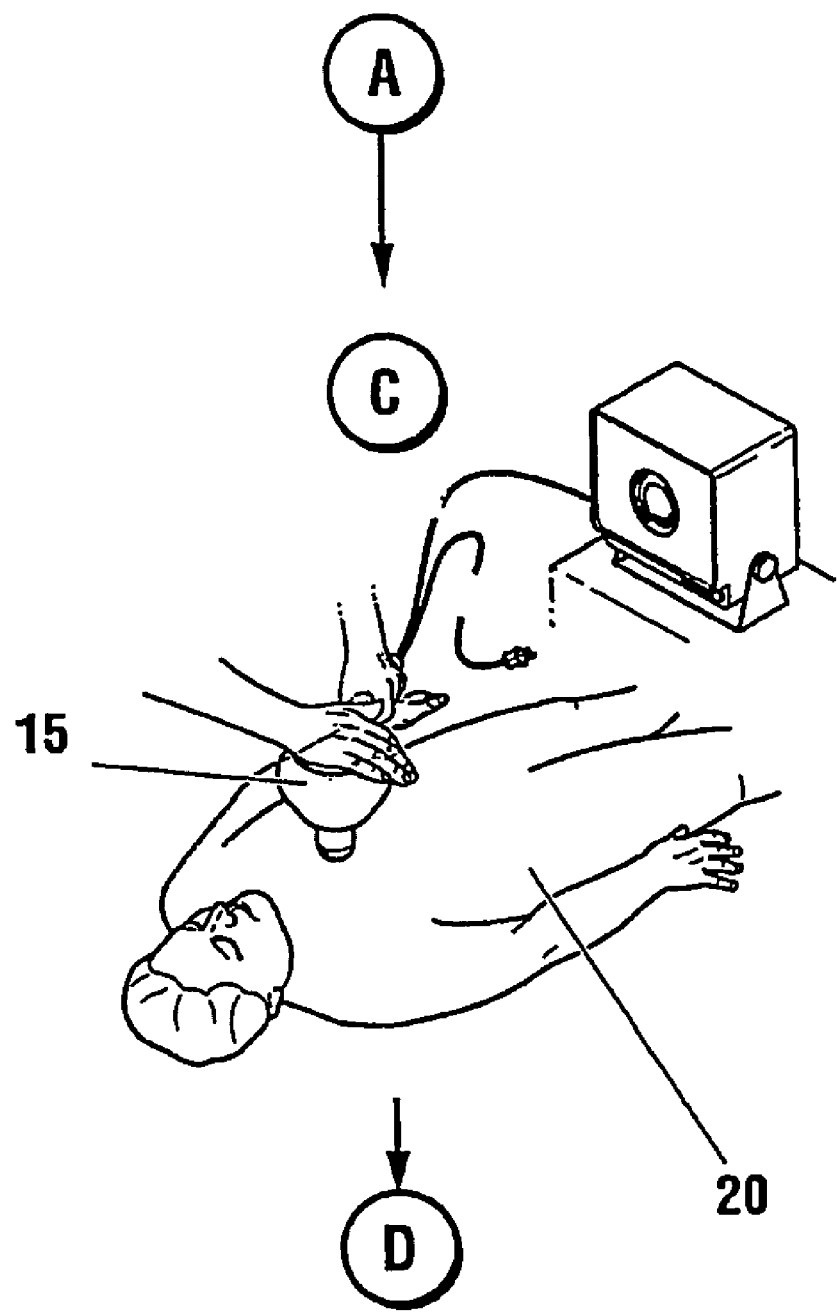
FIG. 14 is a schematic diagram of a variation to the preferred vibration method employing ultrasonic imaging to direct vibration.

In reference to FIG. 14, a variation to the preferred vibration method incorporating the employment of ultrasonic imaging to direct vibration is shown. Step (A) comprises the same step of systemically administrating a clot dissolving and/or vasodilatory drug to the patient 20 as per the prescribed therapy. Step (C) comprises the step of applying and directing vibration by means of ultrasonic imaging (i.e. the variant dual function imaging vibration device 15 applied to patient 20 is shown, however any suitable vibrator—as described above—coupled to an ultrasonic imaging transducer at its active end may be used). The variant dual function imaging vibration device 15 (or variation thereof is optimally placed and directed via ultrasonic imaging, to emit vibration towards an acute vascular obstruction targeted. This is accomplished by either direct visualization (e.g. such as visualization of a blood clot within a blood vessel) or by anatomic reference, wherein for example placement in proximity to the base of the heart, and visualization of the substantially akinetic, basal aspect of the myocardium wherein the culprit blood clot is likely to reside defines preferred placement and direction of vibration in acute myocardial infarction cases. Step (D) comprises the optional step of employing diastolic timed vibration via the cardiac phase controlled vibration delivery system (or suitable variation thereof) in the special case wherein the patient 20 deteriorates into a state of cardiogenic shock or cardiac failure. Again it should be understood that vibration therapy directed by ultrasonic imaging (C) may be independent of drug therapy (A), and may alternatively proceed or be initiated concurrently with the initiation of drug therapy (A).

In reference to the application of the mobile emergency response kit in the field, a tutored paramedic or physician, once arriving to the patient 20 and establishing a diagnosis, preferably selects at least one drug based upon clinical need and/or patient 20 bleeding risks, systemically administers the drug (or drugs), and then transcutaneously vibrates the body surface of the patient 20 deemed to overly the general area of the acute culprit vascular obstruction. As stated a skilled imaging approach to direct vibration may be employed if the operator has the skill and training required to recognize pertinent ultrasonic images, otherwise the preferred vibrator 10 (or other suitable non-imaging vibrator) with a pair or optionally a plurality beyond a pair of contacts 12 should be utilized. Low frequency vibration in the sonic to infrasonic ranges (i.e. 1-120 Hz; preferably 20-120 Hz in cardiac applications), or at any frequency within the 1-1000 Hz range may be used. Generally, the default frequency of 50 Hz sinusoidal vibration is preferred, as 50 Hz sinusoidal vibration can be delivered at a relatively high displacement amplitude, has excellent penetration characteristics through the chest wall and other body surfaces, falls within the resonance frequency of the heart, and is a well established frequency known to produce vascular dilation, cavitation, and acoustic streaming for encouraged clot disruption and increased drug mixing and permeation. Alternatively, square wave <b> (i.e. with a steep displacement rise for high impact, better penetration and disruptive action), saw tooth wave <c>, exponential wave <d> or any linear or nonlinear (or combination thereof) displacement wave form, may be used (see FIG. 8). Generally the maximum tolerable (and judged safe) force or displacement amplitude should be utilized in cases of acute myocardial infarction or acute vascular obstructions to the pulmonary or peripheral vasculature, wherein cell death, and/or hemodynamic compromise is otherwise imminent. A gentle 1-2 mm displacement amplitude may be preferable for the treatment of ischemic stroke (preferably via application of the contacts 12 of vibrator 10 to the posterior, posterior lateral or lateral aspect of the neck of the patient 20 or via the provided helmet attachment means) until a definite diagnosis of ischemic (or embolic) stroke is established, however higher treatment amplitudes may be considered as first line treatment according to a risk/benefit weighted decision (i.e. risk of cerebral hemorrhage vs. benefit of accelerated reperfusion) made by the attending clinician, or after the diagnosis of embolic stroke (i.e. vs. hemorrhagic) is established.

The patient 20 is transported to hospital or other treatment facility, preferably with vibration and drugs simultaneously delivered. The vibration therapy preferably continues until clinical signs of reperfusion are evident, or until an invasive corrective procedure such as emergency PCI (i.e. in heart attack cases) is established.

Portable, Emergency Response System for Outpatient Use:

For first line treatment of a citizen in the community (e.g. before the arrival of paramedics), a self-contained, portable, emergency response kit for the treatment of an acute thrombotic coronary vascular obstruction at early stage is provided. Components of the portable emergency response kit include the variant lightweight vibrator ("variant 3"), and preferably at least one anti anginal medication to be delivered. The portable, emergency response kit is designed to be utilized by the patient 20 as an emergency tool for self administration (or assisted administration by a non-trained or indeterminately trained bystander) within the community.

The portable, emergency response kit comprises a black leather portable carrying case which is adapted to house and port: the variant lightweight vibrator <"variant 3"> (including bifurcated connector 13 with a set of removably attached contacts 12 of various sizes), a portable DC power pack, an AC power cord, preferably at least one anti-anginal medication (such as Nitro spray, Nitro pill, Nitro patch, Isordil™, and/or Sorbitate™), and optimally at least one oral antiplatelet medication (such as Acetylsalicylic Acid, Plavix™, and/or TICLID). A larger brown leather carrying case is adapted to additionally house and port a small oxygen canister and nasal prongs to enable the administration of concentrated oxygen to the patient 20, as well as a small portable blood pressure device adapted to take blood pressure from the wrist of patient 20. The belt 130 engagement system (i.e. with inflatable bladder, bungee cord securement and, shoulder strap support—described earlier) may be provided so the patient 20 need not hold the unit by hand during the course of therapy. The patient 20 is instructed to carry a cellular phone at all times to enable calling for emergency assistance when necessary. The use of the variant lightweight vibrator ("variant 3") is preferable in the portable emergency response system as the unit is light weight and easy to "self" apply by the patient 20. As an option, the preferred vibrator 10 or variant heavy weight vibrator ("variant 4") may be alternatively selected, or any other low frequency commercially available vibrator (preferably offering vibration displacement amplitudes of greater than at least 2 mm) may be used according to the preference of the patient 20.

Vibration therapy is, in this case, employed for acute states of coronary insufficiency with symptoms consistent with infarction refractory to nitroglycerine treatment in the patient 20, wherein an acute coronary thrombotic obstruction (i.e. "Heart Attack") cannot be ruled out. Every bout of chest discomfort that the patient 20 in the community experiences might in fact be an acute coronary event wherein a plaque has ruptured and an acute thrombotic vascular obstruction has occurred.

The method of use of the portable emergency response system and kit comprises maintaining the portable emergency response kit in proximity of the patient 20 at all times. When a symptom of "angina" is felt by the patient 20 (i.e. chest pain or pressure, shortness of breath, nausea, diaphoresis, or "an impending sensation of doom"), patient 20 should undertake anti-anginal medical therapy as prescribed by his or her physician. In these cases, the patient 20 will try the prescribed anti-anginal medication such as nitro spray-.times.3 (i.e. with each dose spread 5 minutes apart), and upon recognition of no relief of chest discomfort (which may be quite severe), patient 20 will proceed to dial "911" wherein the diagnosis of an acute coronary thrombotic obstruction leading to an acute MI cannot be ruled out until a professional diagnosis is obtained. As described earlier, hyper acute early clot formation at early stage is extremely amenable to dissolution via mechanical agitation, hence a mechanically disruptive, agitative technique such as the application of high amplitude chest wall vibration therapy as herein described, is prospectively an extremely effective and important first line emergency method and tool. The patient 20 will rest and preferably additionally administer an oral antiplatelet medication (as above) as prescribed by a family physician or Cardiologist of the patient 20. The patient 20 should articulate the potential medical problem of a potential "heart attack" to bystanders such that patient 20 is not alone while waiting for the arrival of an ambulance and professional care (i.e. in the case of cardiac arrest). The variant lightweight vibrator ("variant 3"), or other selected vibrator is placed to the anterior chest wall preferably to bridge the sternum at the default level of the fourth intercostal space (although other attachment configurations are possible as per the methods described earlier). The blood pressure of the patient 20 may be monitored via the small portable blood pressure device, and oxygen may be administered until professional assistance arrives.

The chest wall interface of the variant lightweight vibrator ("variant 3") is advantageously accomplished via the bifurcated connector 13, preferably equipped with preferably a pair of pre sized contacts 12, wherein the contacts 12 have been pre adjusted in location on support arms 22 to optimally bridge the sternum and seat within the intercostal spaces of the patient 20 for maximum chest wall penetrability to the coronary circulation as per the methods previously described. Optionally, variant connector 19 disposing two pairs of support arms 22 (to enable four application sites via four contacts 12 to the patient 20), or bifurcated connector 13 disposing an additional two pairs of support arms 22 (to enable a total of three pairs of application sites via three pairs of contacts 12 to the patient 20) may be utilized for multiple intercostal space attachment, to enable maximal penetration of low frequency vibration to the deeply situated and variably located cardiovascular regions within the thoracic cavity.

The vibration displacement amplitude is preferably selected as the maximum tolerable to the patient 20, who should ideally be resting in either the supine position or seated comfortably in a chair. The optimal frequency is selected at 50 Hz continuously applied vibration with a sinusoidal wave form, however optionally any frequency within the 1-120 Hz range, or preferably 20-120 Hz range (i.e. to match the resonance frequency of the heart) and, square, exponential, or saw tooth displacement wave forms may be optionally selected according to the preference of the operator and/or prescribed therapy. Ideally a friend or bystander should engage the variant lightweight vibrator ("variant 3"), or other provided vibrator against the patient 20 by hand until professional care arrives. Alternatively, belt 130 with shoulder straps (or other variant garment, as described earlier) may be utilized, such that the patient 20 can self administer vibration therapy without the need to exert any effort to hold the variant lightweight vibrator ("variant 3"), in place. The patient 20 will preferably administer a dose of anti anginal medication such as nitro spray 0.4 mg SL (and optionally an oral anti platelet agent), and then proceed to administer adjunctive vibration therapy (as per the methods disclosed earlier) such as to provide a synergistic treatment system to assist localized drug effectiveness to the coronary vasculature. Monitoring of the blood pressure of the patient 20 (i.e. via the optimal small portable blood pressure device) is advantageous as repeated dosing of nitroglycerine (or other nitrate employed) may be accomplished barring hypotension during vibration therapy.

As an option, the variant lightweight vibrator ("variant 3"), or other selected vibrator, may be adapted to enable cardiac phase controlled vibration via the incorporation of an ECG monitoring system and suitable processing and control network (i.e. as a "self contained unit"—as described earlier), such as to enable the application of vibration restricted to the diastolic phase of the cardiac cycle of the patient 20 wherein it may be considered useful to provide a therapy which promotes a positive inotropic effect whereby the blood pressure and hemodynamic status of patient 20 may deteriorate (or will be unknown) until professional care arrives. The ECG monitoring system in this case may advantageously comprise at least a pair of electrodes operatively incorporated with or disposed upon at least a pair of contact surfaces of the utilized vibration attachment interface (e.g. which may for example comprise the preferred pair of contacts 12 disposed upon bifurcated connector 13, or a plurality of contacts 12 wherein support structure 24 is utilized—as described earlier), such as to enable a simple and easy application means to the patient 20, without the bother of attaching electrocardiographic leads and so forth.

It should be understood that while the embodiment shown to the portable emergency response system (and kit) advantageously incorporates the variant lightweight vibrator ("variant 3"), alternatively any known (or adaptable) low frequency (i.e. 1-120 Hz) vibrator (or percussion, or oscillation device by other name) of size and shape to enable hand held operation, with a suitable attachment interface for selected body surface contact (i.e. preferably enabling concentrated delivery of vibration between the rib space or spaces of the patient 20), being operable at high displacement amplitudes (i.e. >2 mm, and preferably >4 mm deflections) and engagement forces (i.e. >5-10 Newtons, and preferably >20 Newtons), may alternatively be used. Such vibration devices should preferably be adapted to portable battery operation, to enable the application of vibration therapy in community wherein an AC wall outlet may not always be available.

It is significant that acute coronary thrombotic obstruction in the community is one of the leading causes (if not the greatest cause) of death in the civilized world today.

Many modifications are possible to the emergency system without departing from the spirit or innovative concept of the invention.

With regards to the vibration source of preferred vibrator 10, while the embodiment shown advantageously employs an electromechanical transducer comprising a high powered linear stepper motor (such as to enable a high level of vibratory control and selectivity of frequency, displacement amplitude and vibratory displacement wave forms), alternatively any known (or adaptable) low frequency (i.e. 1-120 Hz) vibrator (or percussion device, or oscillation device by other name), with a suitable attachment interface for selected body surface contact (preferably enabling concentrated delivery of vibration between the rib space or spaces of the patient 20), being operable at high displacement amplitudes (i.e. >2 mm, and preferably >4 mm deflections) and engagement forces (i.e. > 5-10 Newtons, and preferably >20 Newtons), may alternatively be used, regardless of the level of operator enabled vibration control.

For example, to achieve the same level of vibration control, a lower stroke length enabled linear stepper motor (i.e. with a smaller stator tube) in conjunction with a displacement amplifier may be used. Linear stepper motors of lower stroke enablement are more common and commercially available, hence generally less expensive to employ. Alternatively, a high powered rotary stepper motor equipped with an exchangeable rotary to linear conversion element, or a specialized rotary to linear conversion element, (wherein the conversion element independently or in concert with the motor operation, enables adjustable displacement amplitude emission control) may be used. Conversion elements of this type are described (for example) in U.S. Pat. Nos. 6,027,444 and 827,133 incorporated herein by reference. Furthermore, a rotary stepper motor configured to oscillate controllably in an up and back manner along an arc of less than or equal to 180 degrees (and preferably less than 120 degrees) in conjunction with a cam or crank may be used to take the functional place of the provided "linear" stepper motor. Rotary motors are generally less expensive than linear motors. In yet a further variation, a ceramic servo motor coupled to a linear stage (as per modern, state of the art technology offered by Nanomotion LTD, incorporated herein by reference), could be utilized to replace the provided linear stepper motor, and provide virtually unlimited linear motion control.

For example, if only selectable displacement amplitude control is required, the electromechanical transducer may comprise any high powered rotary motor interfaced with a specialized cam or crank, wherein the cam or crank is exchangeable, or independently adapted to enable adjustable displacement amplitude control (e.g. as per technology in U.S. Pat. Nos. 6,027,444 or 827,133 mentioned previously); a high powered linear motor of any type operational at a predetermined stroke coupled to a specialized linear conversion element which is adapted to enable variable displacement amplitude control (such as, for example a lever system with an adjustably located fulcrum); a ceramic servo motor coupled to a linear stage (as above); or a linear stepper motor without the enablement of varying displacement wave shape control.

For example, if only variable displacement wave form control is required, then any high powered rotary stepper motor with a rotary to linear conversion element could be utilized. Alternatively, a ceramic servo motor coupled to a rotary stage (with rotary to linear conversion element), or a ceramic servo motor coupled to a linear stage could be used. Furthermore, in the case high impact "pulsed", or "square wave" vibration is desired (i.e. as a sole wave shape with a steep displacement rise per stroke—for deeper penetration and superior disruptive action) a technology as per U.S. Pat. Nos. 5,951,501 or 6,682,496 may be used, (or any other known technology), which utilizes a rotary motor with a specially engineered cam which is engineered to enable "striking" of a contact surface in a percussive manner. It should be noted that if a "pure" sinusoidal displacement wave form is desired (i.e. as a sole wave shape—which has demonstrated superior vasodilatation characteristics) a rotary motor (of any type) with a rotary to linear conversion element such as a cam or crank may be employed.

For example, if selectable "force" or "power" of vibration control (i.e. max force/stroke, and/or force wave shape control) is desired at a given frequency (as opposed to exacting displacement amplitude control and/or displacement wave shape control); a linear induction motor with adjustable force or power control, a linear permanent magnet motor with adjustable force or power control, a linear stepper motor with adjustable force or power control, a high powered speaker coil with adjustable power or volume control, a shaker with adjustable force or power control, a ceramic servo motor coupled to a linear or rotary stage with force or power adjustment control, or a plurality of select-ably aligned eccentric spinning weights rotating in adjustable relation to one another (as in variable force pile driving technology), may be used. Furthermore, a furniture item such as a chair or bed containing an adjustable force and/or waveform vibrator or vibrators (i.e. for vibration to the backside of the patient 20, such as in treatment in acute myocardial cases) may be used as a new application for a known technology. Examples of such vibrating chairs or beds, which necessarily provide reciprocating motion in a direction perpendicular to the long axis of the thoracic cavity and torso in cardiac applications (such as to enable significant penetration of the vibratory signal to the structures within the thoracic cavity) are disclosed in Canadian Patent Application No. 2430229, PCT Application No. WO 00/67693, and Japanese Utility Model Application No. Hei 296 133, which are incorporated herein by reference.

For example, if no (or minimal) vibratory control is desired, then any commercially available high powered vibratory massage or percussion system (i.e. providing greater than 2 mm deflections) operable under reasonable load (i.e. at least 5-10 N, and preferably at least about 20-100 N), such as for example the Mini Pro 2 Thumper™, Thumper™, Homedics Professional Percussion Massager model 1 PA-1H, Sharper Image Massager Model HF 757, OSIM Tappie, OSIM Turbo 2, OSIM iMedic Chair (i.e. for applications to the upper back region), OSIM ChiroPro (i.e. for applications to the posterior and lateral aspects of the neck), and the "deep muscle stimulator device" as disclosed by Pivaroff in U.S. Pat. No. 6,682,496 which is incorporated herein by reference, may be used as a new application for a known technology. These devices (many of which advantageously comprise,— or could be easily adapted to provide—a pair of contacts), typically emit one solitary high displacement amplitude stroke without a displacement amplitude regulating control, hence control of the applied forces to the body surface treated (to tailor the intensity of the application to suit the tolerance level of the patient 20), may be achieved via use of a cloth or cushion (i.e. to dampen application forces) or via a modulation of the engagement force applied to the vibrator against the application site. Such vibrators, (all of which tend to run exclusively on AC power cord), may be preferably (and easily) adapted by those skilled in the art of vibration device manufacture for portable battery operation to enable use in the field (or community), wherein no AC wall outlet may be available.

Also, while the preferred embodiment (apparatus) discloses a single motor located within housing 14 of vibrator 10, a pair or a plurality beyond a pair of motors may also be used (for example, one motor for each contact 12).

It should also be noted that there is effectively no definable maximal nor minimal limit to displacement amplitude or engagement force applied in emergency vibration therapy (i.e. the intensity emitted is generally a function of the tolerance of the patient 20 which will vary markedly). Any of the above variations to vibration source may be therefore adapted in size and scale to enable vibration at higher or conversely lower loads and displacement amplitudes than what is otherwise disclosed according to the invention. For example, while the preferred embodiment shown (i.e. vibrator 10) provides a peak displacement amplitude of up to 15 mm, this enablement is generally in excess of what is typically required, and a device limited to lower peak displacement amplitudes (i.e. with an upper limit as low as about 4-8 mm), may alternatively be employed for satisfactory results. Lower peak displacement amplitude devices are potentially "safer" (i.e. as the "tolerance" level of the patient 20 may be difficult to judge at the time of treatment), and confer lighter weight more compact systems, which are generally easier to maneuver and operate by hand. In an exemplary alternative embodiment, the vibrator employed may be operable to the maximum displacement amplitudes allowable (i.e. deemed safe) under the officiating governmental regulatory body or bodies of the country wherein the vibrator is to be commercialized.

With regards to the preferred attachment interface, while the embodiment shown incorporates shaft 16 projected away from housing 14 for transmission of vibration to contact, or preferably, contacts 12 to the patient 20, shaft 16 is not an essential component of vibrator 10 (or provided variant), and any transmission piece, or even the attachment interface itself, may be operatively linked directly to the active end of the electromechanical transducer within housing 14 of vibrator 10 (or variant). An attachment design like that of Homedics Model PA-100 massager (which incorporates a pair of electronically adjustably spaced vibration heads intimately mounted through the active end of the housing of the vibration device) is an exemplary alternative, and is incorporated herein by reference. Also, any of the aforementioned variations to contact 12 attachment (including suction cups, a single contact 12, a plurality beyond a pair of contacts 12, and variant contacts enabling ultrasonic imaging and/or LFUS wave form emissions) may be utilized solely, or in any combination, as per the methods described, to best suit the clinical situation and/or preference of the operator.

In yet another possible embodiment of attachment, the preferred contacts 12 may be replaced by a resilient nondistortable container filled with a substantially incompressible fluid overlain with a semi-compliant membrane (i.e. of size and shape such as to enable bridging of the sternum), wherein the vibration emitted from the active components of vibrator 10 (or variant) may be transmitted through the incompressible fluid and membrane and thereafter to the patient 20. The semi-compliant membrane (which comprises the patient 20 tissue interface) is highly resistant to longitudinal strain hence conservation of volume is achieved and vibration is efficiently transmitted. This arrangement (which enables an exacting contoured fit to the body surface treated) offers a potentially more comfortable application to the patient 20.

The engagement of the utilized vibrator (or percussion device by other name) to the selected body surface of the patient 20 may be varied in many ways. While the embodiments shown comprises use of the hand(s) of an operator, clamp 100 or 101 or belt 130 (and variations thereof, alternatively the employed vibration source may be engaged by means of an upper back support of a chair (e.g. such as in the OSIM iMedic Chair, disclosed herein by reference), or stretcher (or table), wherein the selected vibrator (or percussion instrument) is housed and preferably maneuverable within or through the upholstery of the supportive unit.

It is also possible to utilize more than one vibration device for placement to a plurality of locations along the body of the patient 20, such as to further ensure maximal penetration and effectiveness of vibration therapy for acute vascular disturbances. In this alternative embodiment the vibration devices should optimally be operated in phase to one another (i.e. to avoid potential destructive interference of the therapeutic signal). This technique may be of particular relevance wherein an imaging technique to direct vibration therapy is not employed.

The disclosed "dual function" ultrasonic imaging system to direct (or target) vibration therapy may also be embodied in a variety of ways.

For example, while the embodiment shown (apparatus) describes a direct, end to end, contact between a low frequency vibration source and an ultrasonic imaging transducer (i.e. such that the ultrasonic imaging transducer is acoustically linked to the vibration source and thereby transmits the generated low frequency vibration to the patient 20 via a common application surface), the vibration source and ultrasonic imaging probe may alternatively be mounted "side by side" by either a pivot assembly or an adjustable bracket (as per technology disclosed to U.S. Pat. No. 5,919,139 incorporated herein by reference), or by hand, which in either case would reduce wear and tear on the relatively expensive ultrasonic imaging probe as the ultrasonic imaging probe itself would not vibrate. The variant "by hand" technique advantageously enables additional manual control (or maneuverability of the ultrasonic imaging transducer) which is generally required in ultrasonic imaging. In this alternative "side by side vibration/imaging" embodiment, the degree of therapeutic vibration reaching the targeted region (and thereby the optimized placement of the vibration source or vibrator), may be gauged (or confirmed) by doppler or 2D/m mode interrogation of the invasive structure targeted.

Furthermore, it should be understood that while an ultrasonic imaging transducer is preferably coupled to the active components of the preferred vibrator 10 (or alternatively the variant research vibrator for higher frequency applications), these arrangements are not critical and the ultrasonic imaging transducer may be coupled to any low frequency vibration source operable within the 1-1000 Hz range according to the invention (regardless of the level of provided vibratory emission control), as long as the low frequency vibration wave form emitted does not significantly alter or interfere with the functioning of the imaging HFUS (mega hertz) wave form. The vibration source in these cases (as the vibration emitted will be advantageously directed through a sonic penetration window) needn't necessarily be operational at high force or displacement amplitudes (i.e. to ensure therapeutic penetration), however high displacement amplitude and force enablement is nonetheless preferred in emergency situations. Such vibration sources (as stated previously) may comprise but should not be limited to: linear stepper motors, linear stepper motors with displacement amplification, linear (non stepper) motors, ceramic servo motors coupled to either a rotary (with cam) or linear stage, rotary motors with rotary to linear conversion elements, eccentrically spinning weights, magnetostrictive actuators, voice coils, and shakers (e.g. with or without neodymium magnet transducers).

As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims.

I claim

1. A non-invasive method of using a percussion device for treating a cardiac related ailment causing a state of low arterial blood flow within the thoracic cavity, comprising the steps of
   a) providing a percussion device with a contact interface enabling engagement of at least a pair of contact nodes spaced to provide simultaneous seating to opposing sides of a bony structure upon the thoracic cavity of a human adult,
   b) simultaneously engaging said at least a pair of contact nodes to opposing sides of a bony structure upon the thoracic cavity of a patient suffering from a cardiac related ailment causing a state of low arterial blood flow within the thoracic cavity, and
   c) applying mechanical percussion via said at least a pair of contact nodes simultaneously engaged to said opposing sides of a bony structure upon the thoracic cavity of said patient at a frequency between 1-1000 Hz, and a stroke length in the range of 0.1 mm-10 mm at any time during step 1 (b), whereby said applying mechanical percussion via said at least a pair of contact nodes simultaneously engaged to said opposing sides of a bony structure upon the thoracic cavity enables optimized localized acoustic transmission to the heart and coronary arteries thereupon in view to remediation of said cardiac related ailment causing said state of low arterial blood flow within said thoracic cavity of said patient.

2. The method of claim 1, whereby said percussion is delivered via said at least a pair of contact nodes at a stroke length of at least 1 mm.

3. The method of claim 2, wherein each of said at least a pair of contact nodes are sized and shaped to enable operative seating within a human rib space of an individual receiving percussion from said percussion device.

4. The method of claim 3, wherein said percussion device has greater than a pair of oscillatory contact nodes, wherein said greater than a pair of contact nodes are simultaneously applied to the anatomic left and right of the sternum at differing intercostal space levels.

5. The method of claim 2, wherein said at least a pair of contact nodes are adjustably spaced relative to one another.

6. The method of claim 2, wherein said at least a pair of contact nodes are simultaneously applied to a plurality of rib-spaces at differing intercostal space levels.

7. The method of anyone of claims 1 and 6 wherein said applying percussion is timed to cease during the systolic period of the cardiac cycle of said patient.

8. The method of claim 2, wherein said percussion device is sized and configured to enable hand held manoeuvring and engagement.

9. The method of claim 2, wherein said state of low arterial blood flow comprises a state of low coronary blood flow, whereby said percussion enhances coronary flow.

10. The method of claim 2, whereby said percussion device comprises a motor disposed within a housing enabling reciprocating motion of said at least a pair of contact nodes, whereby said at least a pair of contact nodes are mechanically linked to an active end of said motor and projected from said housing.

11. The method of claim 2, whereby said percussion device is enabled to track the electrical activity of the heart independent of an externally placed ECG monitor disposed remote from said percussion device.

12. The method of claim 1, wherein said at least a pair of contact nodes are engaged to at least one of the anterior chest wall anatomic left and right of the sternum, and the upper back anatomic left and right of the spine of said patient.

13. The method of claim 1, wherein said stroke length is at least 2 mm, and said frequency is in the range of 20 Hz to 120 Hz.

14. The method of claim 1, wherein an engagement force exerted upon said percussion device in application against said patient is measurable by a force meter.

15. The method of claim 1, wherein said cardiac related ailment comprises an acute thrombotic coronary obstruction, whereby said percussion enhances clearance of said acute thrombotic coronary obstruction.

16. The method of claim 1, wherein said state of low arterial blood flow relates to at least one of congestive heart failure and cardiogenic shock, whereby said percussion enhances left ventricular performance and thereby assists in remediating said at least one of congestive heart failure and cardiogenic shock.

17. The method of claim 1, wherein said contact interface is configured to enable a contoured fit to a chest wall surface receiving percussion following placement of said percussion device upon said chest wall surface.

18. The method of claim 1, whereby said percussion is delivered by a vibratory waveform comprising a lower frequency modulated upon a higher frequency.

19. The method of claim 1, whereby said percussion device enables selectable stroke length.

20. The method of claim 1, whereby vibration of an invasive region targeted by said percussion device is non-invasively confirmed at any point during step 1 (c), such as to ensure effective penetration of said percussion.

21. The method of claim 1, whereby the timing of the closure of the aortic valve is monitored by a non-invasive probe operable in conjunction with said percussion device, such as to enable verification of the timing of the end of systole of the cardiac cycle of said patient.

22. The method of claim 1, whereby said percussion device is applied with at least 50 newtons of engagement force by the hand of an operator, to ensure adequate transmission of said percussion.

23. A non-invasive emergency method for restoring coronary blood flow in a patient experiencing an acute coronary obstruction, comprising the steps of,
   a) providing a vibrator with a contact interface disposing at least a pair of oscillatory contacts spaced to enable simultaneous seating to the anatomic left and right of the sternum of a patient suffering from an acute coronary obstruction, and
   b) administering percussion at a frequency between 1-1000 Hz, and a stroke length in the range of 0.1 mm-10 mm to the chest wall, anatomic left and right of the sternum of said patient via said contacts,
whereby said percussion applied in concert to the anatomic left and right of the sternum enables optimized transmission to the heart and coronary arteries thereupon in view to remediation of said acute coronary obstruction.

24. The method of claim 23, whereby said percussion is delivered via said at least a pair of contacts at a stroke length of at least 1 mm.

25. The method of claim 24, wherein said contacts are sized and shaped to enable operative seating within a human ribspace, and are applied within the rib-spaces of said patient.

26. The method of claim 25, whereby said at least a pair of contacts are convexly shaped, such as to enhance fitted seating of said contacts within a ribspace.

27. The method of claim 24, wherein said contacts reciprocate back and forth in phase with one another during administration of said percussion.

28. The method of claim 23, wherein said percussion has a stroke length of greater than 2 mm, such as to ensure effective penetration of said percussion.

29. The method of anyone of claims 23, 25, and 28, wherein said percussion is timed to be turned off during the systolic period of the cardiac cycle of said patient.

30. The method of claim 23, whereby a plurality of ECG electrodes are disposed upon said contact interface of said vibrator, such as to enable an expedited means for tracking the heart rhythm through attainment of electrocardiographic information.

31. The method of claim 23, wherein an engagement force exerted upon said vibrator in application against said patient is measurable by a force meter operable in conjunction with said vibrator.

32. A non-invasive method of using a percussion device for delivering localized percussion to an external body surface generally overlying the heart of a patient in treatment of a heart attack, comprising the steps of,
   a) providing a percussion device with a contact interface enabling engagement of at least a pair of contact nodes spaced to provide simultaneous seating to opposing sides of a bony structure upon the thoracic cavity of a human adult,
   b) simultaneously engaging said at least a pair of contact nodes to opposing sides of a bony structure upon the thoracic cavity of a patient suffering from a heart attack
   c) applying mechanical percussion via said at least a pair of contact nodes simultaneously engaged to said opposing sides of a bony structure upon said thoracic cavity at a frequency between 1-1000 impacts per second, and a stroke length in the range of 0.1 mm-10 mm, and
   d) periodically halting said percussion during the systolic period of the cardiac cycle of said patient,
whereby said halting said percussion during the systolic period of the cardiac cycle assists in prevention of hemodynamic decay of said patient suffering from said heart attack, and said applying mechanical percussion via said at least a pair of contact nodes simultaneously engaged to said opposing sides of a bony structure overlying the thoracic cavity enable optimized transmission of the forces of said percussion to the heart and coronary arteries thereupon in view to treatment said heart attack.

33. The method of claim 32, whereby said percussion device delivers said percussion via said at least a pair of contact nodes at a stroke length of at least at least 1 mm.

* * * * *